United States Patent [19]

Youngdale et al.

[11] Patent Number: 5,245,046

[45] Date of Patent: Sep. 14, 1993

[54] α-AMINO-INDOLE-3-ACETIC ACIDS USEFUL AS ANTI-DIABETIC, ANTI-OBESITY AND ANTI-ATHEROSCLEROTIC AGENTS

[75] Inventors: Gilbert A. Youngdale, Portage; John C. Sih; Steven P. Tanis, both of Kalamazoo; Chiu-Hong Lin, Portage, all of Mich.

[73] Assignee: The Upjohn Company, Kalamazoo, Mich.

[21] Appl. No.: 689,033

[22] PCT Filed: Oct. 27, 1989

[86] PCT No.: PCT/US89/04711

§ 371 Date: May 8, 1991

§ 102(e) Date: May 8, 1991

Related U.S. Application Data

[63] Continuation-in-part of Ser. No. 270,554, Nov. 14, 1988, abandoned.

[51] Int. Cl.⁵ .................. C07D 407/06; C07D 209/20; C07D 209/06; C07D 209/22; C07D 209/24

[52] U.S. Cl. .................................... 548/495; 548/465; 548/504; 548/507

[58] Field of Search ................. 548/495, 465, 504, 507

[56] References Cited

U.S. PATENT DOCUMENTS

| | | | |
|---|---|---|---|
| 2,542,869 | 2/1951 | Hoffman | 260/297 |
| 3,000,888 | 9/1961 | Beikert | 260/247.2 |
| 3,074,942 | 1/1963 | Juhl et al. | 260/247.2 |
| 3,316,260 | 4/1967 | Shen et al. | 260/247.2 |
| 3,320,280 | 5/1967 | Gal et al. | 260/326.12 |
| 4,492,694 | 10/1985 | Blaszczak et al. | 424/246 |

FOREIGN PATENT DOCUMENTS

| | | |
|---|---|---|
| 7615 | 2/1980 | European Pat. Off. |
| 0031653 | 7/1981 | European Pat. Off. |
| 2345775 | 3/1974 | Fed. Rep. of Germany |
| 1100016 | 9/1955 | France |
| 85035 | 6/1985 | Luxembourg |
| 6415318 | 7/1965 | Netherlands |
| 6607754 | 12/1966 | Netherlands |
| 1080470 | 8/1967 | United Kingdom |
| 1087359 | 10/1967 | United Kingdom |

OTHER PUBLICATIONS

Derwent 89-089908/12.
Baker, John W., "Syntheses in the Indole Series", *Journal of Chemical Society*, pp. 458–460, (1940).
E. A. Dawes et al, "Metal Catalysis of Indole Production", *Nature*, 164, 705 (1949).
Marvin D. Armstrong et al, "The Indole Acids of Human . . . Indole Acids", *J. Biol. Chem.*, 232, 17 (1958).
Ernst Biekert et al, "Mannich–Kondensationen mit Glyoxylsaure", Ber., 97, 363–371 (1964).
N. Yoneda, "Synthesis of 12–methyl–. . . quinolizine", *Chem. Pharm. Bull*, 13, 1231–1240 (1965).
T. Kametani et al, "Studies on the Syntheses of Heterocyclic . . . Related Compounds", *J. Heterocycl. Chem.*, 5, 799–804, (1968).
Shun–ichi Yamada et al, "Ind.-N-alkylation of Tryptophan . . . Hydrazides", *Chem. Pharm. Bull.*, 13, 88–93 (1965).

(List continued on next page.)

*Primary Examiner*—David B. Springer
*Attorney, Agent, or Firm*—Sidney B. Williams, Jr.

[57] ABSTRACT

Provided are novel α-aminoindole-3-acetic acid derivatives having the formula

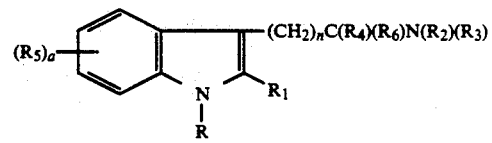

wherein R through R9 are as defined in the specification, and pharmacologically acceptable salts of compounds wherein $R_9$ is not OM, which are useful as antidiabetic, anti-obesity and anti-atherosclerotic agents.

10 Claims, No Drawings

OTHER PUBLICATIONS

Preobrazhenskaya et al, "Alpha-(3-indolyl)-beta-hydroxyamine and Its Derivatives", *Khim. Geterotsikl. Soedin*, 7, 778 (1971).

I. Arthur Mirsky et al, "The Hypoglycemic and . . . action of Tryptophan", *Endocrinology*, 59, 369 (1956).

I. Arthur Mirsky et al, "Hypoglycemic Action of . . . Tryptophan By Mouth", *Endocrinology*, 60, 318 (1957).

R. B. Sanders et al, "L-amino Acid Inhibition . . . Hyperglycemia", *Pharmacology*, 6, 155 (1971).

Agnes Szigeti et al., "Effects of Amino Acids on the Blood Sugar Levels", *Nahrung*, 13, 171 (1969).

Magdolna Bedo et al, "Interactions Between Some Nutrients and Metabolsm", *Egeszegtudomany*, 13, 249 (1969).

A. Lutkic et al, "Glycogen Formation and Structure . . . Metabolic States", *Bull. Sci., Cons. Acad. Sci. Arts RSF Yougoslavie*, Sect. A., 18, 8 (1973).

Jose A. Hedo et al, "Elevation of Plasma glucose . . . Ingestion in Man", *Clin. Exp.*, 26, 1131 (1977).

James S. Whitmann III, "Alteration of Glucose Tolerance . . . in Rats", *J. Nutr.*, 106, 631 (1976).

G. Carrozza et al, "Mechanism of the Intervention . . . in Glyconeogenesis", *Boll. Soc. Ital. Bio. Sper.*, 47, 535 (1971).

Kay Tanaka et al, "Synergistic Hypoglycemis Effects . . . with Hypoglycin A", *Pan-Am. Assoc. Biochem. Soc. Sypm.*, 3, 163 (1975).

Stephen A. Smith et al, "The hypoglycemic Action of Tryptophan in the Rat", *Biochem. Soc. Trans.*, 4, 1049 (1976).

Stephan A. Smith et al, "Tryptophan and the Control of Plasma . . . in the Rat", *Biochem. Soc. Trans.*, 168, 495 (1977).

Peter Lloyd et al, "Factors Affecting Trypophan-induced Hypoglycemia in Rats", *Biochem. Pharmacol.*, 31, 3563 (1982).

H. G. McDaniel et al, "Hypoglycemic Action of Tryptophan", *Diabetes*, 22, 713 (1973).

Carlo M. Veneziale et al, "Influence of L-Tryptophan and Its Metabolites . . . Perfused Liver", *Biochemistry*, 6, 2129 (1967).

U. Butturini et al, "Hypoglycemic Action of L-tryptophan and Tolbutamide", *Minerva Med.*, 1497 (1958).

Kozo Okamoto et al, "Prevention of Experimental Diabetes . . . Substances", *Tohoku J. Exptl. Med.*, 61, Suppl. 3, 36 (1955).

Fred Howard et al, "Tryptophan and Blood-Sugar Levels", *Am. J. Physiol.*, 153, 425 (1948).

V. G. Barone et al, "The Effect of Tyrosine and Tryptophan Administration to Diabetics", *Boll. Soc. Ital. Soc. Sper.* 6, 834 (1931).

α-AMINO-INDOLE-3-ACETIC ACIDS USEFUL AS ANTI-DIABETIC, ANTI-OBESITY AND ANTI-ATHEROSCLEROTIC AGENTS

This application is the national phase of international application PCT/US89/04711, which is a continuation-in-part of patent application Ser. No. 07/270,554 filed Nov. 14, 1988 now abandoned.

BACKGROUND OF THE INVENTION

The present invention provides novel compounds. More particularly, the present invention provides novel α-amino-indole-3-acetic acids, tryptophans and their derivatives. The compounds are useful as anti-diabetic, anti-obesity and anti-atherosclerotic agents.

INFORMATION DISCLOSURE

α-Amino-indole-3-acetic acid, tryptophan and some of their derivatives are described in the literature. Thus, U.S. Pat. No. 3,074,942 discloses α-amino-indole-3-acetic acid and derivatives thereof that are described as being useful as anaesthetics, CNS depressants and as antagonists to serotonin, acetylcholine and histamine. Some of these same compounds are disclosed in U.S. Pat. No. 4,492,694, to Baker, J. W., *Journal of Chemical Society*, 458 (1940); Casnati et al, *Gazz Chim. Ital.*, 93, 355 (1963); Dawes et al, *Nature*, 164, 705 (1949); Netherland published application 6,607,754; Armstrong et al, *J. Biol. Chem.*, 232, 17 (1958).

U.S. Pat. No. 4,492,694 discloses acylated α-amino derivatives of α-amino-indole acetic acid.

U.S. Pat. No. 3,320,280, Netherland application 6,415,318, U.S. Pat. No. 3,316,260 and British patent 1,087,359 disclose α-(3-indolyl)lower aliphatic acid derivatives that contain a methyl substituent at the 2-position of the indole ring. Another feature of the compounds disclosed in U.S. Pat. No. 3,320,280 is the presence of an aromatic carboxylic acyl radical of less than three fused rings attached to the nitrogen atom of the indole ring.

U.S. Pat. No. 3,000,888 and Biekert et al, *Ber.*, 97, 363 (1964) discloses an α-amino-indole-3-acetic acid derivative in which morpholino has been substituted for the α-amino group. It is described as being a therapeutic agent and an intermediate for preparing therapeutic agents.

German Offn. 2,345,775 and European patent application 7,615 published Feb. 6, 1980 discloses α-amino-indole-3-acetic acid derivatives having methyl and ethenyl substituents respectively, on α-carbon.

Yoneda, N., *Chem. Pharm. Bull.* 13, 1231 (1965), Kametani et al, *J. Heterocycl. Chem.*, 5, 799 (1968), French patent 1,100,016 and Yamada et al, *Chem. Pharm. Bull.*, 13, 88 (1965) disclose tryptophan derivatives in which one or both of the nitrogen atoms have been alkylated.

Preobrazhenskaya et al. *Khim. Geterotsikl. Soedin*, 7, 778 (1971) discloses tryptophan derivatives wherein the carboxylic acid group has been replaced by a hydroxyl, alkoxyl or benzyloxy group.

To applicants' knowledge, tryptophan is the only indole α-amino acid for which blood sugar altering effects have been reported.

Tryptophan reduced blood sugar levels in normal rats but not in rats with severe alloxan diabetes. Mirsky et al, *Endocrinology*, 59, 369 (1956) and *Endocrinology*, 6, 3180 (1957).

L-Tryptophan (2.5 mmoles/kg) administered i.p. to fasted rats blocked epinephrine-induced hyperglycemia 76%–89% and inhibited epinephrine-induced hyperglycemia to the same extent in both intact and diabetic rats indicatin that insulin was not involved in preventing the hyperglycemic response. Sanders et al, *Pharmacology*, 6, 155 (1971).

Fasting blood glucose levels were not affected by intragastric administration (120 mg/rat) of DL-tryptophan to female rats. The rise in blood glucose following glucose ingestion (1 g/rat) was decreased by DL-tryptophan as compared with rats receiving glucose only. Szigeti et al, *Nahrung*, 13, 171 (1969).

It was reported that tryptophan administered through the stomach does not produce hyperglycemia. Bedo et al, *Egeszegtudomany*, 13, 249 (1969).

Tryptophan facilitated deposition of glycogen, increased the liver weight, but decreased the pyruvate incorporation 7.5 times into liver glycogen. Lutkic et al, *Bull. Sci., Cons., Acad. Sci. Arts RSF yougoslavie*, Sect. A., 18, 8 (1973).

The oral administration of 10 g L-tryptophan to healthy human subjects induced a small but significant rise in blood sugar, a slight increase in blood insulin, a marked increase in plasma glucagon, and delayed increase in plasma growth hormone. This contrasted with the reported hypoglycemic effect of tryptophan in rats and with the well-documented inhibition of gluconeogensis by tryptophan and its metabolites in rat liver. Since tryptophan increased the circulating glucagon in man, the elevated blood sugar was probably due to enhanced glycogenolysis and/or gluconeogensis induced by this hormone. Hedo et al, *Metab., Clin. Exp.*, 26, 1131 (1977). Derwent 89-089908/12 refers to new tryptophan derivatives and their glycosides and their use to prevent or treat.

I.V. glucose tolerance was measured in rats fed various diets of defined L-tryptophan content. Within 14 days, animals which had been fed a tryptopha-deficient diet removed excess glucose from their blood at a reduced rate. The results suggest that dietary L-tryptophan is active in physiological regulation of carbohydrate metabolism. Wittman, J. S., *J. Nutr.*, 106, 631 (1976).

Among the amino acids, all stimulated the secretion of insulin and some were more active than insulin in inhibiting gluconeogenesis. The action of tryptophan on inhibiting gluconeogenesis was independent of its action on the secretion of insulin. Carrozza et al, *Boll. Soc. Ital. Bio. Sper.*, 47, 535 (1971).

Oral administration of tryptophan or lysine to rats 30 minutes prior to a subhypoglycemic i.v. injection of hypoglycin A resulted in a potent hypoglycemic effect. Tanaka et al, *Pan-Am. Assoc. Biochem. Soc. Symp.*, 3, 163 (1975).

The induction of hypoglycemia in both fed and 36 hour-starved rats by tryptophan (750 mg/kg, i.p.) was blocked by pretreatment with MK 486 or p-chlorophenylalanine (inhibitors of tryptophan decarboxylase and tryptophan 5-hydroxylase, respectively) and potentiated by paraglyine (monoamine oxidase inhibitor), suggesting the involvement of 5-hydroxytryptamine or a derivative thereof. I.P. administration of quinolate or indol-3-ylacetic acid to untreated rats or of tryptamine to pargyline-treated rats did not produce hypoglycemia. In pargyline-treated rats 5 hydroxytryptamine produced hyperglycemia, whereas 5-hydroxytryptophan had effects like those of tryptophan. The hypoglycemic response to tryptophan was prevented by the specific 5-hydroxytryptamine antagonist, methylsergide, and by experimental diabetes, and was enhanced by adrenalectomy. The response was also dependent on the presence of functional pancreatic β-cells, suggesting the involvement of insulin. Changes in liver metabolite and glucose concentrations were not related. The hypoglycemic action of tryptophan was associated with increased plasma β-hydroxybutyrate/acetoacetate ratios, including mediation through formation of intracellular 5-hydroxytryptamine. Smith et al, Biochem. Soc. Trans., 4, 1049 (1976) and Biochem. J. 168, 495 (1977).

The mechanisms whereby tryptophan administration leads to hypoglycemia in some groups of rats but not others have been investigated. These results were discussed in relation to previous discrepancies in the literature, and a unifying hypothesis for tryptophan-induced hypoglycemia is proposed. Lloyd et al, Biochem. Pharmacol., 31, 3563 (1982).

An increase in the rat hepatic level of gluconeogenic intermediates such as malate, aspartate, and citrate occurred after the i.p. administration of 10 mg L-tryptopha/100 g and was associated with 43 μg liver content of its metabolite quinolinic acid/g liver. The clinical implication of these findings are discussed. McDaniel et al, Diabetes, 22, 713 (1973).

The addition of 2.4 mM tryptophan to the medium perfusing isolated rat livers inhibited glucose production from added alanine. Such livers retained the capacity for converting fructose to glucose. Veneziale et al, Biochemistry, 6, 2129 (1967).

For examination of the theory of Mirsky (CA 51, 576$^d$) that L-tryptophan shows hypoglycemic action because of its inactivation of the insulin-inhibiting enzyme of the liver, rats were given L-tryptophan 26 mg/100 g after 24 hours of fasting; another group was given tolbutamide 100 mg/100 g; another received both and a fourth was a control. Glycemia dropped with L-tryptophan, tolbutamide, and the mixture during 240 minutes. Butturini et al, Minerva Med., 1497 (1958).

When given orally, L-tryptophan, DL-kynurenine, anthranilic acid, nicotinic acid, nicotinuric acid, indole-3-acetic acid, 5-hydroxytryptophan and 5-hydroxytryptamine creatinine sulfate produces a significant hypoglycemia in normal rats. Kynurenic acid produces a slight and nicotinamide a significant hyperglycemia. Quinolinic acid, picolinic acid, 5-hydroxyindoleacetic acid, indole, and skatole do not alter blood sugar levels. Indole-3-acetic acid and nicotinic acid do not reduce blood sugar levels in severely diabetic alloxanized rats. Mirsky et al, Endocrinology, 60, 318 (1957).

The minimum effective dose and the duration of the effect were determined for 37 substances (presumably including tryptophan) found to prevent alloxan diabetes, Okamoto, K., Tohoku J. Exptl. Med., 61, Suppl. 3, 36 (1955).

The effect of DL-tryptophan on blood sugar levels was studied with normal males as subjects. Doses of 0.25, 0.50 and 1.0 g per day for 14 days failed to lower the blood sugar levels. In five of the eleven cases given 0.5 g per day, a significant increase was noted. An attempt was made to pick up a transient effect of tryptophan on blood sugar levels one to three hours after ingestion, but no effect was found. Howard and Modlinger, Am. J. Physiol., 153, 425 (1948).

The intravenous injection of 90 cg tryptophan dissolved in 70 cc H$_2$O did not produce hyperglycemia or metabolic changes in normal vs. diabetic individuals. It did produce a slight increase in the alk. reserve. The intravenous injection of 5 cg tyrosine dissolved in 120 cc H$_2$O or in normal serum or the oral administration of 2 g tyrosine showed no hyperglycemia action in diabetes. Barone et al, Bull. Soc. Ital. Soc. Sper. 6, 834 (1931).

The compounds of the present invention are able to reduce blood glucose in severely insulin resistant mice. The major effect is on postprandial glucose concentrations indicating that the major effect may not be on inhibition of gluconeogenesis as has been suggested as a major mechanism for tryptophan-induced hypoglycemia in the preceding paragraphs. Although it has been hypothesized that metabolites of tryptophan might effect a decrease in fed glucose concentrations in normal rats and mice by a different mechanism (Smith and Pogson, Biochemical J., 168, 495 (1977)), neither tryptophan, 5-fluoro-tryptophan, nor 5-benzoyl-tryptophan at a dose of 100 mg/kg were effective in the insulin resistant model wherein the present invention was discovered. As some tryptophan analogs were effective in lowering fed blood glucose levels in this insulin resistant model, it is possible that extremely large amounts of tryptophan itself might give rise to a similar effect.

SUMMARY OF THE INVENTION

This invention relates to methods of preventing and treating diabetes, antherosclerosis and obesity in animals, including humans by aministering a compound of formula I wherein R is
(a) hydrogen,
(b) $C_1$–$C_{10}$ alkyl,
(c) $C_2$–$C_{10}$ alkenyl,
(d) $C_3$–$C_{10}$ alkynyl,
(e) phenyl,
(f) —C($R_6$)H-phenyl(—$R_5$)$_b$,
(g) —SO$_2$-phenyl(—$R_5$)$_b$,
(h) —C(O)$R_1$,
(i) —C(O)O$R_9$,
(j) —(CH$_2$)$_q$N($R_7$)($R_8$),
(k) —C(O)N($R_7$)($R_8$),
(l) —(CH$_2$)$_m$ Het,
(m) —CH$_2$C(O)$R_4$,
(n) —(CH$_2$)$_m$O(CH$_2$)$_m$CH$_3$,
(o) —CH$_2$—(C$_3$–C$_6$)cycloalkyl,
(p) C$_3$–C$_8$ cycloalkyl,
wherein a is 1 to 4,
b is 1 to 5,
m is 1 or 2,
n is 0 or 1,
p is 4 or 5,
q is 2 or 3,
wherein M is a pharmacologically acceptable cation;
wherein $R_1$ is
(a) hydrogen,
(b) $C_1$–$C_{10}$ alkyl,
(c) $C_2$–$C_{10}$ alkenyl,
(d) $C_2$–$C_{10}$ alkynyl,
(e) —phenyl(—$R_5$)$_b$,
(f) —CH$_2$-phenyl(—$R_5$)$_b$;
wherein $R_2$ is
(a) —CH($R_6$)-phenyl-($R_5$)$_b$;
(b) —CH$_2$— Het,
(c) $C_1$–$C_6$ alkyl
(d) —(CH$_2$)$_b$-phenyl(—R5)b
wherein het is a 5- or 6-membered saturated or unsaturated ring containing from one to thee heteroatoms (nitrogen, oxygen, sulfur); and including any bicyclic group in which any of the above heterocyclic rings is fused to a benzene ring or another heterocycle;
wherein $R_3$ is
(a) hydrogen,
(b) —C(O)$R_1$,
(c) —C(O)O$R_1$,
(d) —(CH$_2$)$_b$-phenyl($R_5$)$_b$
wherein $R_4$ is
(a) hydrogen,
(b) —C(O)$R_9$
wherein $R_5$ same or different is
(a) hydrogen,
(b) halogen,
(c) hydroxy,
(d) $C_1$-$C_{10}$ alkoxy,
(e) $C_3$-$C_{10}$ alkenyloxy,
(f) $C_3$-$C_{10}$ alkynyloxy,
(g) nitro,
(h) amino,
(i) —N($R_6$)($R_7$),
(j) —NHC(O)$R_1$,
(k) —OC(O)$R_1$,
(l) —C(O)$R_1$,
(m) trifluoromethyl,
(n) —SO$_2$N($R_6$)($R_7$),
(o) —S$R_8$,
(p) —C≡N,
(q) —C(O)O$R_6$,
(r) $C_1$-$C_4$ alkyl
(s) phenyl
(t) —O—CH$_2$—O—,
wherein $R_6$ is
(a) hydrogen,
(b) $C_1$-$C_{10}$ alkyl,
(c) —C(O)O$R_1$,
(d) phenyl,
wherein $R_7$ is
(a) hydrogen,
(b) $C_1$-$C_{10}$ alkyl,
wherein $R_8$ is
(a) hydrogen,
(b) $C_1$-$C_{10}$ alkyl,
(c) $C_3$-$C_{10}$ alkenyl,
(d) $C_3$-$C_{10}$ alkynyl,
(e) phenyl-($R_5$)$_b$,
(f) —CH$_2$-phenyl-($R_5$)$_b$,
(g) CH$_2$-het, and
wherein $R_9$ is
(a) hydrogen,
(b) hydroxy,
(c) OM,
(d) —O$R_8$,
(e) —N($R_6$)($R_7$),
and pharmacologically acceptable salts of compounds wherein $R_9$ is not OM;

with the proviso that when n is 0, $R_2$ is benzyl, substituted benzyl or alkyl, R is hydrogen, benzyl or substituted benzyl, $R_1$ is hydrogen or methyl, $R_3$ is hydrogen or methyl, $R_5$ is hydrogen, benzyloxy or methoxy, and $R_6$ is hydrogen, then $R_4$ cannot be benzyloxycarbonyl, ethoxycarbonyl, or C(O)OM;

with the proviso that when n is 1; R is hydrogen or methyl; $R_1$ is hydrogen; $R_2$ is benzyl; $R_3$ is hydrogen; $R_5$ is hydrogen; and $R_6$ is hydrogen, then $R_4$ cannot be carboxyl or methoxycarbonyl;

with the further proviso that when n is 0; R is hydrogen or 4-substituted benzyl; $R_1$ is hydrogen or methyl; $R_2$ is $C_1$-$C_4$ alkyll $R_3$ is hydrogen or $C_1$—$C_2$ alkyl; $R_5$ is hydrogen, methoxy, or benzyloxy; and $R_6$ is hydrogen, then $R_4$ cannot be ethoxycarbonyl, carboxyl, or propoxycarbonyl;

with the further proviso that the compound of Formula I is not:
Methyl α-[N-methyl-N-3-(trifluoromethyl)benzylamino]-1-benzylindole-3-acetate,
Methyl α-[N-methyl-N-3-(trifluoromethyl)benzylamino]-1-benzylindole-3-acetate hydrochloride,
α-[N-methyl-N-3-(trifluoromethyl)benzylamino]-1-benzylindole-3-acetic acid,
Methyl α-[3-(trifluoromethyl)benzylamino]indole-3-acetate hydrochloride,
Ethyl α-[3-(trifluoromethyl)benzylamino]indole-3-acetate hydrochloride,
α-[3-(trifluoromethyl)benzylamino]-1-benzylindole-3-acetic acid p-phenylphenacyl ester,
α-[3-(trifluoromethyl)benzylamino]-1-benzylindole-3-acetic acid 1-methyl-3-butenyl ester,
2-[3-(trifluoromethyl)benzylamino]-2-(1-benzyl-3-indolyl)ethanol,
Methyl α-[3-(trifluoromethyl)benzylamino]-1-acetoxymethylindole-3-acetate,
Methyl α-[3-(trifluoromethyl)benzylamino]-1-acetoxymethylindole-3-acetate hydrochloride,
Methyl α-(benzylamino)-indole-3-acetate,
α-(phenylpropylamino)-1-benzylindole-3-acetic acid,
Methyl α-[4-(aminosulfonyl)phenylethylamino]indole-3-acetate,
α-Methylamino-1-benzylindole-3-acetic acid,
α-Phenylethylamino)-1-benzylindole-3-acetic acid,
α-[4-(aminosulfonyl)phenylethylamino]-1-benzylindole-3-acetic acid,
α-[(tetrahydro-2-furanyl)methylamino]-1-benzylindole-3-acetic acid,
α-[3-(trifluoromethyl)benzylamino]-1-benzylindole-3-acetic acid N,N-dimethylamide,
Ethyl α-[3-(trifluoromethyl)benzylamino]-indole-3-acetate,
α-[(2-furylmethyl)amino]-indole-3-acetic acid,
α-benzylamino-indole-3-acetic acid,
α-[3-(trifluoromethyl)benzylamino]-1-benzylindole-3-acetic acid amide,
α-[4-(methoxycarbonyl)benzylamino]-1-benzylindle-3-acetic acid,
Methyl α-[3-(trifluoromethyl)benzylamino]-1-acetoxymethylindole-3-acetate,
Methyl α-[3-(trifluoromethyl)benzylamino]-1-acetoxymethylindole-3-acetate hydrochloride.

The compounds of this invention are useful as antidiabetic, anti-obesity and anti-atherosclerotic agents.

The compounds of this invention may be supplied in capsules, tablets, suppositories, powders, or as fluid solutions and/or suspensions in aqueous or non-aqueous vehicles or can be added to food. The compounds can be administered orally, intravenously, intramuscularly, intra-arterially, intraperitoneally, subcutaneously, sublingually, bucally to man or to other animals. The dosage of each of the uses is about 0.1–50 mg/kg. The dosage will vary with the route of administration and the physical state of the recipient. Also, for example, the dosage by the oral route will depend on the frequency of administration and the weight of the recipient.

Without further elaboration, it is believed that one skilled in the art can, using the preceding description, practice the present invention to its fullest extent. The following detailed examples describe how to prepare various compounds of the invention and are to be construed as merely illustrative, and not limitations of the preceding disclosure. Those skilled in the art will promptly recognize appropriate variations from the procedures both as to reactants and as to reaction conditions and techniques.

Preferred compounds are those of formula I wherein R is hydrogen or benzyl, $R_1$ is hydrogen, $R_2$ is trifluoromethylbenzyl or furylmethyl and $R_9$ is selected from the group consisting of hdyroxy, $OR_8$ and OM wherein $R_8$ is $C_1$–$C_{10}$ alkyl and M is a pharmacologically acceptable cation and their preferred utility is as anti-diabetic agents. Particularly preferred are the compounds α-[3-(trifluoromethyl)benzylamino]-1-benzylindole-3-acetic acid, methyl α-[3-(trifluoromethyl)benzylamino]-1-benzylindole-3-acetate hydrochloride, α-[3-(trifluoromethyl)benzylamino]-iondole-3-acetic acid, α-[(2-furylmethyl)amino]-1-benzylindole-3-acetic acid, α-[3-(trifluoromethyl)benzylamino]-1-benzyl-5-methoxyindole-3-acetic acid, α-[3-(trifluoromethyl)benzylamino]-1-benzyl-6-chloro-5-methoxyindole-3-acetic acid, and α-[3-(trifluoromethyl)benzylamino]-1-benzyl-6-methyl-5-methoxyindole-3-acetic acid.

The carbon atom content of various hydrocarbon-containing moieties is indicated by a prefix designating the minimum and maximum number of carbon atoms in the moiety, i.e., the prefix ($C_i$–$C_j$) indicates a moiety of the integer "i" to the integer "j" carbon atoms, inclusive. Thus ($C_1$–$C_4$)alkyl refers to alkyl of one to 4 carbon atoms, inclusive, or methyl, ethyl, propyl, butyl, and isomeric forms thereof. $C_4$–$C_7$ cyclic amino indicates a monocyclic group containing one nitrogen and 4 to 7 carbon atoms.

Examples of ($C_3$–$C_{10}$)cycloalkyl which include alkyl-substituted cycloalkyl containing a total of up to 10 total carbon atoms, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, cyclopentyl, 2,2-dimethylcyclopentyl, cyclohexyl, cycloheptyl, cyclooctyl, cyclononyl, cyclodecyl and isomeric forms thereof.

Examples of aryl include phenyl, naphthyl (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4- 2,3,6-, or 2,4,5-)-trimethylphenyl, (o-, m-, or p-)fluorophenyl, (o-, m-, or p-trifluoromethyl)phenyl, 4-fluoro-2,5-xylyl, (2,4-, 2,5-, 2,6-, 3,4, or 3,5-)difluorophenyl, (o-, m-, or p-)chlorophenyl, 2-chloro-p-tolyl, (3-, 4-, 5- or 6-)chlor-o-tolyl, 4-chloro-2-propylphenyl, 2-isopropyl-4-chlorophenyl, 4-chloro-3-fluorophenyl, (3- or 4-)chloro-2-fluorophenyl), (o-, m-, or p-)trifluoro-methylphenyl, (o-, m-, or p-)ethoxyphenyl, (4- or 5-)chloro-2-methoxy-phenyl, and 2,4- dichloro(5- or 6-)methylphenyl, and the like.

Examples of -Het include: 2-, 3-, or 4-pyridyl, imidazolyl, indolyl, $N^{in}$-formyl-indolyl, $N^{in}$-$C_1$–$C_5$alkyl-C(O)-indolyl, [1,2,4]triazolyl, 2-, 4-, or 5-pyrimidinyl, 2- or 3-thienyl, piperidinyl, pyrryl, pyrrolinyl, pyrrolidinyl, pyrazolyl, pyrazolinyl, pyrazolidinyl, imidazolinyl, imidazolidinyl, pyrazinyl, piperazinyl, pyridazinyl, oxazolyl, oxazolidinyl, isoxazolyl, isoxazolidinyl, morpholinyo, thiaozlyl, thiazolidinyl, isothiazolyl, isothiazolidinyl, quinolinyl, isoquinolinyl, benzimidazolyl, benzofuryl, benzothiazolyl, benzoxazolyl, furyl, thienyl, phthalimidyl, and benzothienyl. Each of these moieties may be substituted benzofuran as noted above.

As would be generally recognized by those skilled in the art of organic chemistry, a heterocycle as defined herein or -Het would not be bonded through oxygen or sulfur or through nitrogen which is within a ring and part of a double bond.

Halo is halogen (fluoro, chloro, bromo, or iodo) or trifluoromethyl. Examples of pharmaceutically acceptable acid addition salts include: acetate, adipate, alginate, aspartate, benzoate, benzenesulfonate, bisuflate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate.

Examples of pharmaceutically acceptable cations include: pharmacologically acceptable metal cations, ammonium, amine cations, or quaternary ammonium cations. Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are also within the scope of this invention. Pharmaceutically acceptable amine cations are those derived from primary, secondary, or tertiary amines.

EMBODIMENTS OF THE INVENTION

The α-amino-indole-3-acetic acids and their derivatives wherein n is 0 can be prepared by condensing an indole unsubstituted at the 3-position with glyoxylic acid or esters thereof and a primary or secondary amine. Reactions of this type are described in U.S. Pat. No. 3,074,942, the essential parts which are incorporated herein by reference and are illustrated in Charts I and II. A preferred method involves adding 1.1 equivalents of glyoxlic acid monohydrate to a solution of 1.0 equivalent of an appropriate indole and one eqivalent of the appropriate amine. The resulting solution is allowed to stand overnight and then the separated solid is collected by filtration, washed with methanol and dried to obtain the desired product.

Compounds wherein n=1 can be prepared from tryptophan and its known derivatives.

Compounds of this invention having a migrated carboxy group, I', can be prepared by the process illustrated in Chart III. In this process an indole-3-carboxyaldehyde is reacted with an amine such as methylphenylglycinate hydrochloride in the presence of a solvent. The ratio of amine to aldehyde is about 3 to 1 and the reaction is conducted at a temperature of about 25° to about 40° for a period of about 24 hours to about 72 hours.

The starting materials utilized to prepare the compounds of this invention are either commercially available or can be prepared by methods well known in the art. For example, see K. Sukata, *Bull. Chem. Soc.*, Japan, 56, 280 (1982). Khan et al, Chem. Pharm. Bull., 25, 3110 (1970), disclose a procedure for preparing 1-phenylindole; 1-benzyl-2-phenylindole was prepared by Suvorou et al, *J. Org. Chem.*, USSR, 16, 766 (1980) by the Fischer indole synthesis. Ehrhart et al, *Arch. Pharm.*, 294, 550 (1961) disclosed a process for preparing 1-benzyl-5-methoxyindole, 1-benzyl-5-chloroindole and 1-benzyl-2-methoxyindole and 1-benzyl-5-fluorindole. Rubottom et al., Org. Syn., 54, 60 (1974) discloses a process for preparing 1-allylindole. Kelly et al, Synthesis, 544 (1972) discloses a process for preparing methyl glyoxylate.

DESCRIPTION OF THE PREFERRED EMBODIMENTS

Preparation 1

1-Benzylindole

To a stirred mixture of sodium amide (prepared from 19.6 g, 0.85 mole of sodium and a few mg of Fe(NO$_3$)$_3$·9H$_2$O) and 800 mL of liquid NH$_3$ (a dry ice condenser was used) was added a solution of 100 g (0.85 mole) of indole in 250 mL of dry ether during 15 minutes. The mixture was stirred for 30 minutes and then a solution of 107.8 g (0.85 mole) of benzyl chloride in 100 mL of dry ether was added during 30 minutes. The ammonia was allowed to evaporate overnight. The sides of the flask were washed down with MeOH and then 500 mL of H$_2$O was added. The mixture was extracted with ether (2×500 mL). The combined ether extracts were washed with 250 mL of H$_2$O and dried over MgSO$_4$. The solvent was evaporated. The residue was distilled at 2 mm: fr 1, b.p. 172°–183°, fr II, b.p. 183°–186°, 5 g; fr III, b.p. 186°–187°, 10.9 g; fr IV, b.p. 187°–191°, 121.8 g; fr V, b.p. 191°–197°, 13.9 g. Fractions III–V solidified upon standing several hours. Fraction IV had m.p. 42°–43°. Fraction III was crystallized from aqueous MeOH giving 9.9 g of colorless needles, m.p. 42.5°–43.5°. Fraction V was crystallized from aqueous MeOH giving 11.6 g of colorless needles, m.p. 43°–45.5°. The total yield was 143.3 g (81.5%).

Preparation 2

1-(4-Chlorobenzyl)indole

A mixture of 11.72 g (0.1 mole) of indole, 17.71 g (0.11 mole) of 4-chlorobenzyl chloride, 33 g (0.5 mole) of 85% KOH, 14 mL of H$_2$O, 2.5 g (2.5 mmoles) of PEG-1000 and 100 mL of toluene was stirred and heated at 55°–65° for 22 hours. After cooling to room temperature, 50 mL of H$_2$O was added. The layers were separated. The aqueous layer was extracted with 100 mL of toluene. The combined organic phases were washed with 2N HCl (2×50 mL), H$_2$O (2×50 mL), and 50 mL of brine and dried over MgSO$_4$. Evaporation of the solvent left 29 g of orange-brown oil. The oil was chromatographed on a 1100 g column of silica gel. The column was eluted with 1:1 CH$_2$Cl$_2$-Skellysolve B and 200 mL fractions were collected. The fractions were assayed by silica gel tlc (1×4") (25% CH$_2$Cl$_2$-Skellysolve B). Fractions 12–19 were combined giving 23.11 g of crude product as a pink oil. The oil was chromatographed on a 1100 g column of silica gel. The column was eluted with 25% CH$_2$Cl$_2$-Skellysolve B and 200 mL fractions were collected. The fractions were assayed as before. Fractions 20–30 were combined giving 20.33 g (84%) of 1-(4-chlorobenzyl)indole as a yellow oil.

Physical characteristics are as follows:

NMR (CDCl$_3$); δ 5.22 (s, 2H), 6.6 (d,J=3 Hz, 6.9–7.4 (m, 8H), 7.57–7.8 (m, 1H).

Preparation 3

1-Phenylindole

A mixture of 17.57 g (0.15 mole) of indole, 23.55 g (0.15 mole) of bromobenzene, 21 g of anhydrous potassium carbonate, 0.75 g of CuO, and 30 mL of DMF was stirred and heated under reflux for 43 hours. The cooled mixture was diluted with 200 mL of H$_2$O and extracted with 150 mL of ether. The extract was washed with H$_2$O (2×50 mL) and 50 mL of brine and dried over MgSO$_4$. The oil was chromatographed on the solvent left 35.7 g of brown oil. The oil was chromatographed on a 1100 g column of silica gel. The column was eluted with 25% CH$_2$Cl$_2$-Skellysolve B and 200 mL fractions were collected. The fractions were assayed by silica gel tlc (1×4") (25% CH$_2$Cl$_2$-Skellysolve B). Fractions 15–22 were combined giving 5.86 g (20%) of 1-phenylindole as a yellow oil.

Physical characteristics are as follows:

NMR (CDCl$_3$): δ 6.7 (d,J=3 Hz, 1H), 7.1–7.9 (m, 10H).

Preparation 4

1-Benzyl-2-phenylindole and 1,3-Dibenzyl-2-phenylindole

A mixture of 19.33 g (0.1 mole) of 2-phenylindole, 13.92 g (0.11 mole) of benzyl chloride, 33 g (0.5 mole) of 85% KOH, 14 mL of H$_2$O, 2.5 g (2.5 mmoles) of PEG-1000, and 100 mL of toluene was stirred and heated at 55°–60° for 24 hours. After cooling to room temperature, 100 mL of H$_2$O was added. The layers were separated. The aqueous layer was extracted with 100 mL of toluene. The combined toluene phases were washed with 2N HCl (2×50 mL), H$_2$O (2×50 mL), and 50 mL of brine and dried over MgSO$_4$. Evaporation of the solvent left 32.3 g of dark brown oil. The oil was chromatographed on a 1100 g column of silica gel. The column was elut4d with 25% CH$_2$Cl$_2$-Skellysolve B and 200 mL fractions were collected. The fractions were assayed by silica gel tlc (1×4") (25% CH$_2$Cl$_2$-Skellysolve B). Fractions 18–20 were combined giving 3.74 g (13%) of 1-benzyl-2-phenylindole as a solid.

Physical characteristics are as follows:

NMR (fr 19) (CDCl$_3$): δ 5.38 (s,2H), 6.7 (s,1H), 7.0–7.9 (m,14H).

Fractions 21–25 were combined giving 10.38 g of a mixture of 1-benzyl-2-phenylindole and 1,3-dibenzyl-2-phenylindole as a pale yellow oil which partially solidified upon standing.

Physical characteristics are as follows:

NMR (fr 28) (CDCl$_3$): δ 4.1 (s,2H), 5.28 (s,2H), 6.9–7.6 (m,19H).

Preparation 5

1-Benzyl-5-methoxyindole and 1,3-Dibenzyl-5-methoxyindole

A mixture of 5 g (33.97 mmoles) of 5-methoxyindole, 4.73 g (37.37 mmoles) of benzyl chloride, 11.2 g (170 mmoles) of 85% KOH, 5 mL of H$_2$O, 0.83 g (0.83 mmoles) of PEG-1000, and 50 mL of toluene was stirred and heated at 55°–60° for 21 hours. After cooling to room temperature, 100 mL of H$_2$O was added. The layers were separated. The aqueous layer was extracted with 100 mL of toluene. The combined toluene phases were washed with 2N HCl (2×50 mL), H$_2$O (2×50 mL), and 50 mL of brine and dried over MgSO$_4$. Evaporation of the solvent left 9.86 g of brown oil. The oil was chromatographed on a 400 g column of silica gel. The column was eluted with 1:1 $CH_2Cl_2$-Skellysolve B and 100 mL fractions were collected. The fractions were assayed by silica gel tlc (2×8") (1:1 $CH_2Cl_2$-Skellysolve B). Fraction 15 contained 0.78 g of a mixture of 1-benzyl-5-methoxyindole and 1,3-dibenzyl-5-methoxyindole as an oil.

Physical characteristics are as follows:

NMR (fr 15) ($CDCl_3$): $\delta$ 3.78 and 3.88 (s;s,3H), 4.1 (s,1H), 5.2 and 5.28 (s's,2H), 6.51 (d,J=3 Hz,<1H), 6.77–7.4 (m,9.5H).

Fraction 16 was crystallized from $CH_2Cl_2$-Skellysolve B giving 1.49 g of 1-benzyl-5-methoxyindole as a white solid. Fractions 17–27 were combined giving 4.44 g of 1-benzyl-5-methoxyindole as a white solid. The total yield of 1-benzyl-5-methoxyindole was 5.93 g (74%).

Physical characteristics are as follows:

NMR (fr 22) ($CDCl_3$): $\delta$ 3.8 (s,3H), 5.25 (s,2H), 6.5(d,J=3 Hz, 1H), 6.8–7.4 (m,9H).

Preparation 6

1-Benzyl-5-chloroindole

To a solution of 0.8 g (3.03 mmoles) of 18-crown-6 in 100 mL of dry ether was added 4.39 g (39.12 mmoles) potassium tert-butoxide. The mixture was stirred while 5.08 g (33.51 mmoles) of 5-chloroindole was added. The stirring was continued for 0.5 hour. Most of the solid dissolved. Then 6.69 g (39.11 mmoles) of benzyl bromide in 40 mL of ether was added during 0.5 hours. The stirring was continued for 27 hours. Water (100 mL) was added. The layers were separated. The aqueous layer was extracted with ether (2×75 mL). The combined ether phases were washed with 50 mL of brine and dried over $MgSO_4$. Evaporation of the solvent left 9.17 g of orange oil. The oil was chromatographed on a 700 g column of silica gel. The column was eluted with 1:2 $CH_2Cl_2$-Skellysolve B and 200 mL fractions were collected. The fractions were assayed by silica gel tlc (2×8") (1:2 $CH_2Cl_2$-Skellysolve B). Fractions 10–14 were combined giving 7.26 g (90%) of 1-benzyl-5-chloroindole as a yellow oil.

Physical characteristics are as follows:

NMR (fr 10) ($CDCl_3$): $\delta$ 4.06 (s, trace), 5.28 (s, 2H), 6.52 (d, J=3 Hz, 1H), 7.02–7.58 (m,8H), 7.63–7.73 (m, 1H).

Preparation 7

1-Benzyl-2-methylindole and
1,3-dibenzyl-2-methylindole

A mixture of 13.11 g (0.1 mole) of 2-methylindole, 13.92 g (0.11 mole) of benzyl chloride, 33 g (0.5 mole) of 85% KOH, 14 mL of $H_2O$, 2.5 g (2.5 mmoles) of PEG-1000, and 100 mL of toluene was stirred and heated at 60° for 23 hours. After cooling to room temperature, 100 mL of $H_2O$ was added. The layers were separated. The aqueous layer was extracted with 100 mL of toluene. The combined toluene phases were washed 2N HCl (2×50 mL), $H_2O$ (2×50 mL), and 50 mL of brine and dried over $MgSO_4$. Evaporation of the solvent left 26.98 g of dark brown oil. The oil was chromatographed on a 1100 g column of silica gel. The column was eluted with 25% $CH_2Cl_2$-Skellysolve B and 200 mL fractions were collected. The fractions were assayed by silica gel tlc (1×4") (25% $CH_2Cl_2$-Skellysolve B). Fractions 20–22 were combined giving 2.08 g (9%) of 1-benzyl-2-methylindole as a yellow oil which solidified.

Physical characteristics are as follows:

NMR (fr 22) ($CDCl_3$): $\delta$ 2.32 (s, 3H), 5.23 (s, 2H), 6.2–6.6 (br, 1H), 6.9–7.42 (m, 7H), 7.5–7.78 (m, 2H).

Fractions 23–28 were combined giving 7.50 g of yellow oil consisting of 1-benzyl-2-methylindole and 1,3-dibenzyl-2-methylindole.

Physical characteristics are as follows:

NMR (fr 33)($CDCl_3$): $\delta$ 2.29 (s, 3H), 4.09 (s, 2H), 5.23 (s, 2H), 6.88–7.58 (m, 14H).

Preparation 8

1-Benzyl-2-methylindole and
1,3-dibenzyl-2-methylindole

To a solution of 2.39 g (9.04 mmoles) of 18-crown-6 in 250 mL of dry ether was added 13.1 g (116.7 mmoles) of potassium tert-butoxide. The mixture was stirred while 13.11 g (100 mmoles) of 2-methylindole was added. The stirring was continued for 0.5 hour. Most of the solid dissolved. Then 20 g (116.9 mmoles) of benzyl chloride in 120 mL of ether was added during 45 minutes. The stirring was continued for 21.5 hours. Water (200 mL) was added. The layers were separated. The aqueous layer was extracted with ether (2×75 mL). The combined ether phases were washed with 50 mL of brine and dried over $MgSO_4$. Evaporation of the solvent left 25.85 g of dark brown oil. The oil was chromatographed on a 1100 g column of silica gel. The column was eluted with 25% $CH_2Cl_2$-Skellysolve B and 200 mL fractions were collected. The fractions were assayed by silica gel tlc (1×4") (25% $CH_2Cl_2$-Skellysolve B). Fractions 22–25 were combined giving 2.28 g (10%) of slightly impure 1-benzyl-2-methylindole as a pale yellow oil which solidified upon standing. Fractions 26–35 were combined giving 8.42 g of 1-benzyl-2-methylindole and 1,3-dibenzyl-2-methylindole as a pale yellow oil. The 8.42 g was combined with the 7.50 g of a similar mixture from fractions 23–28, and chromatographed on a 1100 g column of silica gel. The column was eluted with 25% $CH_2Cl_2$-Skellysolve B and 200 mL fractions were collected. The fractions were assayed as before. Fractions 21–24 were combined giving 3.59 g of 1-benzyl-2-methylindole as a pale yellow oil which solidified. Fractions 25–30 were combined giving 7.66 g of a mixture of 1-benzyl-2-methylindole and 1,3-dibenzyl-2-methylindole as an oil.

Preparation 9

1-Allylindole

To a solution of 2.39 g (9.04 mmoles) of 18-crown-6 in 250 ml of dry ether was added 13.1 g (116.7 mmoles) of potassium tert-butoxide. The mixture was stirred while 11.72 g (100 mmoles) indole was added. The stirring was continued for 3 hours. All of the solid did not dissolve. Then 14.1 g (116.5 mmoles) of allyl bromide in 100 ml of ether was added during 0.5 hour. The stirring was continued for 67.5 hours. Water (200 ml) was added. The layers were separated. The aqueous layer was extracted with ether (2×75 ml). The combined ether phases were washed with 50 ml of brine and dried over $MgSO_4$. Evaporation of the solvent left 16.02 g of brown oil. The oil was chromatographed on a 1100 g column of silica gel. The column was eluted with 10% acetone-Skellysolve B and 2200 ml fractions were collected. The fractions were assayed by silica gel tlc (1×4") (10% acetone-Skellysolve B). Fractions 17–23 were combined giving 11.60 g (74%) of 1-allylindole as a yellow brown oil.

Physical characteristics are as follows:

NMR (fr 22) (CDCl$_3$): δ 4.5–4.8 (m, 2H), 4.9–5.25 (m, 2H), 5.7–6.2 (m, 1H), 6.52 (d, J=3 Hz, 1H), 7.0–7.48 (m, 4H), 7.58–7.78 (m, 1H).

Preparation 10

1-Benzyl-5-methylindole

To a stirred mixture of sodium amide (prepared from 0.9 g 39.13 mmoles of sodium) and ca 100 ml of liquid ammonia was added a solution of 5.08 g (38.73 mmoles) of 5-methylindole in 100 ml of ether during 5 minutes. The mixture was stirred for 1.5 hours. Then a solution of 5.15 g (40.68 mmoles) of benzyl chloride in 100 ml of ether was added during 10 minutes. The mixture was stirred for two hours. The ammonia was allowed to evaporate overnight. The inside of the flask was washed down with MeOH. Then 150 ml of H$_2$O was added. The layers were separated. The aqueous layer was extracted with 100 ml of ether. The combined ether phases were washed with 50 ml of brine and dried over MgSO$_4$. Evaporation of the solvent left 9.41 g of oil. The oil was chromatographed on a 700 g column of silica gel. The column was eluted with 30% CH$_2$Cl$_2$-Skellysolve B and 200 ml fractions were collected. The fractions were assayed by silica gel tlc (2×8") (25% CH$_2$Cl$_2$-Skellysolve B). Fractions 12–17 were combined giving 4.52 g (53%) of 1-benzyl-5-methylindole as a yellow-green oil.

Physical characteristics are as follows:

NMR (CDCl$_3$): δ 2.42 (s, 3H), 5.23 (s, 2H), 6.49 (d, J=4 Hz, 1H), 6.91–7.58 (m, 9H).

Preparation 11

1-Benzyl-5-fluoroindole

To a solution of 0.8 g (3.03 mmoles) of 18-crown-6 in 100 ml of dry ether was added 3.27 g (29.14 mmoles) of potassium tert-butoxide. The mixture was stirred while a solution of 3.75 g (27.75 mmoles) of 5-fluoroindole in 80 ml of ether was added. The stirring was continued for 0.5 hour. Solid was present. Then 3.69 g (29.15 mmoles) of benzyl chloride in 80 ml of ether was added. The mixture was stirred for 28 hours. Water (100 ml) was added. The layers were separated. The aqueous layer was extracted with 100 ml of ether. The combined ether layers were washed with 50 ml of brine and dried over MgSO$_4$. Evaporation of the solvent left 6.95 g of orange oil. The oil was chromatographed on a 600 g column of silica gel. The column was eluted with 30% CH$_2$Cl$_2$-Skellysolve B and 200 ml fractions were collected. The fractions were assayed by silica gel tlc (1×4") (30% CH$_2$Cl$_1$-Skellysolve B). Fractions 11–15 were combined giving 0.88 g (14%) of 1-benzyl-5-fluoroindole as a pale yellow oil which contained a small amount of 1,3-dibenzyl-5-fluoroindole.

Physical characteristics are as follows:

NMR (CD$_3$OD): δ 5.23 (s, 2H), 6.46 (d, J=4 Hz, 1H), 6.7–7.32 (m, 9H). Also present in the spectrum are two small singlets one at 3.98 and the other at 5.13 δ, which are from the 1,3-dibenzyl-5-fluoroindole impurity.

Fractions 19–29 were combined giving 2.28 g of recovered 5-fluoroindole as a solid.

Preparation 12

N,N-Dimethyl-2-oxoacetamide

To a solution of 5.21 g (25.51 mmoles) of (L)-N,N-dimethyltartramide in 100 ml of MeOH was added 5.82 g (25.53 mmoles) of para-periodic acid. The mixture became warm. The resulting solution was allowed to stand for 24 hours giving a yellow solution. The solvent was evaporated using a rotary evaporator and a water bath at 40° leaving a viscous orange-brown oil. The oil was triturated with 250 ml of ether causing a solid to separate. The mixture was filtered. Evaporation of the solvent from the filtrate left 4.97 g of brown oil. The oil was chromatographed on a 300 g column of silica gel. The column was eluted with 10% MeOH—CH$_2$Cl$_2$ and 100 ml fractions were collected. The fractions were assayed by silica gel tlc (1×4") (10% MeOH-CH$_2$Cl$_2$). Fractions 7–11 were combined giving 4.92 g (95%) of N,N-dimethyl-2-oxoacetamide as a brown oil.

Physical characteristics are as follows:

NMR (CDCl$_3$): δ3.11 (s, 3H), 3.19 (s, 3H), 5.80 (s, 1H), 9.58 (very small s). A MeOH peak was also present. Since the peak at 9.58 δ is so small, the compound must exist in a polymeric form.

Preparation 13

Diethoxyacetamide

A mixture of 24.85 g of ethyl diethoxyacetate and 140 ml of concentrated ammonium hydroxide was stirred for 3 hours. The ammonia and H$_2$O were evaporated under reduced pressure on a water bath at 50°–60° leaving a wet solid. The wet solid was dried in a vacuum oven at 53° for 18 hours giving a dark pink solid. The solid was dissolved in CH$_2$Cl$_2$. The solution was filtered to remove a small amount of red insoluble material. The filtrate was concentrated and Skellysolve B was added. Cooling gave 18.0 g (87%) of diethoxyacetamide as orange plates, m.p. 76.5–79°.

Preparation 14

2-(3-Trifluoromethylphenyl)-Δ-1-Pyrroline

To magnesium metal turnings (2.19 g, 90 mmol) covered with dry ether (40 mL) was added ca. 10% of a solution of 3-trifluoromethylbromobenzene (10.13 g, 45 mmol) in Et$_2$O (10 mL). When the reaction had commenced the remaining halide solution was added at such a rate so as to maintain a gentle reflux. After the addition was complete the brown mixture was heated under reflux for 30 minutes; then was cooled to room temperature and transferred via cannula to a flask (250 mL, three-neck RB) equipped with a reflux condenser and an addition funnel. The Grignard reagent was diluted with Et$_2$O (100 mL) and a solution of freshly distilled 4-chlorobutyronitrile (4.66 g, 45 mmol) in Et$_2$O (50 mL) was added over a period of 20 minutes. The resulting solution was heated under reflux for 30 minutes, then was allowed to cooled to room temperature and stir overnight. The solvent was removed in vacuo and the gummy residue refluxed in o-xylene (100 mL) for one hour, then was allowed to cool to room temperature and was treated with 10% aqueous NH$_4$Cl (100 mL). The organic phase was separated, the aqueous layer was extracted with Et$_2$O (100 mL) and the combined organic phases were acidified to pH 1 with 6N aqueous HCl. The aqueous layer was separated, extracted with Et$_2$O (100 mL) and the pH was adjusted to 14 with 20% aqueous NaOH. The aqueous phase was extracted with Et₂O (2×mL), the combined organic extracts were washed with water (0.25 L), brine (0.25 L), dried (Na₂SO₄) and then concentrated in vacuo to furnish the title compound (3.43 g. 35%) as a brown oil which was utilized without further purification.

Physical characteristics are as follows:

TLC: (Merck; EtOAc-hexane, 1:1; UV (+); ammonium molybdate): rf =0.43.

¹H-NMR (300 MHz, CDCl₃): δ=8.12 (s, 1), 8.01 (d, J=7.8Hz, 1), 7.53(m, 1), 4.10(m, 2), 2.96(m, 2), 2.08(m, 2).

¹³C-NMR (75.5 MHz), CDCl₃): δ=173.2, 136.2, 130.6, 128.8, 126.7, 126.0, 124.2, 122.5, 61.6, 34.8, 22.6.

Preparation 15

2(3-Trifluoromethylphenyl)-pyrrolidine

To a solution of 2(3-trifluoromethylphenyl)pyrroline (3.43 g, 16 mmol) in methanol-THF (100 mL, 1:1, v/v) was added glacial acetic acid (5 mL) followed immediately by NaBH₃CN (1.31 g, 21 mmol). After stirring for two hours at room temperature the reaction mixture was concentrated in vacuo and the resulting rust colored solid was treated with 20% aqueous NaOH (25 mL) to give a rust colored solution and suspended solids. The mixture was cast into water (100 mL) and EtOAc (100 mL). The organic phase was separated, the aqueous layer was extracted with an additional volume (100 mL) of EtOAc, and the combined organic extracts were washed with water (0.25 L), brine (0.25 L) and dried (Na₂SO₄). Concentration in vacuo provided the crude amine as a brown liquid which was purified by chromatography on a column of silica gel (230–400 mesh, 500 g. 70 mm o.d., EtOAc-hexanes 30:70, 400 mL fractions) using the flash technique. Fractions 27–50 afforded 2.56 g (74%) of the title compound as a yellow oil.

Physical characteristics are as follows:

TLC: (Merck: EtOAc-hexanes, 1:1.

UV (+); ammonium molybdate): RF=0.08.

¹H-NMR (300 MHz, CDCl₃): δ=7.39–7.64 (4), 4.18 (t, J=7.7Hz, 1), 3.20 (m, 1), 3.04 (m, 1), 2.20 (m, 1), 2.01 (m, 1), 1.90 (m, 2), 1.6 (m, 1).

¹³C-NMR (75.5MHz, CDCl₃): δ=147.1, 129,9, 128.7, 126.7, 123.5, 123.2, 122.9, 61.9, 46.9, 34.5, 25.5.

Preparation 16

1-Phenyl-1H-indole-3-acetonitrile-α-((3-trifluoromethyl)phenyl)methylamine

To a solution of 3-trifluoromethylbenzylamine (4.38 g, 25 mmol) and NaCN (11.23 g, 25 mmol) in 1.00M aqueous HCl (25 mL) was added one portion N-benzylindole-3-carboxyaldehyde (5.90 g, 25 mmol) in MeOH (25 mL). The mixture was allowed to stir for five hours, then the reaction was cast into Et₂O (1.0 L) and 0.3N aqueous NaOH (1.0 L). The organic phase was separated, washed with brine (1.0 L) and dried (Na₂SO₄). Concentration in vacuo afforded the crude amino-nitrile as an oily red-orange solid which was purified by chromatography on a column of silica gel (230–400 mesh, 500 g, 70 mm o.d., Et₂-O-hexanes 1:4, 300 mL fr) using the flash technique. Fractions 6–12 gave 3.76 g (36%) of 1 as a relatively unstable cream colored solid which was contaminated with the starting aldehyde. This compound was utilized in the next reaction without further purification. Physical characteristics are as follows:

TLC: (Merck: Et₂O-hexanes, 1:1.

UV (+); ammonium molybdate): R$_f$=0.20.

¹H-NMR (300 MHz, CDCl₃): δ=1.94 (brm, 1), 4.09 (dq, J=9.1, 1.6 Jz, 2), 5.04 (d, J=8.7 Hz, 1), 5.29 (s, 2), 7.0–7.8 (14).

IR (nest): 3330, 3050, 2925, 2850, 2210, 1640, 1540, 1440, 1340, 1160 (br), 890, 709, 735 and 695 cm⁻¹.

EI/MS (70 eV): 392 (base), 301 (34.1), 281 (4.35), 248 (10.7), 232 (6.8), 220 (22.6), 208 (85.5), 91 (base).

Data attributed to Kalir, A.; Szara, S.J. Med. Chem. 2966, 9, 793.

Preparation 17

Methyl-3-trifluoromethylphenylacetate

Into a solution of 3-trifluoromethylphenylacetic acid (20.0 g. 98 mmol) in MeOH (100 mL), cooled in an ice-water bath, was bubbled HCl (g) for 15 min. The mixture was allowed to warm to room temperature and was then concentrated in vacuo to furnish a clear, yellow-green liquid which was diluted with EtOAc (0.25L) and washed with saturated aqueous NaHCO₃ (2×0.25L), brine (0.25L), and dried (Na₂SO₄). Concentration in vacuo provided the crude ester which was purified by chromatography on a column of silica gel(2-30–400 mesh, 600 g, 70 mm o.d., ethyl acetate-hexanes 10:90, 400 mL fractions) using the flash technique. Fractions 6–9 provided 19.08 g (89%) of methyl-3-trifluoromethylphenylacetate as a clear colorless liquid.

Physical characteristics are as follows:

TLC (Merck; EtOAc-hexanes, 25:75.

UV(+)) Rf=0.44.

1H-NMR: δ=7.35–7.55 (4), 3.70 (s, 3), 3.67 (s, 2).

Preparation 18

Methyl-2-(3-trifluoromethylphenylacetate)-2-bromo-acetate

To a solution of methyl 3-trifluoromethylphenylacetate (37.79 g, 173 mmol) in CCl₄ (0.3L) was added NBS (33.91 g, 191 mmol) in six portions at one hour intervals. After the first addition of NBS, two drops of 48% HBr were added and the mixture was warmed to reflux and maintained at reflux during the course of the NBS additions and for an additional 18 hours after the additions were completed. The mixture was cooled to room temperature and filtered through a pad of silica gel (230–400 mesh, 250 g, eluted with EtOAc-hexanes, 50:50, 0.75 L). Concentration in vacuo afforded the crude bromide as a clear yellow liquid. The crude product was purified by chromatography on a column of silica gel (230–400 mesh, 600 g, 70 mm o.d., ethyl acetate-hexane 25:75, 400 mL fractions) using the flash technique. Fractions 4–6 provided 39.6 g (771 %) of methyl-2-(3-trifluoromethylphenyl)2-bromo-acetate as a clear colorless liquid.

Physical characteristics are as follows:

TLC (Merck; EtOAc-hexanes, 25:75.

UV(+); ammonium molybdate) Rf=0.45.

1H-NMR: δ=7.40–7.85 (4), 5.38 (s, 1), 3.81 (s, 3).

EI/MS (70 eV): 298 (M+, 1.93), 296 (M+, 2.7), 239 (22.2), 237 (22.2), 217 (base), 189 (36.2), 159 (34.3).

Preparation 19

3-Trifluoromethylphenylglycine Methyl Ester

To a solution of methyl 3-trifluoromethylphenyl-2-bromo-acetate (22.38 g. 75.3 mmol) in CHCl₃ (0.1 L), cooled (0° C. internal, cryo-cool) in a −10° C. methanol bath, was added a solution of tetramethyl guanidiniumazide (13.11 g, 82.9 mmol) in CHCl₃ (0.15 L) over one hour. After the addition was completed the solvent was removed in vacuo (no heat!) to afford a pale yellow solid. The crude yellow material was placed in Et₂O and the dissolved organic materials were separated from the tetramethylguanidinium hydrobromide by filtration through a pad of celite. The filter cake was rinsed with Et₂O (0.2 L) and the combined filtrates were concentrated in vacuo (no heat!) to furnish the desired azide (16.56 g, 85%) as a pale brown oil which was immediately utilized without further purification.

Physical characteristics are as follows:

TLC (Merck; EtOAc-hexanes, 25:75.

UV(+); ammonium molybdate) Rf=0.23.

1H-NMR: $\delta$=8.33 (brs, 1) 8.25 (d, J=8Hz, 1), 7.92 (d, J=8Hz, 1), 7.60–7.70 (1), 5.11 (s, 1), 4.01 (s, 3).

Infrared (neat): 3173, 3150, 2933, 2112, 1752, 1721, 1610, 1452, 1331, 1247, 1207, 1182, 1169, 1126, 1096, 1077, 805, 792, and 700 cm⁻¹.

The crude azide (16.56 g, 63.9 mmol) was dissolved in MeOH (0.1 L) and hydrogenated at 50 psi of H₂ over 10% Pd-C (1.5 g) in a Parr apparatus until hydrogen uptake ceased. The catalyst was removed by filtration through a pad of celite, the filter cake was rinsed with MeOH (0.2L) and the combined filtrates were concentrated in vacuo to give the crude amino acid ester as a an oily semi-solid. This material was partitioned between water (0.5 L) and EtOAc (0.5 L). The organic phase was discarded, the aqueous phase was made basic (20% aqueous NaOH) and extracted with EtOAc (2×0.25 L). The combined organic phases were dried (Na₂SO₄), and concentrated in vacuo to give the crude ester as a pale green oil. The crude product was purified by chromatography on a column of silica gel (230–400 mesh, 500 g, 70 mm o.d., packed-ethyl acetate-hexanes 30:70, eluted ethyl acetate-hexanes 50:50, 400 mL fractions) using the flash technique. Fractions 6–10 provided 9.24 g (53%) of the desired 3-trifluoromethylphenylglycine methyl ester as a clear, colorless liquid.

Physical characteristics are as follows:

TLC (Merck; EtOAc-hexanes, 25:75.

UV(+); ammonium molybdate) Rf=0.10.

1H-NMR: $\delta$=7.69(brs, 1), 7.59 (brt, J=8Hz, 2), 7.47 (d, J=8Hz, 1), 4.70 (s, 1), 3.72 (s, 3), 1.98(s, 2).

Infrared (neat): 3385, 3320, 2958, 1741, 1451, 1438, 1331, 1271, 1223, 1167, 1125, 1097, 1074, 987, 906, 812, 786, and 701 cm⁻¹.

EI/MS (70 eV): 233 (M+, 3.0), 174 (base), 127 (9.3).

Analysis: Calcd. for $C_{10}H_{21}Fe_3NO_2$: C, 51.51; H, 4.32; N, 6.01. Found: C, 51.74; H, 4.35, N, 6.08.

EXAMPLE 1

α-[-(Trifluoromethyl)benzylamino]-1]benzylindole-3-acetic acid

To a stirred solution of 5.52 g (0.06 mole) of glyoxylic acid monohydrate in 150 mL of MeOH was added 10.36 g (0.05 mole) of 1-benzylindole. To the resulting solution was added a solution of 8.76 g (0.05 mole) of 3-(Trifluoromethyl)benzylamine in 50 mL of MeOH and 1 mL of acetic acid. The mixture was stirred for 20 hours. The solid which had separated was collected by filtration and washed with MeOH giving 16.97 g (77%) of the title compound as an ivory solid, m.p. 171°–172.5° (dec.).

Physical characteristics are as follows:

Analysis: Calcd. for $C_{25}H_{21}F_3N_2O_2$: C, 68.48; H, 4.83; N, 6.39. Found: C, 68.61; H, 4.75; N, 6.40.

Mass Spectrum: Ions at (m/e): 393, 392, 208, 174, 159, 91, 69, 65, 57, 55.

Infrared: νmax (mull) 3106, 3061, 3030, 2519, 2396, 2345, 2252, 1637, 1608, 1541, 1497, 1389, 1360, 1333, 1288, 1246, 1210, 1184, 1116, 1079, 908, 802, 743, 729, 703 cm⁻¹.

Utilizing a procedure similar to that of Example 1 but substituting the appropriately substituted indole and amine for 1-benzylindole and 3-(trifluoromethyl)benzylamine, there are obtained the following compounds:

α-[3-(Trifluoromethyl)benzylamino]-1-methylindole-3-acetic acid as a white solid, m.p. 163° (dec.).

Physical characteristics are as follows:

Analysis: Calcd. for $C_{19}H_{17}F_3N_2O_2$: 62.98; H, 4.73; N, 7.73. Found: C, 62.73; H, 4.53; N, 7.70.

Mass Spectrum: Ions at (m/e): 317, 159, 158, 157, 145, 144, 132, 127, 109, 77.

NMR (DMSO-d₆): δ3.74 (s, 3H), 3.94 (s, 2H), 4.58 (s, 1H), 6.9–7.88 (br m, 9H).

Infrared: νmax (mull) 3117, 3070, 3057, 3025, 2368, 2300, 2225, 2165, 1598, 1549, 1395, 1371, 1356, 1331, 1256, 1205, 1179, 1133, 1121, 1075, 910, 814, 806, 772, 742, 734, 706 cm⁻¹.

α-Benzylamino-1-benzylindole-3-acetic Acid as a white solid. m.p. 180° (dec.).

Physical characteristics are as follows:

Analysis: Calcd. for $C_{24}H_{22}N_2O_2$: C, 77.81; H, 5.99; N, 7.56. Found: C, 77.87; H, 6.04; N, 7.54.

Mass Spectrum: Ions at (m/e): 326, 325, 324, 235, 220, 107, 106, 92, 91, 65.

Infrared: νmax (mull) 3103, 3088, 3079, 3066, 3045, 3035, 2356, 2447, 2384, 2258, 2197, 1636, 1609, 1542, 1496, 1353, 1294, 1248, 741, 734, 695 cm⁻¹.

α-(4-Chlorobenzylamino)-1-benzylindole-3-acetic acid as a pale pink solid, m.p. 171° (dec.).

Physical characteristics are as follows:

Analysis: Calcd. for $C_{24}H_{21}ClN_2O_2$: C, 71.19; H, 5.23; Cl, 8.76; N, 6.92. Found: C, 71.16; H, 5.28; Cl, 8.80; N, 6.99.

Mass Spectrum: Ions at (m/e): 360, 359, 235, 220, 140, 127, 125, 106, 91, 77.

Infrared: νmax (mull) 3110, 3100, 3064, 3032, 2670, 2567, 2370, 1634, 1597, 1539, 1493, 1375, 1368, 1353, 1301, 804, 743 cm⁻¹.

α-[(3-Pyridinylmethyl)amino]-1-benzylindole-3-acetic acid as a pale orange solid, m.p. 183° (dec).

Physical characteristics are as follows:

Analysis: Calcd. for $C_{23}H_{21}N_3O_2$: C, 74.37; H, 5.70; N, 11.31.

Mass Spectrum: Ions at (m/e): 327, 326, 325, 235, 221, 220, 92, 91, 90, 65.

Infrared: νmax (mull) 3108, 3088, 3063, 3051, 3029, 2668, 2642, 2380, 2327, 2282, 1614, 1607, 1578, 1544, 1495, 1479, 1466, 1456, 1360, 1346, 802, 762, 750, 735, 697, cm⁻¹.

α-[(3-Phenylpropyl)amino]-1-benzylindole-3-acetic acid as a white solid, m.p. 178° (dec).

Physical characteristics are as follows:

Analysis: Calcd. for $C_{26}H_{26}N_2O_2$: C, 78.36; H, 6.58; N, 7.03. Found: C, 78.66; H, 6.61; N, 7.19.

Mass Spectrum: Ions at (m/e): 354, 353, 248, 235, 221, 220, 118, 92, 91, 65.

Infrared: νmax (mull) 3109, 3085, 3056, 3029, 2788, 2763, 2664, 2588, 2543, 2429, 1627, 1605, 1544, 1495, 1483, 1399, 1367, 742, 716, 701 cm⁻¹.

α-(4-Methoxybenzylamino)-1-benzylindole-3-acetic acid as a white solid, m.p. 170° (dec.)
Physical characteristics are as follows:
Analysis: Calcd. for C$_{25}$H$_{24}$N$_2$O$_3$: C, 74.98; H, 6.04: N, 7.00. Found: C, 75.17; H, 6.22; N, 6.95.
Mass Spectrum: Ions at (m/e): 355, 235, 221, 220, 137, 136, 121, 106, 91, 77.
Infrared: νmax (mull) 3102, 3089, 3061, 2590, 2398, 1639, 1612. 1592, 1585, 1538, 1518, 1496, 1480, 1377, 1311, 1252, 1187, 1174, 1031, 1015, 823, 815, 743 cm$^{-1}$.

α-Morpholino-1-benzylindole-3-acetic acid as a white solid, m.p. 202° (dec).
Physical characteristics are as follows:
Analysis: Calcd. for C$_{21}$H$_{22}$N$_2$O$_3$: C, 71.98; H, 6.33; N, 8.00. Found: C, 72.05; H, 6.43; N, 8.13.
Mass Spectrum: Ions at (m/e): 306, 305, 265, 264, 248, 220, 91, 69, 57, 55.
Infrared: νmax (mull) 3121, 3101, 3090, 3069, 3033, 3024, 2118, 1614, 1587, 1546, 1497, 1485, 1344, 1251, 1172, 1124, 1087, 753, cm$^{-1}$.

α-[(4-Phenylbutyl)amino]-1-benzylindole-3-acetic acid as an ivory solid, m.p. 171° (dec).
Physical characteristics are as follows:
Analysis: Calcd. for C$_{27}$H$_{28}$N$_2$O$_2$: C, 78.61; H, 6.84; N, 6.79. Found: C, 78.02; H, 7.08; N, 6.66.
Mass Spectrum: Ions at (m/e): 368, 335, 221, 220, 149, 129, 104, 92, 91, 77, 65, 57.
Infrared: νmax (mull) 3106, 3084, 3060, 3025, 2810, 2772, 2700, 2591, 2446, 1605, 1542, 1496, 1394, 1383, 1379, 1365, 783, 759, 740, 721, 699 cm$^{-1}$.

α-Methylamino-1-benzylindole-3-acetic Acid as a pale pink solid. m.p. 159° (dec).
Physical characteristics are as follows:
Analysis: Calcd. for C$_{18}$H$_{18}$N$_2$O$_2$: C, 73.45; H, 6.16; N, 9.52. Found: C, 73.45; H, 6.25; N, 9.25.
Mass Spectrum: Ions at (m/e): 250, 249, 235, 220, 158, 130, 129, 92, 91, 65.
Infrared: νmax (mull) 3111, 3072, 3034, 3020, 1615, 1606, 1574, 1550, 1497, 1384, 1355, 742, 727, 717 cm$^{-1}$.

α-[3-(Trifluoromethyl)benzylamino]-1-(4-chlorobenzyl)indole-3-acetic acid as an ivory solid, m.p. 186° (dec).
Physical characteristics are as follows:
Analysis: Calcd. for C$_{25}$H$_{20}$ClF$_3$N$_2$O$_2$: C, 63.49; H, 4.26; Cl, 7.50 ; N, 5.93. Found: C, 63.62; H, 4.55; Cl, 7.39; N, 5.91.
Mass Spectrum: Ions at (m/e): 429, 428, 427, 426, 269, 254, 174, 159, 127, 125.
Infrared: νmax (mull) 3061, 3036, 2511, 2495, 2395, 2242, 1637, 1608, 1542, 1492, 1389, 1358, 1335, 1290, 1247, 1211, 1166, 1118, 1078, 1015, 908, 813, 802, 77, 744, 729, 701 cm$^{-1}$.

α-[3-(Trifluoromethyl)benzylamino]-1-phenylindole-3-acetic acid as a white solid, m.p. 172° (dec).
Physical characteristics are as follows:
Analysis: Calcd. for C$_{24}$H$_{19}$F$_3$N$_2$O$_2$: C, 67.92; H, 4.51; N, 6.60. Found: C, 67.92; H, 4.70; N, 6.49.
Mass Spectrum: Ions at (m/e): 380, 379, 221, 220, 219, 206, 194, 193, 159, 77.
Infrared: νmax (mull) 3120, 3062, 3047, 2644, 2529, 2341, 2195, 2122, 2091, 1641 sh, 1613, 1597, 1575, 1557, 1502, 1362, 1330, 1203, 1174, 1128, 1077, 877, 808, 773, 769, 755, 748, 743, 697 cm$^{-1}$.

α-[(2-Phenylethyl)amino[-1-benzylindole-3-acetic acid hydrate (1:1) as a white solid, m.p. 163° (dec).
Physical characteristics are as follows:
Analysis: Calcd. for C$_{25}$H$_{24}$N$_2$O$_2$.H$_2$O; C, 74.60; H, 6.51; N, 6.96. Found: C, 74.50; H, 6.14; N, 6.75.
Mass Spectrum: Ions at (m/e): 340, 335, 247, 221, 220, 92, 91, 65.
NMR (DMSO-d$_6$): δ2.9 (s, 4H), 4.72 (s, 1H), 5.38 (s, 2H), 6.9-7.92 (m, 15H).
Infrared: νmax (mull) 3596, 3511, 3246, 3340, 3106, 3057, 3031, 3026, 2730, 2608, 2519, 2425, 1621, 1582, 1604, 1540, 1419, 1483, 1378, 1351, 1340, 1176, 1169, 751, 747, 739, 727, 702 cm$^{-1}$.

α-[3-(Trifluoromethyl)benzylamino]-1-benzyl-2-phenylindole-3-acetic Acid as a white solid, m.p. 186° (dec).
Physical characteristics are as follows:
Analysis: Calcd. for C$_{31}$H$_{25}$F$_3$N$_2$O$_2$: C, 72.36; H, 4.90; N, 5.45. Found: C, 72.67; H, 5.06; N, 5.30.
Mass Spectrum: Ions at (m/e): 469, 312, 311, 309, 219, 218, 204, 159, 92, 91.
NMR (DMSO-d$_6$): δ3.9 (s, 2H), 4.3 (s, 1H), 5.3 (s, 2H), 5.8 (s, 1H), 6.8-7.7 (m, 17H), 7.9-8.1 (m, 1H).
Infrared: νmax (mull) 3064, 3049, 3035, 3027, 2669, 2529, 2337, 1642, 1563, 1495, 1335, 1165, 1127, 1075, 806, 762, 659, 740, 714, 704, 696 cm$^{-1}$.

α-[(2-(4-Aminosulfonylphenyl)ethyl)amino[-1-benzylindole-3-acetic acid hydrate (2:1) as a buff solid, m.. 20° (dec).
Physical characteristics are as follows:
Analysis: Calcd. for C$_{25}$H$_{25}$N$_3$O$_4$SO5.H$_2$O: C, 63.53; H, 5.55; N, 8.89; S, 6.79. Found: C, 63.67; H, 5.48; N, 9.03; S, 7.10.
Mass Spectrum: Ions at (m/e): 427, 426, 425, 335, 247, 220, 92, 91, 90, 57.
Infrared: νmax (mull) 3369, 3211, 3129, 3082, 3054, 3035, 3024, 2689, 2636, 2609, 2340, 2200, 1614, 1574, 1554, 1497, 1482, 1386, 1377, 1352, 1333, 1315, 1169, 1161, 855, 821, 750, 741, 730, 694 cm$^{-1}$.

α-[3-(trifluoromethyl)benzylamino[-1-benzyl-5-methoxyindole-3-acetic acid as a white solid, m.p. 168° (dec).
Physical characteristics are as follows:
Analysis: Calcd. for C$_{26}$H$_{23}$F$_3$N$_2$O$_3$: C, 66.66; H, 4.95; N, 5.98. Found: C, 66.61; H, 5.00; N, 6.13.
Mass Spectrum: Ions at (m/e): 424, 422, 251, 150, 160, 159, 92, 91, 65.
Infrared: νmax (mull) 3112, 3059, 3028, 2504, 2397, 2322, 1605, 1540, 1487, 1389, 1376, 1358, 1332, 1252, 1230, 1204, 1171, 1123, 1076, 826, 813, 799, 734, 705 cm$^{-1}$.

α-(N-Methyl-benzylamino)-1-benzylindole-3-acetic acid hydrate (4:1) as a white solid, m.p. 117° (dec).
Physical characteristics are as follows:
Analysis: Calcd. for C$_{25}$H$_{24}$N$_2$O$_2$.0.025H$_2$O: C, 77.19; H, 6.35; N, 7.20. Found: C, 77.30; H, 6.27; N, 7.10.
Mass Spectrum: Ions at (m/e): 340, 339, 249, 220, 134, 121, 92, 91, 65.
NMR (DMSO-d$_6$): δ2.2 (s, 3H), 3.7 (d, J=3Hz, 2H), 4.65 (s, 1H), 5.45 (s, 2H), 7.05-7.7 (m, 14H), 7.78-7.98 (m, 1H).
Infrared: νmax (mull) 3644, 3370, 3111, 3056, 3028, 2680, 1622, 1543, 1496, 1366, 1341, 1331, 1179, 907, 747, 723, 699 cm$^{-1}$.

α-[3-(Trifluoromethyl)benzylamino]-1-benzyl-5-chloroindole-3-acetic acid as a white solid, m.p. 192° (dec).
Physical characteristics are as follows:
Analysis: Calcd. for C$_{25}$H$_{20}$ClF$_3$N$_2$O$_2$: C, 63.49; H, 4.26; Cl, 7.50; N, 5.93. Found: C, 63.36; H, 4.45; Cl, 7.24; N, 5.86.
Mass Spectrum: Ions at (m/e): 473 (m+), 427, 301, 300, 299, 298, 269, 159, 103, 91.

Infrared: νmax (mull) 3112, 2102, 3066, 3028, 2513, 2407, 2368, 2248, 1637, 1607, 1540, 1497, 1336, 1290, 1246, 1212, 1168, 1122, 1114, 1079, 909, 859, 800, 734, 728, 702 cm$^{-1}$.

α-[3-(trifluoromethyl)benzylamino]-1-allylindole-3-acetic acid as a very pale orange solid, m.p. 163° (dec).
Physical characteristics are as follows:
Analysis: Calcd. for $C_{21}H_{19}F_3N_2O_2$: C, 64.94; H, 4.93; N, 7.21. Found: C, 65.22; H, 4.85; N, 6.94.
Mass Spectrum: Ions at (m/e): 388 (M+), 344, 343, 185, 183, 174, 170, 159, 158, 156, 106.
Infrared: νmax (mull) 3118, 3081, 3058, 2484, 2387, 2337, 2236, 1641, 1599, 1541, 1388, 13959, 1335, 1289, 1240, 1210, 1176, 1118, 1080, 908, 803, 738, 701 cm$^{-1}$.

α-[2-(Trifluoromethyl)benzylamino[-1-benzylindole-3-acetic acid as a white solid, m.p. 180° (dec).
Physical characteristics are as follows:
Analysis: Calcd. for $C_{25}H_{21}F_3N_2O_2$: C, 68.48; H, 4.83; H, 4.83; N, 6.39.
Found: C, 68.08; H, 4.81; N, 6.43.
Mass Spectrum: Ions at (m/e): 393, 392, 235, 175, 174, 159, 134, 106, 91, 57.
Infrared: νmax (mull) 3129, 3085, 3071, 3064, 3054, 3032, 2773, 2623, 2424, 1612, 1598, 1573, 1496, 1317, 1175, 1163, 1124, 1033, 771, 742, 736, 696 cm$^{-1}$.

α-[4-(Trifluoromethyl)benzylamino]-1-benzylindole-3-acetic acid as a pale orange solid, m.p. 170° (dec).
Physical characteristics are as follows:
Analysis: Calcd. for $C_{24}H_{21}F_3N_2O_2$: C, 68.48; H, 4.83; N, 6.39. Found: c, 68.09; H, 4.79; N, 6.19.
Mass Spectrum: Ions at (m/e): 394, 393, 392, 235, 221, 220, 208, 174, 159, 91.
Infrared: νmax (mull) 3089, 3065, 3029, 2539, 2496, 2401, 2247, 1636, 1607, 1542, 1497, 1356, 1327, 1248, 1170, 1125, 1070, 893, 825, 779, 745, 734, 727, 695 cm$^{-1}$.

α-(3-Chlorobenzylamino)-1-benzylindole-3-acetic acid as a pale orange solid, m.p. 162° (dec).
Physical characteristics are as follows:
Analysis: Calcd. for $C_{24}H_{21}ClN_2O_2$: C, 71.19; H, 5.23; Cl, 8.76; N, 6.92. Found: C, 71.39; H, 5.13; Cl, 8.61; N, 6.67.
Mass Spectrum: Ions at (m/e): 407, 405, 359, 266, 265, 264, 236, 235, 125, 91.
Infrared: νmax (mull) 3120, 3065, 3055, 3030, 2608, 2526, 2476, 2405, 2316, 2266, 2153, 1596, 1545, 1496, 1388, 1362, 1249, 900, 846, 797, 738, 705 cm$^{-1}$.

α-(2-Chlorobenzylamino)-1-benzylindole-3-acetic acid as a white solid, m.p. 164° (dec).
Physical characteristics are as follows:
Analysis; Calcd. for $C_{24}H_{21}ClN_2O_2$: C, 71.19; H, 5.23; Cl, 8.76; N, 6.92. Found: C, 71.00; H, 5.26; Cl, 8.73; N, 6.88.
Mass Spectrum: Ions at (m/e): 405, 359, 266, 265, 264, 236, 235, 125, 91, 45.
Infrared: νmax (mull) 3061, 3049, 3030, 2730, 2601, 2411, 1629, 1592, 1542, 1497, 1378, 1367, 1313, 1178, 770, 759, 744, 700 cm$^{-1}$.

α-[3,5-Bis(trifluoromethyl)benzylamino]-1-benzylindole-3-acetic acid as a white solid, m.p. 170° (dec).
Physical characteristics are as follows:
Analysis: Calcd. for $C_{26}H_{20}F_6N_2O_2$: C. 61.66; H, 3.98; H, 5.53. Found: C, 61.79; H, 3.97; N, 5.60.
Mass Spectrum: Ions at (m/e): 505, 462, 461, 398, 265, 264, 244, 236, 235, 227, 91.
Infrared; νmax (mull) 3115, 3092, 3066, 3035, 2317, 2146, 1607, 1541, 1497, 1359, 1285, 1180, 1137, 908, 738, 683 cm$^{-1}$.

α-(4-Methylbenzylamino)-1-benzylindole-3-acetic acid as a white solid, m.p. 170° (dec).
Physical characteristics are as follows:
Analysis: Calcd. for $C_{25}H_{24}H_2O_2$: C, 78.10; H, 6.29; N. 7.29. Found: C, 77.91; H, 6.30; N, 7.30.
Mass Spectrum: Ions at (m/e): 386, 385, 340, 339, 265, 264, 236, 235, 105, 91.
Infrared: νmax (mull) 3115, 3061, 3024, 2608, 2529, 2467, 2391, 2313, 2161, 1604, 1598, 1545, 1519, 1495, 1364, 1253, 891, 815, 808, 744, 735, 699 cm$^{-1}$.

α-[(2-Furylmethyl)amino]-1-benzylindole-3-acetic acid as a white solid, m.p. 172° (dec).
Physical characteristic are as follows:
Analysis: Calcd. for $C_{22}H_{20}N_2O_3$: C, 73.31; H, 5.59; N, 7.77. Found: C, 73.38; H, 5.85; N. 7.80.
Mass Spectrum: Ions at (m/e): 361, 315, 266, 265, 264, 236, 235, 91, 81, 45.
Infrared, νmax (mull) 3124, 3101, 3063, 3046, 3030, 2507, 2386, 2248, 1629, 1606, 1544, 1497, 1376, 1354, 1337, 1267, 1174, 1149, 1015, 930, 737, 695 cm$^{-1}$.

α-[(2-Thienylmethyl)amino]-1-benzylindole-3-acetic acid as a white solid, m.p. 181° (dec).
Physical characteristics are as follows:
Analysis: Calcd. for $C_{22}H_{20}N_2O_2S$: C, 70.18; H, 5.36; N, 7.44; S, 8.52. Found: C, 70.06; H, 5.44; N, 7.52; S, 8.51.
Mass Spectrum: Ions at (m/e): 378, 377, 331, 265, 264, 235, 217, 97, 91, 45.
Infrared: νmax (mull) 3103, 3064, 3044, 3030, 2535, 2403, 1631, 1606, 1544, 1496, 1363, 1354, 1337, 1330, 747, 736, 703, 695 cm$^{-1}$.

α-(3-Methylbenzylamino)-1-benzylindole-3-acetic acid as a white solid, m.p. 166° (dec).
Physical characteristics are as follows:
Analysis: Calcd. for $C_{25}H_{24}N_2O_2$: C, 78.10; H, 6.29; N, 7.29. Found: C, 78.36; H, 6.52; N, 7.24.
Mass Spectrum: Ions at (m/e): 386, 385, 339, 266, 265, 264, 236. 235, 105, 91.
Infrared: νmax (mull) 3118, 3054, 3026, 2605, 2522, 2476, 2422, 2361, 2317, 2267, 2151, 1604, 1598, 1545, 1496, 1387, 1361, 1253, 797, 738, 726, 707, 701 cm$^{-1}$.

α-(3,4-Dichlorobenzylamino)-1-benzylindole-3-acetic acid as an ivory solid, m.p. 180° (dec).
Physical characteristics are as follows:
Analysis: Calcd. for $C_{24}H_{20}Cl_2N_2O_2$: C, 65.61; H, 4.59; Cl, 16.14; N, 6.38. Found: C, 65.86; H, 4.46; Cl, 15.90; N, 6.46.
Mass Spectrum: Ions at (m/e): 439, 395, 393, 266, 265, 264, 236, 235, 231, 91.
Infrared: νmax (mull) 3091, 3061, 3030, 2502, 2388, 2251, 1636, 1606, 1540, 1497, 1378, 1356, 1310, 1279, 1244, 1213, 902, 821, 778, 744, 728, 692 cm$^{-1}$.

α-(Tetrahydrofurfurylamino)-1-benzylindole-3-acetic acid as a pole pink solid, m.p. 170° (dec).
Physical characteristics are as follows:
Analysis: Calcd. for $C_{22}H_{24}N_2O_3$: C, 72.50; H, 6.64; N, 7.69. Found: C, 72.68; H, 6.35; N, 7.39.
Mass Spectrum: Ions at (m/e): 319, 247, 235, 220, 91, 71, 69, 65, 57. 55.
Infrared: νmax (mull) 3117, 3087, 3061, 3050, 3033, 3024, 2696, 2630, 2552, 2264, 1625, 1579, 1538, 1496, 1356, 1339, 1266, 1173, 1089, 1038, 763, 748, 696 cm$^{-1}$.

α-(3-Fluorobenzylamino)-1-benzylindole-3-acetic acid as a white solid, m.p. 164° (dec).
Physical characteristics are as follows:
Analysis: Calcd. for $C_{24}H_{21}FN_2O_2$: C, 74.21; H, 5.45; N, 7.21. Found: C, 74.17; H, 5.40; N, 7.15.

Mass Spectrum: Ions at (m/e): 344, 343, 342, 235, 221, 220, 208, 124, 109, 91.

Infrared: νmax (mull) 3120, 3058, 3031, 2607, 2522, 2478, 2387, 2324, 1605, 1595, 1544, 1495, 1387, 1363, 1251, 801, 737, 701, 697 cm$^{-1}$.

α-(4-Fluorobenzylamino)-1-benzylindole-3-acetic acid as a white solid, m.p. 185° (dec).

Physical characteristics are as follows:

Analysis: Calcd. for $C_{24}H_{21}FN_2O_2$: C, 74.21; H, 5.45; N. 7.21. Found: C, 73.96; H, 5.27; N. 7.19.

Mass Spectrum: Ions at (m/e): 343, 342, 235, 220, 124, 109, 92, 91, 65.

Infrared: νmax (mull) 3091, 3071, 3058, 3050, 3031, 2534, 2491, 2394, 2335, 2268, 2170, 1634, 1608, 1603, 1542, 1515, 1497, 1355, 1337, 1308, 1288, 1247, 1224, 1209, 890, 826, 778, 747, 735, 724, 697 cm$^{-1}$.

α-(3-Methoxybenzylamino)-1-benzylindole-3-acetic acid as a white solid, m.p. 174° (dec).

Physical characteristics are as follows:

Analysis: Calcd. for $C_{25}H_{24}H_4N_2O_3$: C, 74.98; H, 6.04; N, 7.00. Found: C, 74.92: N, 6.11; N, 6.91.

Mass Spectrum: Ions at (m/e): 355, 354, 235, 221, 220, 136, 122, 121, 91, 65.

Infrared: νmax (mull) 3106, 3087, 3059, 2609, 2526, 2472, 2416, 2362, 1607, 1598, 1588, 1542, 1490, 1386, 1362, 1299, 1260, 1178, 1155, 1036, 898, 780, 749, 738, 701, cm$^{-1}$.

α-[3-(Trifluoromethyl)benzylamino)-1-benzyl-5-methylindole-3-acetic acid as a pink solid, m.p. 180° (dec).

Physical characteristics are as follows:

Analysis: Calcd. for $C_{26}H_{23}F_3N_2O_2$: C, 69.01; H, 5.12; N, 6.19. Found: C, 68.94; H, 5.09; N, 6.20.

Mass Spectrum: Ions at (m/e): 453, 451, 407, 278, 249, 234, 159, 91.

Infrared; νmax (mull) 3122, 3088, 3063, 3028, 2607, 2532, 2500, 2426, 2394, 2324, 2222, 2152, 1593, 1542, 1497, 1487, 1389, 1332, 1253, 1203, 1175, 1123, 1076, 813, 791, 736, 707 cm$^{-1}$.

α-[3-(Trifluoromethyl)benzylamino]-1-benzyl-5-fluoroindole-3-acetic acid as an ivory solid, m.p. 183° (dec).

Physical characteristics are as follows:

Analysis: Calcd. for $C_{25}H_{20}F_4N_2O_2$: C, 65.78; H, 442; N, 6.14. Found: C, 65.98; H, 4.54; N, 5.98.

Mass Spectrum: Ions at (m/e): 457, 411, 309, 284, 283, 282, 253, 231, 159, 91.

Infrared: νmax (mull) 3109, 3033, 2543, 2395, 2256, 1637, 1609, 1579, 1541, 1497, 1486, 1335, 1287, 1246, 1209, 1178, 1166, 1121, 901, 852, 801, 728, 701 cm$^{-1}$.

α-(Benzylamino)-indole-3-acetic acid as a white solid, m.p. 195° (dec).

Physical characteristics are as follows:

Analysis: Calcd. for $C_{17}H_{16}N_2O_2$: C, 72.83; H, 5.75; N, 10.00. Found: C, 73.12; H, 5.97; N, 10.12.

Mass Spectrum: Ions at (m/e): 235, 173, 145, 117, 107, 106, 91, 79, 77, 51.

Infrared: νmax (mull) 3183, 3109, 3034, 2648, 2569, 2495, 2446, 1630, 1619, 1556, 1540, 1498, 1377, 1343, 1230, 755, 738, 697 cm$^{-1}$.

α-(Diphenylmethylamino)-1benzylindole-3-acetic acid hydrate (1:0:7)as a white solid, m.p. 123° (dec).

Physical characteristics are as follows:

Analysis: Calcd. for $C_{30}H_{26}N_2O_2 \cdot 0.7H_2O$: C, 78.47; H, 6.02; N, 6.10. Found: C, 78.902; H, 6.52; N, 6.33.

Mass Spectrum: Ions at (m/e): 400, 183, 167, 165, 120, 106, 105, 104, 91, 77.

Infrared: νmax (mull) 3636, 3250, 3107, 3087, 3064, 2718, 2664, 2645, 2523, 22442, 2341, 1700 w, sh, 1640, 1613, 1605, 1587, 1547, 1493, 1359, 1348, 747, 741, 735, 715, 696 cm$^{-1}$.

α-[(2-Furylmethyl)amino]indole-3-acetic acid as a yellow solid, m.p. 149° (dec).

Physical characteristics are as follows:

Analysis: Calcd. for $C_{15}H_{14}N_2O_3$: C, 66.65; H, 5.22; N, 10.37. Found: C, 66.26; H, 5.30; H, 10.39.

Mass Spectrum: Ions at (m/e): 225, 130, 97, 96, 81, 71, 69, 57, 55, 53.

Infrared: νmax (mull) 3179, 3108, 3074, 3055, 3033, ~2607, 2320, ~2191, 1641, 1578, 1539, 1500, 1492, 1349, 1292, 1034, 771, 751 cm$^{-1}$.

α-[4-(Methoxycarbonyl)benzylamino]-1-benzylindole-3-acetic acid as an ivory solid, m.p. 183° (dec).

Physical characteristics are as follows:

Analysis: Calcd. for $C_{26}H_{24}N_2O_4$: C, 72.88; H, 5.65; N, 6.54. Found: C, 72.58; H, 5.57; N, 6.76.

Mass Spectrum: Ions at (m/e): 429, 383, 266, 265, 264, 236, 235, 149, 91, 18.

Infrared: νmax (mull) 3343, 3108, 3090, 3069, 2952, 2918, 2869, 2855, 1729, 1718, 1630, 1614, 1598, 1459, 1437, 1429, 1417, 1375, 1370, 1360, 1315, 1296, 1282, 1170, 1111, 1017, 758, 744 cm$^{-1}$.

α-[3-(trifluoromethyl)benzylamino]-1-benzyl-5-methoxy-6-methyl-indole-3-acetic acid, m.p. 176° C.

Physical characteristics are as follows:

Analysis: Calcd. for $C_{27}H_{25}F_3N_2O_3$: C, 67.21; H, 5.22; N, 5.81. Found: C, 67.00; H, 5.39; N, 5.70.

α-[3-(Trifluoromethyl)benzylamino]-1-benzyl-5,6-methylenedioxyindole-3-acetic acid, 178°–180° C.

Physical characteristics are as follows:

Analysis: Calcd. for $C_{26}H_{21}F_3N_2O_4$: C, 64.73; H, 4.39; N, 5.81. Found: C, 64.51; H, 4.61; N, 6.03.

α-[3-(Trifluoromethyl)benzylamino]-1-benzyl-5-methoxy-6-isopropylindole-3-acetic acid, m.p. 166° C.

Physical characteristics are as follows:

Analysis: Calcd. for $C_{29}H_{29}F_3N_2O_3$: C, 68.22; H, 5.73; N, 5.49. Found: C, 68.07; H, 5.46; N, 5.61.

α-[3-(Trifluoromethyl)benzylamino]-1-benzyl-5-methoxy-4-methylindole-3-acetic acid, m.p. 154°–155° C.

Physical characteristics are as follows:

Analysis: Calcd. for $C_{27}H_{25}F_3N_2O_3$: C, 67.21; H, 5.22; N, 5.81. Found: c, 66.90; H, 5.09; N, 5.95.

α-[3-(Trifluoromethyl)benzylamino]-1-benzyl-5-methoxy-6-chloroindole-3-acetic acid, m.p. 160.5°–161° C.

Physical characteristics are as follows:

Analysis: Calcd. for $C_{26}H_{22}ClF_3N_2O_3$: 503.1349 (M$^+$+H). Found: 503.1335.

α-[3-(Trifluoromethyl)benzylamino]-1-benzyl-6-methylindole-3-acetic acid, m.p. 182.5°–184.5° C. (dec).

Physical characteristics are as follows:

Analysis: Calcd. for $C_{26}H_{23}F_3N_2O_2$: C, 69.02; H, 5.12; N, 6.19. Found: C, 68.72; H, 5.25; N, 6.07.

α-[3-(Trifluoromethyl)benzylamino]-1-benzyl-5,6-dimethoxyindole-3-acetic acid, m.p. 157°–158° C.

Physical characteristics are as follows:

Analysis: Calcd. for $C_{27}H_{35}F_3N_2O_4$: 498.1766. Found: 498.1743.

α-[3-(Trifluoromethyl)benzylamino]-1-benzyl-5-methoxy-7-methylindole-3-acetic acid, m.p. 170°–171° C.

Physical characteristics are as follows:

Analysis: Calcd. for $C_{27}H_{25}F_3N_2O_3$: C, 67.21; H, 5.22; N, 5.81. Found: C, 67.88; H, 5.51; N, 5.93.

α-[3-(Trifluoromethyl)benzylamino]-1-[(2-diethylamino)ethyl]-indole-3-acetic acid, j.p. 135.5°137° C.

Physical characteristics are as follows:

Analysis: Calcd. for $C_{24}H_{28}F_3N_3O_2$: C, 64.41; H, 6.31; N, 9.39. Found: C, 64.15; H, 6.33; N, 9.33.

α-[3-(Trifluoromethyl)benzylamino[-1,2-diphenylindole-3-acetic acid, m.p. 209° C. (dec).

Physical characteristics are as follows:

Analysis: Calcd. for $C_{30}H_{23}F_3N_2O_2$: C, 71.99; H, 4.63; N, 5.61. Found: C, 71.99; H, 4.97; N, 5.72.

α-[3-(Trifluoromethyl)benzylamino]-1-benzyl-6-methoxyindole-3-acetic acid, m.p. 190°-191° C.

Physical characteristics are as follows:

Analysis: Calcd. for $C_{26}H_{23}F_3N_2O_3$: C, 66.67; H, 4.91; N, 5.98. Found: C, 66.69; N, 5.08; N, 5.90.

α-[3-(Trifluoromethyl)benzylamino]-1-benzyl-5-acetoxyindole-3-acetic acid, m.p. 187°-188° C. (dec).

Physical characteristics are as follows:

Analysis: Calcd. for $C_{27}H_{23}F_3N_2O_4$: C, 65.32; H, 4.64; N, 5.65. Found: C, 65.08; H, 4.57; N, 5.66.

α-[3-(Trifluoromethyl)benzylamino]-1-benzyl-5-hydroxyindole-3-acetic acid, m.p. 190° C. (dec).

Physical characteristics are as follows:

Analysis: Calcd. for $C_{25}H_{21}F_3N_2O$: C, 66.08; H, 4.63; N, 6.17. Found: C, 66.57; H, 5.03; N, 6.48.

α-[3-(Trifluoromethyl)benzylamino]-1-benzyl-5-ethoxyindole-3-acetic acid, m.p. 171°-172° C.

Physical characteristics are as follows:

Analysis: Calcd. for $C_{27}H_{25}F_3N_2O_3$: C, 67.22; H, 5.19; N, 5.81. Found: C, 66.76; H, 5.44; N, 6.27.

α-[3-(Trifluoromethyl)benzylamino]-1-benzyl-5-benzyloxyindole-3-acetic acid, m.p. 173°-174° C.

Physical characteristics are as follows:

Analysis: Calcd. for $C_{32}H_{27}F_3N_2O_3$: C, 70.59; H, 4.96; N, 5.15, Found: C, 70.44; H, 5.27; N, 5.74.

EXAMPLE 2

α-[3-(Trifluoromethyl)-benzylamino]-1-benzylindole-3-acetic Acid Hydrochloride.

A 2.0 G portion of α-[3-(trifluoromethyl)benzylamino]-1-benzylamino]-1-benzylindole 3-acetic acid was added to 150 ml of THF containing an excess anhydrous hydrogen chloride. Witna a few minutes a pink solution was obtained. The solvent was evaporated leaving a pink glassy solid. The solid was crystallized from acetone-hexane giving a pale pink solid which after drying at 66° in a vacuum oven for 22 hours became pale yellow. The solid was crystallized from EtOH-hexane giving 1.37 g (63%) of the title compound as a yellow solid. m.p. 163° (dec).

Physical characteristics are as follows:

Analysis: Calcd. for $C_{25}H_{21}F_3N_2O_2$·HCl: C, 63.22; H, 4.67; Cl, 7.47; N. 5.90. Found: c, 63.00; H, 4.93; Cl, 7.40; N, 5.80.

Mass Spectrum: Ions at (m/e): 439, 394, 393, 265, 264, 236, 159, 103, 91.

NMR (DMSO-$\delta_6$): δ4.24 (d, J=7Hz, 2H), 5.48 and 5.51 (s's, 3H), 7.13-8.07 (m, 15H).

Infrared: νmax (mull) 3156, 3107, 3075, 3052, 3038, 3032, 2783, 2668, 2607, 2555, 2501, 2461, 2401, 1739, 1621, 1602, 1580, 1536, 1500, 1486, 1330, 1270, 1252, 1226, 1204, 1191, 1179, 1170, 1162, 1155, 1114, 1077, 883, 801, 741, 731, 702, 696 cm$^{-1}$.

EXAMPLE 3

Sodium α-[3-(trifluoromethyl)benzylamino]-1-benzylindole-3-acetate

A mixture of 3 g (6.84 mmoles) of α-[3-(trifluoromethyl)benzylamino]-1-benzylindole 3-acetic acid, 3.4 ml (6.80 mmoles) of 2N NaOH, and 100 ml of MeOH was warmed until a solution was obtained (one to two hours). The solvent was evaporated. The residue was dried in a vacuum oven at 66° for 70 hours giving 2.70 (86%) of the title compound as an orange solid, m.p. 210°-215°.

Physical characteristics are as follows:

Analysis: Calcd. for $C_{25}H_{20}F_3NaN_2O_2$: C, 65.21; H, 4.38; N, 6.09. Found: C, 65.57; H, 4.46; N, 6.12.

Mass Spectrum (FAB): Ions at (m/e); 484, 483 (M+Na)+, 393, 287, 286, 264, 235, 159, 91, 23.

Infrared: νmax (mull) 3109, 3088, 3060, 3030, 1613, 1550, 1497, 1482, 1583, 1393, 1330, 1167, 1122, 1075, 915, 802, 791, 739, 700 cm$^{-1}$.

EXAMPLE 4

α-[3-(Trifluoromethyl)benzylamino]-1-benzylindole-3-acetic acid and methyl α-[3-(trifluoromethyl)benzylamino]-1-benzylindole-3-acetate hydrochloride To a stirred solution of 7.24 g (41.34 mmoles) of 3-(trifluoromethyl)benzylamine and 4 mL (4.2 g, 69.88 mmoles) acetic acid in 50 mL of MeOH was added 7.14 g (34.45 mmoles) of 1-benzylindole followed by a solution of 3.64 g (41.34 mmoles) of methyl glyoxylate in 50 mL of MeOH. The resulting solid was collected by filtration, washed with MeOH, and dried giving 4.28 g of pale pink solid. The solid and 50 mL of MeOh were heated to boiling. The majority of the solid did not dissolve. After cooling to room temperature, the solid was collected by filtration, and dried giving 4.07 g (27%) of α-[3-trifluoromethyl)benzyl]-1-benzylindole-3-acetic acid compound as a pale pink solid, m.p. 176°-178° (dec).

Physical characteristics are as follows:

Analysis: Calcd. for $C_{25}H_{21}F_3N_2O_2$: C, 68.84; H, 4.83; N, 6.39. Found: C, 68.55; H, 4.79; N, 6.28.

Mass Spectrum: Ions at (m/e): 438 (M+), 394, 393, 392, 235, 220, 175, 174, 519, 92, 91.

Infrared: νmax (mull) 3109, 3061, 3029, 2516, 2395, 2248, 1637, 1606, 1541, 1496, 1337, 1166, 1114, 802, 743, 729, 701 cm$^{-1}$.

The solvent was evaporated from the combined original filtrate and washing. The residue was treated with 200 ml of H$_2$O and then NaHCO$_3$ was added until the CO$_2$ evolution ceased. The mixture was extracted with CH$_2$Cl$_2$ (3×100 ml) (some insoluble solid was present). the combined extacts were washed with 50 ml of brine and dried over MgSO$_4$. Evaporation of the solvent left 10.97 g of brown oil. The oil was chromatographed on a 700 g column of silica gel. The column was eluted with 2% MeOH—CH$_2$Cl$_2$ and 200 ml fractions were collected. The fractions were assayed by silica gel tlc (1×4")(25% acetone-Skellysolve B). Fractions 23-30 were combined giving 5.8 g of brown oil. The oil was slurried with 50 ml of 25% acetone-Skellysolve B and then filtered to remove some insoluble solid. The filtrate was applied to a 400 g column of silica gel. The column was eluted with 25% acetone-Skellysolve B and 100 ml fractions were collected. The fractions were assayed as before. Fractions 14–15 were combined giving 2.06 g of methyl ester as a yellow-brown oil. The 2.06 g (4.55 mmoles) was dissolved in 50 ml of acetone and added to a solution of 0.53 g (4.57 mmoles) of fumaric acid in 10 ml of EtOH. The resulting solution was concentrated and then hexane was added. Cooling gave 2.22 g of white solid. The 0.89 g (1.97 mmoles) of methyl ester from fraction 16 was dissolved in 25 ml of acetone and then added to a solution of 0.23 g (1.98 mmoles) of fumaric acid in 5 ml of EtOH. The resulting solution was concentrated and then hexane was added. Cooling overnight gave 0.79 g of white solid. The 0.79 g and the 2.22 g were combined in acetone. The solution was concentrated. The solid (ca 0.53 g, m.p. ca 290° dec) which separated and which was removed by filtration was probably fumaric acid. The filtrate was concentrated and hexane was added. The solid which separated was removed by filtration. The filtrate was concentrated and hexane was added. Only a small amount of solid separated.

The solid was removed by filtration. The solvent was evaporated leaving 2.19 g of oil. A solution of the oil in 100 ml of ether was washed with $NaHCO_3$ solution and then with brine and dried over $MgSO_4$. Evaporation of the solvent left 1.90 g of yellow oil.

NMR ($CDCl_3$): $\delta$2.22–2.4 (br s, 1H), 3.72 (s, 3H), 3.88 (s, 2H), 4.75 (s, 1H), 2.58 (s, 2H), 7.1–7.9 (m, 13H). Also peaks for EtOH were present.

The 1.90 g of oil was dissolved in ether. An excess of a solution of anhydrous hydrogen chloride in either was added. Nothing separated. The solution was concentrated and hexane was added. An oil separated which after standing several days at room temperature began solidifying. The supernatant liquid was decanted. The remaining oil solidified within a few minutes. The solid was crystallized from $CH_2Cl_2$-hexane. After several hours a sticky solid had formed. The supernatant liquid was decanted. Upon rubbing, crushing and drying 1.10 g (7%) of α[3-(trifluoromethyl)benzylamino]-1-benzylindole-3-acetic acid hydrochloride was obtained as an ivory free-flowing powder, m.p. 138° (dec).

Physical characteristics are as follows:

Analysis: Calcd. for $C_{26}H_{23}F_3N_2O_2.HCl$: C, 63.87; H, 4.95; Cl, 7.25; N, 5.73. Found: C, 64.01; H, 4.76; Cl, 7.05; N, 5.71.

Mass Spectrum: Ions at (m/e): 452, 395, 394, 393, 234, 233, 159, 92, 91, 65.

NMR ($CDCl_3$): $\delta$ 3.7 (s, 3H), 4.0 (d, J=13 Hz, 1H), 4.7 (d, J=13 Hz, 1H), 5–12 (s, 1H), 5.38 (s, 2H), 7.12–7.83 (m, 13H), 7.9–8.18 (m, 3H).

Infrared: νmax (mull) 3092, 3067, 3052, 3027, 2603, 2551, 2512, 2434, 2384, 1745, 1605, 1559, 1541, 1496, 1331, 1206, 1168, 1129, 1076, 806, 741, 702 cm$^{-1}$.

The second supernatant liquid was concentrated and then cooled in the refrigerator for several days giving 0.55 g (3%) of α-[3-(trifluoromethyl)benzylamino]-1-benzylindole-3-acetic acid hydrochloride as an ivory solid.

Utilizing a procedure similar to that of Example 4 but substituting the appropriately substituted indole and amine for 1-benzylindole and 3-(trifluoromethyl)benzylamine, there is obtained the following compounds:

Methyl α-[3-(trifluoromethyl)benzylamino]-1,2-dimethylindole-3-acetate hydrochloride as a purple solid, m.p. 141° (dec).

Physical characteristics are as follows:

Analysis: Calcd. for $C_{21}H_{21}F_3N_2O_2.HCl$: C, 59,08, H, 5.20, Cl, 8.31; N, 6.56. Found C, 59.05; H, 5.45; Cl, 8.18; N, 6.50.

Mass Spectrum: Ions at (m/e): 390, 332, 331, 172, 171, 159, 157, 156, 145, 144.

NMR (DMSO-$d_6$): $\delta$ 2.42 (s, 3H), 3.41 (br s, 3H), 3.69 (s, 3H), 4.23 (br s, 2H); 5.51 (br s, 1H), 6.99–8.12 (m, 8H).

Infrared: νmax (mull) 3071, 3050, 3698, 2637, 2611, 2581, 2252, 1747, 1614, 1584, 1563, 1326, 1289, 1278, 1226, 1176, 1161, 1119, 1079, 853, 808, 749, 745, 703 cm$^{-1}$.

Methyl α-[3-(trifluoromethyl)benzylamino]-1-benzyl-2-methylindole-3-acetate hydrochloride as a pale grey solid, m.p. 138°–141°.

Physical characteristics are as follows:

Analysis: Calcd. for $C_{27}H_{25}F_3N_2O_2.HCl$: C, 64.47; H, 5.21; Cl, 7.06; N, 5.57. Found: C, 64.38; H, 5.34; Cl, 7.01; N, 5.42.

Mass Spectrum: Ions at (m/e): 466, 409, 408, 407, 316, 248, 247, 159, 157, 130, 91.

NMR ($CDCl_3$): $\delta$ 2.08 (s, 3H), 3.71 (s, 3H), 3.92 (d, J=14 Hz, 1H), 4.5 (d, J=14 Hz, 1H), 5.1 (s, 1H), 5.25 (s, 2H), 7.0–7.7 (m, 11H), 7.9–8.14 (m, 2H).

Infrared: νmax (mull) 3066, 3027, 2718, 2625, 2606, 2588, 2496, 2410, 1754, 1741, 1616, 1605, 1592, 1573, 1557, 1497, 1350, 1330, 1271, 1228, 1206, 1170, 1163, 1155, 1123, 1078, 880, 804, 793, 744, 740, 704, 695 cm$^{-1}$.

α-[N-tert-butoxycarbonyl-3-(trifluoromethyl)benzylamino]-1-benzylindole-3-acetic Acid Hydrate (1:1) as a buff solid, m.p. 108°–111°.

Physical characteristics are as follows:

Analysis: Calcd. for $C_{30}H_{29}F_3N_2O_4.H_2O$: C, 64.74; H, 5.61; N, 5.03. Found: C, 64.62; H, 5.21; N, 5.04.

Mass Spectrum: Ions at (m/e): 539, 538, 494, 483, 438, 437, 393, 340, 264, 159, 91, 57, 45, 41, 29.

NMR ($CDCl_3$): $\delta$ 0.9–1.5 (br, 9H), 4.2–4.5 (br, 2H), 4.6–4.9 (br, 3H), 6.2–7.3 (br, 14H), 7.4–7.7 (br, 1H).

Infrared: νmax (mull) 3430, 3113, 3062, 3031, 1689, 1651, 1616, 1551, 1497, 1330, 1163, 1125, 1074, 741, 701 cm$^{-1}$.

EXAMPLE 5

α-[3-(Trifluoromethyl)benzylamino]-1-benzylindole-3-N,N,-dimethylacetamide hydrochloride A solution of 9.98 g (48.15 mmoles) of 1-benzylindole, 8.44 g (48.18 mmoles) of 3-(trifluoromethyl)benzylamine, 6 mL (6.29 g, 104.8 mmoles) of acetic acid, and 4.87 g (48.17 mmoles) of N,N-dimethyl-2-oxoacetamide in 150 mL of MeOH was stirred and then allowed to stand for four days. Then the solution was refluxed for one day. The solvent was evaporated. The residue was shaken with 100 mL of $CH_2Cl_2$ and 100 mL of dilute NaOH solution. The layers were separated. The aqueous layer was extracted with 100 mL of $CH_2Cl_2$. The combined organic phases were washed with 50 mL of brine and dried over $MgSO_4$. Evaporation of the solvent left 21.79 g of yellow oil. The oil was chromatographed on a 1100 g column of silica gel. The column was eluted with 5% MeOH-$CH_2Cl_2$ and 200 mL fractions were collected. The fractions were assayed by silica gel tlc (1×4") (5% MeOH-$CH_2Cl_2$).

Fractions 26–30 were combined giving 7.61 g of crude α-[3-(trifluoromethyl)-benzylamino)-1-benzylindole-3-N,N-dimethylacetamide as a yellow-brown oil. Fractions 23–25 were combined giving 6.86 g of a α-[3-(trifluoromethyl)-benzylamino]-1-benzylindole-3-N,N- dimethylacetamide as a yellow oil. A solution of the oil in ether was mixed with a solution of excess anhydrous HCl in ether. A pink oil separated. The solvent was evaporated (on a steam bath) until the oil had changed to a solid. The solids was collected by filtration and washed with ether giving 5.91 g (24%) of the titled compound as a pink solid, m.p. 187° (dec).

Physical characteristics are as follows:

Analysis: Calcd. for $C_{27}H_{27}H_{16}F_3N_3O$:HCl: C, 64.60; H, 5.42; Cl, 7.06; N, 8.37. Found: C, 64.46; H, 5.54; Cl, 6.94; N, 8.34.

Mass Spectrum: Ions at (m/e): 465, 426, 395, 394, 393, 234, 233, 159, 92, 91, 72, 65.

NMR ($CD_3OD$): δ 2.81 (s, 3H), 2.96 (s, 3H), 4.34 (s, 2H), 4.73–4.98 (br, 2H), 5.43 (s, 2H), 5.91 (s, .1H), 7.15–8.0 (m, 14H).

Infrared: νmax (mull) 3097, 3049, 2655, 2516, 2470, 2430, 2406, 2368, 1643, 1615, 1582, 1535, 1495, 1331, 1182, 1173, 1155, 1122, 1079, 794, 746, 732, 701 cm$^{-1}$.

EXAMPLE 6

Ethyl α-[3-(trifluoromethyl)benzylamino]-1-benzylindole-3 acetate

To a magnetically stirred suspension of α-[3-(trifluoromethyl)benzylamino)-1-benzylindole-3-acetic acid (21.9 g, 0.05 mol) in 250 mL of methanol at room temperature was treated with 11.34 g of sodium methoxide (25% in methanol) at once. The resulting solution was stirred for two hours, concentrated directly on a rotary evaporator and finally the resulting white residue was pumped down under high vacuum using a warm water bath at ca 50° C. The dry sodium salt was dissolved in 100 mL of dimethylformamide, charged at once with ethyl iodide (9.36 g, 0.06 mol, 1.20 eq) and stirred in the dark for 48 hours with an additional 50 mL of dimethylformamide being added after 20 hours to facilitate stirring of the gelantinous precipitate which formed. The contents were diluted with ether and poured into 125 mL of ice water plus 125 ml of saturated brine. The aqueous phase was separated from the organic layer and extracted once more with ether. The combined organic extracts were dried with anhydrous $Na_2SO_4$ and concentrated at reduced pressure. Flash chromatography with 250 g of silica gel packed and eluted with ethyl acetate-hexane (1:4) gave the title compound as a yellow oil.

Substitution of methyl iodide for ethyl iodide afforded methyl-α-[3-(trifluoromethyl)benzylamino-1-benzylindole-3-acetate in 51% yield.

EXAMPLE 7

Ethyl α-[3(trifluoromethyl)-benzylamino]-1-ethoxycarbonyl-indole-3-acetate hydrochloride To a magnetically stirred solution of ethyl α-[3(trifluoromethyl)-benzylamino]-indole-3-acetate (1.00 g, 2.66 mmol) in 15 mL of DMF was added under nitrogen 0.112 g (2.79 mmol) of sodium hydride (60% oil dispersion). After stirring at room temperature for 10 minutes, 0.26 ml (2.79 mmol) of ethyl chloroformate was added. Stirring was continued for two hours at room temperature. At the end of this time, the reaction contents were poured into ice water, the aqueous solution extracted with ether and the ether solution washed with saturated brine and dried over anhydrous $Na_2SO_4$. Removal of the solvent in vacuo gave the crude product which was chromatographed with 80 g of silica gel using hexane-ethyl acetate (4:1) to yield 0.857 g of the title compound.

Physical characteristics are as follows:

TLC (Skellysolve B—EtOAc, Rf 0.65).

NMR ($CDCl_3$, δ) 8.18 (m, 1H), 7.67–7.23 (m, 8H), 4.60 (s, 1H), 4.47 (m, 2H), 4.21 (m, 2H), 3.86 (m, 2H), 1.47 and 1.22 (2 triplets, 6H).

The above product was treated with ethereal-HCl to afford after crystallization from ether-hexane 0.797 g of HCl salt, m.p. 153°–155° C.

Physical characteristics are as follows:

Analysis: Calcd. for $C_{23}H_{23}F_3N_2O_4$.HCl: C, 57.02; H, 4.96; N, 5.79. Found: C, 57.25; H, 5.09; N, 5.85.

NMR ($CDCl_3$, δ) 8.31 (s, 1H), 8.75 (m, 1H), 8.00 (m, 1H), 7.62–7.26 (m, 1H), 4.97 (s, 1H), 4.77 (m, 1H), 4.50 (m, 2H), 4.27–4.04 (m, 3H), 1.49 and 1.15 (2 triplets, 6H).

Utilizing a procedure similar to that in Example 7, but substituting the appropriate chloroformate for ethyl formate, there is obtained either α-[3-(trifluoromethyl)-benzylamino]-1-benzyloxycarbonyl-indole-3-acetate hydrochloride, m.p. 150°–152° C. and methyl-α-[N-methyl-3-(trifluoromethyl)benzylamino]-1-benzyl-indole-3-acetate hydrochloride, m.p. 151°–154° C.

EXAMPLE 8

Methyl α-[3-(trifluoromethyl)benzylamino]-1-benzylindole-3-acetate

To a magnetically stirred solution of 100 ml of methanol cooled in an ice-acetone bath at ca. −15° C., was treated dropwise with acetyl chloride (27.3 g, 350 mmol, 35 eq) over a six-minute period as a convenient way to generate HCl in situ. The solution was stirred at ambient temperature for 45 minutes, then solid α-[3-(trifluoromethyl)benzylamino]-1-benzylindole-3-acetic acid was added which formed a dark rose colored solution. After stirring for 22 hours the reaction mixture was poured into 100 mL of saturated $NaHCO_3$ solution containing 100 mL of crushed ice, basified with additional solid $NaHCO_3$ powder until the rose color dissipated and extracted twice with ether. The combined organic extracts were washed with saturated $NaHCO_3$ (1×75 mL), saturated brine (1×100 mL), dried with anhydrous $NaSO_4$ and concentrated in vacuo. Flash chromatography with 100 g of silica gel using ethyl acetate-hexane (1:2) afforded 4.07 g of the title compound as a golden oil.

EXAMPLE 9

Methyl α-[3-(trifluoromethyl)benzylamino-1-benzylindole-3-acetate

To a magnetically stirred solution of ethyl α-[3-(trifluoromethyl)benzylamino]-1-benzylindole-3-acetate ester (7.76 g, 16.7 mmol) in 125 mL of methanol was added 3.80 mL (16.7 mmol) of 25% sodium methoxide in methanol solution. Stirring was continued at room temperature for 15 hours. At the end of this time, the methanolic solution was poured onto 150 mL of crushed ice, thoroughly extracted with methylene chloride and the organic layer dried over anhydrous sodium sulfate. Concentration of the solvent in vacuo gave the crude product which was chromatographed over 150 g of silica gel using hexane-ethyl acetate (4:1) to afford the title compound as an oil in quantitative yield.

EXAMPLE 10

Ethyl α-[3-(trifluoromethyl)benzylamino]-1-benzylindole-3-acetate

To a magnetically stirred solution of methyl α-[3-(trifluoromethyl)benzylamino-]-1-benzylindole-3-acetate hydrochloride (100 mg) in 8 mL of ethanol was added 70 μL of 25% sodium methoxide in methanol. After stirring at room temperature for two hours, TLC analysis showed 90% conversion to the title compound.

EXAMPLE 11

Methyl α-[3-(trifluoromethyl)benzylamino]-1-benzylindole-3-acetate hydrochloride A magnetically stirred solution of methyl α-[3-(trifluoromethyl)benzylamino]-1-benzylindole-3-acetate (4.07 g, 9.0 mmol) in 65 mL of ether cooled at 0°–5° C. was treated dropwise over a four-minute period with a stock solution of hydrogen chloride in ether (3.8 mL, 11.71 mmol, 1.3 eq, 3.1 mmol per mL). The cooling bath was removed after addition was completed and the mixture stirred at room temperature overnight. The precipitated white solid was collected, washed with ether-hexane (1:1) and recrystallized from acetone-ethyl acetate-ether solvent mixture to yield 4.18 g (95%) of the title compound.

EXAMPLE 12

Preparation of Ethyl α-[3-(trifluoromethyl)benzylamino]-1-ethylindole-3-acetate, hydrochloride Ethyl α-[3-(trifluoromethyl)benzylamino]-1-ethylindole-3-acetate (1.50 g, 3.70 mmol) was placed in 25 mL of ether, saturated with HCl gas and stirred under nitrogen for 30 minutes. The contents were concentrated to dryness in vacuo and the resulting solid recrystallized from acetone-ether (1:5) to give 1.30 g of the title compound as a crystalline white solid m.p. 141°–143° C.

Physical characteristics are as follows:

Analysis: Calcd. for $C_{22}H_{24}F_3N_2O_2Cl$: C, 59.93; H, 5.49; N, 6.35; F, 12.93; Cl 8.04. Found: C, 59.68; H, 5.68; N, 6.30; F, 12.99; Cl 7.90.

NMR $CDCl_3$, δ) 7.94–7.17 (m, 9H), 5.00 (s, 1H), 4.30–3.90 (m, 4H), 1.60–1.50 (m, 5H), 1.16 (t, 3H, J=7 Hz).

EXAMPLE 13

Ethyl α-[N-ethyl-3-(trifluoromethylbenzylamino]-1-benzylindole-3-acetate, ethyl α[N-ethyl-3-(trifluoromethyl)benzylamino]-indole-3-acetate, and ethyl α-[3-(trifluoromethyl)benzylamino]-indole-3acetate To a magnetically stirred suspension of α-[3-(trifluoromethyl)benzylamino]-indole-3-acetic acid (20,88, g, 60 mmol) in 350 mL of methanol was added 16.46 mL (72 mmol) of 25% sodium methoxide in methanol solution. The contents were allowed to stir under nitrogen at room temperature for one hour. At the end of this period the methanol was removed in vacuo and replaced with 150 mL of dimethylformamide (DMF). The reaction mixture was cooled in an ice-water bath, 5.76 mL (72 mmol) of ethyl iodide added, and the reaction stirred overnight in the dark at room temperature. The reaction was diluted with one liter of water, the aqueous phase thoroughly extracted 3× with ether, the ether extract washed with saturated brine and dried over anhydrous sodium sulfate. Removal of the ether in vacuo gave the crude product which was purified by flash chromatography (600 g silica gel). Elution with hexane-ethyl acetate (4:1) afforded 1.22 g of ethyl α-[N-ethyl-3-(trifluoro-methyl)benzylamino]-1-ethylindole-3-acetate (least polar), 2.76 g of ethyl α-[N-ethyl-3-(trifluoromethyl)-benzylamino]-indole-3-acetate, 2.62 g of ethyl α-[3-(trifluoromethyl)-benzylamino]-1-ethylindole-3-acetate and 8.67 g of ethyl α-[3-(trifluoromethyl)-benzylamino]-indole-3-acetate (most polar).

Physical characteristics are as follows:

TLC 1:2 EtOAc-Hexane

Ethyl α-[N-ethyl-3-(trifluoromethyl)-benzylamino]-1-ethylindole-3-acetate

Physical characteristics are as follows:

Rf: 0.78.

NMR ($CDCl_3$, δ) 4.99 (S, 1H), 4.32–4.08, (m, 4H), 3.95 (1H), 3.70 (d, 1H, J=12 Hz), 2.68 (m, 2H), 1.44, 1.28, 1.09 (3triplets, 9H).

Analysis: Calcd. for $C_{24}H_{27}F_3N_2O_2$: 432 (M+). Found: 432.

Infrared (neat $cm^{-1}$) 1330, 1124, 1164, 1175, 1731, 471, 1072, 1197, 702, 1463.

Ethyl α-[N-ethyl-3-(trifluoromethyl)-benzylamino]-indole-3-acetate

Physical characteristics are as follows:

Rf: 0.64.

NMR ($CDCl_3$, δ) 5.00 (s, 1H), 4.32–4.19 (m, 3H), 3.96 (d, 1H, J=15 Hz), 3.70 (d, 1H, J=15 Hz, 2.70 (m, 2H), 1.30 and 1.09 (2triplets, 6H).

Analysis: Calcd. for $C_{22}H_{23}F_3N_2O_2$: 404 (M+). Found: 404.

Infrared (Neat cm−1) 1330, 1124, 1164, 1176, 1729, 1072, 744, 1096, 703, 1457.

Ethyl α-[N-ethyl-3-(trifluoromethyl)-benzylamino]-indole-3-acetate hydrochloride Physical characteristics are as follows:

Rf: 0.50.

NMR ($CDCl_3$, δ) 4.65 (s, 1H), 4.30–4.07 (m, 4H), 3.86 (dd, 2H, J=12 Hz, 1.45 and 1.23 (2 triplets, 6H).

Analysis: Calcd. for $C_{22}H_{23}F_3N_2O_2$: 404 ($M^{30}$). Found: 404.

Infrared (Neat cm−1) 1330, 1124, 1164, 1731, 1176, 1188, 742, 1073, 704, 1463.

Ethyl α-[3-(trifluoromethyl)-benzylamino]-indole-3-acetate

Physical characteristics are as follows:

Rf: 0.31.

NMR ($CDCl_3$, δ) 4.68 (s, 1H), 4.27–4.10 (m, 2H), 3.92–3.82 (m, 2H), 1.22 (t, 3H, J=7 Hz).

Analysis: Calcd. for $C_{20}H_{19}F_3N_2O_3$: 376 (M+). Found: 376.

Infrared (Neat $cm^{-1}$) 1330, 1124, 1166, 1730, 1177, 1189, 745, 1073, 703, 1097.

EXAMPLE 14

Methyl α-[N-methyl-3-(trifluoromethyl)benzylamino]-1-(4-chlorobenzyl)indole-3-acetate To a magnetically stirred suspension of sodium hydride (60% oil dispersion washed two times with hexane, 80 mg, 2.0 mmol) in 5 mL of dimethylformamide (DMF) under nitrogen was added methyl α-[3-(trifluoromethyl)benzylamino]-indole-3acetate (752 mg, 2.0 mmol) dissolved in 2 mL DMF. Stirring was continued at room temperature for 10 minutes. At the end of this time, 0.322 g (2.0 mmol) of parachlorobenzyl chloride was added and the reaction stirred at room temperature for one hour. The reaction was diluted with ether and the ether solution was washed two times with water. The ether extract was then washed with saturated brine, dried over anhydrous sodium sulfate and concentrated in vacuo to give the crude product. Flash chromatography of the crude product with 100 g of silica gel and using hexane-ethyl acetate (4:10) as the eluent afforded 419 mg of the title compound.

Physical characteristics are as follows:

TLC: 1:1 Hexane-ethyl acetate, RF 0.58.

NMR (CDCl$_3$, δ) 7.72–7.03 (m, 13H), 5.25 (s, 2H), 4.69 (s, 1H), 3.86 (s, 2H), 3.72 (s, 3H).

High Resolution Mass Spectrum

Calcd for $C_{26}H_{22}ClF_3N_2O_2$: 486.1322. Found: 486.1346.

Infrared (neat, cm$^{-1}$) 1330, 1165, 1124, 1736, 744, 1197, 1073, 703, 1467, 1493.

EXAMPLE 15

Methyl α-(3-Trifluoromethylphenylmethylamino)-5-methoxy-3-indoleacetate

To a stirred solution of 7.24 g (41.34 mmoles) of 3-(trifluoromethyl)benzylamine and 4 mL (4.2 g, 69.88 mmoles) of acetic acid in 50 mL of MeOH was added a solution of 3.65 g (41.34 mmoles) of glyoxylic acid monohydrate in 50 mL of MeOH followed by 5.07 g (34.45 mmoles) of 5-methoxyindole. The resulting solution was allowed to stand for three days. Solid separated during this period. The solid was collected by filtration, washed with MeOH, and dried giving 3.02 g f white solid, m.p. ca. 192° C. (dec). The solvent was evaporated from the combined filtrate and washing. The residue was treated with 200 mL of H$_2$O. Sodium bicarbonate was added until the CO$_2$ evolution ceased. The mixture was extracted with CH$_2$Cl$_2$ (3×100 mL). The combined extracts were washed with 50 mL of brine and dried over MgSO$_4$. Evaporation of the solvent left 8.71 g of brown oil with slowly solidified. The solid was chromatographed on a 700 g column of silica gel. The column was eluted with 30% acetone-Skellysolve B and 200 mL fractions were collected. The fractions were assayed by silica gel TLC (1×4") (40% acetone-Skellysolve B). Fractions 14–20 were combined and crystallized from CH$_2$Cl$_2$-hexane giving 5.14 g of ivory-buff solid. The solid was recrystallized from acetone-hexane giving 4.8 g (36%) of the title compound as ivory needles, m.p. 109°–110.5° C.

Physical characteristics are as follows:

Analysis: Calcd. for $C_{20}H_{19}F_3N_2O_3$: C, 61.22; H, 4.88; N 7.14. Found: C, 61.27; H, 4.96; N, 7.17.

Mass Spectrum: Ions at (m/e): 392 (M+), 334, 333, 174, 173, 160, 159, 147, 144, 131.

NMR (CDCl$_3$): δ 2.2–2.45 (br, 1H), 3.72 (s, 3H), 3.84 (s, 3H), 3.89 (s, 2H), 4.7 (s, 1H), 6.85–7.02 (m, 1H), 7.13–7.4 (m, 3H), 7.48–7.8 (m, 4H), 8.2–8.4 (br, 1H).

Infrared: νmax (mull), 3324, 3309, 3130, 3077, 3040, 1746, 1725, 1626, 1587, 1492, 1332, 1233, 1199, 1162, 1120, 1071, 811, 793, 706 cm$^{-1}$.

EXAMPLE 16

α-Aminoindole-3-acetic Acid

A mixture of 2 g of ethyl α-aminoindole-3-acetate, excess dilute NaOH solution, and a few mL of MeOH was stirred occasionally for 25 minutes. Since a solution had not been obtained, the mixture was heated on a steam bath for ten minutes. The resulting solution was allowed to stand at ambient temperature for 50 minutes. The solution was acidified with acetic acid. The solid which separated was collected by filtration and washed with H$_2$O giving 1.50 g (86%) of the title compound as small buff plates, m.p. 217° (dec).

Physical characteristics are as follows:

Analysis: Calcd. for $C_{10}H_{10}N_2O_2$: C, 63.14; H, 5.30; N, 14.73. Found: C, 62.63; H, 5.63; N, 14.65.

Mass Spectrum: Ions at (m.e): 190, 173, 146, 145, 143, 129, 118, 117, 91, 89, 44.

Infrared: νmax (mull) 3402, 3114, 3069~3000b, 2660, 1633, 1618, 1579, 1575, 1546, 1522, 1490, 1402, 1366, 746 cm$^{-1}$.

EXAMPLE 17

α-[2-(4-Aminosulfonylphenyl)ethylamino]-3-indoleacetic acid Hydrate (1:1)

To a stirred solution of 6.01 g (0.03 mmole) of 4-(2-aminoethyl)benzenesulfonamide and 2.5 mL (2.62 g 0.044 mole) of acetic acid in 150 mL of MeOH was added a solution of 2.64 g (0.03 mole) of methyl glyoxylate in 50 mL of MeOH followed by 2.93 g (0.025 mole) of indole. Initially a solution was obtained. Soon solid began separating. The resulting mixture was allowed to stand for four days. The solid was collected by filtration, washed with ether and dried give 3.72 g (38%) of the title compound as a buff solid, m.p. 226° C. (dec). The solid insoluble in CH$_2$Cl$_2$, MeOH, DMSO, DMF and acetic acid.

Physical characteristics are as follows:

Analysis: Calcd. for $C_{18}H_{19}N_3O_4S\cdot H_2O$: C, 55.23; H, 5.41; N, 10.73; S, 8.19. Found: C, 55.06; H, 5.27; N, 10.75; S, 8.50.

Mass Spectrum: Ions at (m/e): 374, 328, 201, 188, 175, 174, 145, 130, 118, 103.

Infrared: νmax (mull), 3394, 3357, 3270, 3133, 3033, ~3000 br, 2713, 2619, 2522, 2422, 1594, 1490, 1340, 1328, 1167, 1098, 821, 769, 755 cm$^{-1}$.

EXAMPLE 18

α-[(S-α-Methylbenzylamino)-1-benzylindole-3-acetic Acid

To a solution of 4 g (19.3 mmoles) of 1-benzylindole and 1.95 g (21.18 mmoles) of glyoxylic acid monohydrate in 125 mL of MeOH and added 2.35 g (19.39 mmoles) of (S)-(−)-α-methylbenzylamine. The solution was stirred and then allowed to stand for 22 hours. The gelantinous solid which separated was collected by filtration and washed with MeOH giving 3.38 g (46%) of the title compound as an orange solid, m.p. 188° C. (dec).

Physical characteristics are as follows:

Analysis: Calcd. for $C_{25}H_{24}N_2O_2$: C, 78.10; H, 6.29; N, 7.29. Found: C, 77.62; H, 6.52; N, 7.14.

Mass Spectrum: Ions at (m/e): 339, 338, 323, 235, 120, 106, 105, 91, 79, 77, 65, 50.

Infrared: μmax(mull) 3060, 3032, 2669, 2529, 2409, 2175, 1620, 1583, 1552, 1497, 1375, 1355, 1346, 768, 746, 741, 727, 701 cm$^{-1}$

EXAMPLE 19

1-Phenylmethyl-α-(2-(3-(trifluoromethyl)phenyl)-1-pyrrolidinyl)1H-indole-3-acetic acid To a solution of 2-(3-trifluoromethylphenyl)-1-pyrrolidine (2.56 g, 11.9 mmol) in methanol (100 mL) was added N-benzyl-indole (2.45 g, 11.8 mmol) and glyoxylic acid mono-hydrate (1.20 g, 13.3 mmol). A white precipitate began to form within one hour, the mixture was allowed to stir overnight, after which time the precipitate was isolated by filtration. The solid was washed with methanol (3×50 mL), and dried in vacuo at 40° C. to provide 2.76 g, 49% of the title compound as a white powdery solid.

Physical characteristics are as follows:

MP: 137° C. (dec).

Infrared: (nujol): 3373, 2955, 1612, 1496, 1482, 1329, 1167, 1122, and 704 cm$^{-1}$.

EI/MS (70 eV): 433 (M+-CO$_2$, 68.8), 220 (10.4), 186 (27.5), 118 (11.8), 91 (base).

Analysis: Calcd. for C$_{28}$H$_{25}$F$_3$N$_2$O$_2$: C, 70.82; H, 5.27; N, 5.85. Found: C, 69.76; H, 5.08; N, 5.89.

EXAMPLE 20

1H-Indole-3-acetic acid, 1-[(4-chlorophenyl)methyl]-α-[[[3-(trifluoromethyl)phenyl]methyl]amino]methyl ester To a magnetically stirred suspension of sodium hydride (60% oil dispersion washed 2× with hexane, 80 mg, 3.0 mmol) in a 5 mL of dimethylformamide (DMF) under nitrogen was added methyl α-[3-(trifluoromethyl)benzylamin]-indole-3-acetate (752 mg, 2.0 mmol) dissolved in 2 mL DMF. Stirring was continued at room temperature for 10 minutes. At the end of this time, 0.322 g (2.0 mmol) of parachlorobenzyl chloride was added and the reaction stirred at room temperature for one hour. The reaction was diluted with ether and the ether solution was washed 2× with water. The ether extract was then washed with saturated brine, dried over anhydrous sodium sulfate and concentrated in vacuo to give the crude product. Flash chromatography of the crude product with 100 g of silica gel and using hexane-ethyl acetate (4:1) as the eluent afforded 419 mg of the title compound.

Physical characteristics are as follows:

Analysis: Calcd. for C$_{26}$H$_{22}$ClF$_3$N$_2$O$_2$: 486.1322. Found: 486.1346.

Utilizing a procedure similar to that use in Example 20 there is obtained the following compounds:

1H-Indole-3-acetic acid, 1-butyl α-[[[3-(trifluoromethyl)phenyl]methyl]amino], ethyl ester, m.p. 153°-155° C.

Physical characteristics are as follows:

Analysis calcd. for C$_{23}$H$_{23}$F$_3$N$_2$O$_4$·HCl: C, 57.02; H, 4.96; N, 5.74. Found: C, 57.25; H, 5.09.

1H-Indole-3-acetic acid, 1-(2-ethoxyethyl)-α-[[[3-(trifluoromethyl)]phenyl]methyl]aminoethyl ester.

Physical characteristics are as follows:

Analysis: Calcd. for C$_{24}$H$_{27}$O$_3$F$_2$N$_2$O$_3$: 448.1974. Found: 448.1986.

1H-Indole-3-acetic acid, 1-(2-ethoxyethyl)-α-[[[3-(trifluoromethyl)phenyl]methyl]amino]ethyl ester, monohydrochloride, m.p. 139°-141° C.

Physical characteristics are as follows:

Analysis: Calcd. for C$_{24}$H$_{27}$F$_3$N$_2$O$_3$·HCl: C, 59.44; H, 5.82; N, 5.78; Cl, 7.31. Found: C, 59.90; H, 5.65; Cl, 7.21.

1H-Indole-3-acetic acid, 1-[(4-chlorophenyl)methyl]α-[[[3-(trifluoromethyl)phenyl]methyl]amino]ethyl ester.

Physical characteristics are as follows:

Analysis: Calcd. for C$_{24}$H$_{24}$F$_3$N$_2$O$_2$Cl: 500.1478. Found: 500.1439.

1H-Indole-3-acetic acid, 1-[(4-chlorophenyl)methyl-α-[[[3-(trifluoromethyl)phenyl]methyl]amino]ethyl ester, monohydrochloride, m.p. 146°-148° C.

Physical characteristics are as follows:

Analysis: Calcd. for C$_{27}$H$_{24}$Cl$_2$N$_2$O$_2$·HCl: C, 60.35; H, 4.69; N, 5.21; Cl, 13.20. Found: C, 60.16; H, 4.84; Cl, 12.70.

1H-Indole-3-acetic acid, 1-(cyclohexylmethyl)-α-[[[3-(trifluoromethyl)phenyl]methyl]amino]ethyl ester.

Physical characteristics are as follows:

Analysis: Calcd. for C$_{27}$H$_{21}$F$_3$N$_2$O$_2$: 472.2337. Found: 472.2330.

1H-Indole-3-acetic acid, 1-(cyclohexylmethyl)-α-[[[3-(trifluoromethyl)phenyl]methyl]amino]ethyl ester, monohydrochloride, m.p. 151°-153° C.

Physical characteristics are as follows:

Analysis: Calcd. for C$_{27}$H$_{31}$F$_3$N$_2$O$_2$·HCl: C, 63.71; H, 6.34; N, 5.50; C, 6.97. Found: C, 63.67; H, 6.49; N, 5.41; Cl, 6.27.

1H-Indole-3-acetic acid, 1-acetyl-α-[[[3-(trifluoromethyl)phenyl]methyl]amino]ethyl ester.

Physical characteristics are as follows:

Analysis: Calcd. for C$_{22}$H$_{21}$F$_3$O$_3$N$_2$: 418.1504. Found: 418.1510.

1H-Indole-3-acetic acid, 1-benzoyl-α-[[[3-(trifluoromethyl)phenyl]methyl]amino]ethyl ester.

Physical characteristics are as follows:

Analysis: Calcd. for C$_{27}$H$_{23}$F$_3$O$_3$N$_2$: 480.1661. Found: 480.1672.

1H-Indole-3-acetic acid, 1-benzoyl-α-[[[3-(trifluoromethyl)phenyl]methyl]amino]ethyl ester, monohydrochloride, m.p. 118°-139° C. (dec).

Physical characteristics are as follows:

Analysis: Calcd. for C$_{27}$H$_{23}$F$_3$O$_3$N$_2$·HCl: C, 62.73; H, 4.68; N, 5.42; Cl, 6.86. Found: C, 61.17; H, 4.93; N, 5.26; Cl, 6.44.

1H-Indole-3-acetic acid, 1-acetyl-α-[acetyl[[[3-(trifluoromethyl)phenyl]methyl]amino]ethyl ester.

Physical characteristics are as follows:

Analysis: Calcd. for C$_{24}$H$_{23}$O$_4$F$_3$N$_2$: 460.1610. Found: 460.1616.

1H-Indole-3-acetic acid, α-[acetyl[[3-(trifluoromethyl)phenyl]methyl]amino]ethyl ester.

Physical characteristics are as follows:

Analysis: Calcd. for C$_{22}$H$_{21}$F$_3$O$_3$N$_2$: 418.1504. Found: 418.1504.

1H-Indole-3-acetic acid, 1-[(2-chlorophenyl)methyl]-α-[[[3-(trifluoromethyl)phenyl]]methyl]amino]methyl ester.

Physical characteristics are as follows:

Analysis: Calcd. for C$_{26}$H$_{22}$ClF$_3$N$_2$O$_2$: 486.1322. Found: 486.1332.

1H-Indole-3-acetic acid, 1-[(2,4-dimethylphenyl)methyl]-α-[[[3-(trifluoromethyl)phenyl]methyl]amino]methyl]ester.

Physical characteristics are as follows:

Analysis: Calcd. for C$_{28}$H$_{27}$F$_3$N$_2$O$_2$: 480.2024. Found: 480.2019.

1H-Indole-3-acetic acid, 1-[(3-methoxyphenyl)methyl]-α-[[[3-(trifluoromethyl)phenyl]methyl]amino]methyl ester.

Physical characteristics are as follows:

Analysis: Calcd. for $C_{27}H_{25}F_3N_2O_3$: 482.1817. Found: 482.1839.

1H-Indole-3-acetic acid, 1-[(4-methoxyphenyl)methyl]-α-[[[3-(trifluoromethyl)phenyl]methyl]amino]-methyl ester.

Physical characteristics are as follows:

Analysis: Calcd. for $C_{27}H_{25}F_3N_2O_3$: 482.1817. Found: 482.1847.

1H-Indole-3-acetic acid, 1-[(3-chlorophenyl)methyl]-α-[[[3-(trifluoromethyl)phenyl]methyl]amino-methyl ester.

Physical characteristics are as follows:

Analysis: Calcd. for $C_{26}H_{22}ClF_3N_2O_2$: 486.1322. Found: 486.1327.

1H-Indole-3-acetic acid, 1-(4-pyridinylmethyl)-α-[[[3-(trifluoromethyl)phenyl]methyl]amino]methyl ester.

Physical characteristics are as follows:

Analysis: Calcd. for $C_{25}H_{22}F_3N_3O_2$: 453.1664. Found: 453.1663.

EXAMPLE 21

Methyl α-(phenylmethylamino)-3-indoleacetate

To a stirred solution of 6.43 g (0.06 mole) of benzylamine and 5 mL (5.25 g, 0.09 mole) of acetic acid in 50 mL of MeOH was added a solution of 5.28 g (0.06 mole) of methyl glyoxylate in 50 mL of MeOH followed by 5.86 g (0.05 mole) of indole. The resulting solution was allowed to stand for 69 hours. The solvent was evaporated. The residue was treated with 200 mL of $H_2O$. Sodium bicarbonate was added until $CO_2$ evolution ceased. The mixture was extracted with $CH_2Cl_2$ (3×100 mL). The combined extracts were washed with 50 mL brine and dried over $MgSO_4$. Evaporation of the solvent left 16.2 g of orange-brown oil which solidified upon standing. The solid was chromatographed on a 700 g column of silica gel. The column was eluted with 7.5% MeOH-$CH_2Cl_2$ and 200 mL fractions were collected. The fractions were assayed by silica gel (TLC (1×4") (5% MeOH-$CH_2Cl_2$). Fractions 10–14 were combined giving 12.7 g of red oil. The oil was chromatographed on a 700 g column of silica gel. The column was eluted with 40% acetone-Skellysolve B and 200 mL fractions were collected. The fractions were assayed by silica gel TLC (1×4") (40% acetone-Skellysolve B). Fractions 11–14 were combined and crystallized from ether-THF-hexane giving 8.07 g (55%) of the title compound as a pale pink solid, m.p. 91.5°–93° C.

Physical characteristics are as follows:

Analysis: Calcd. for $C_{18}H_{18}N_2O_2$: C, 73.45; H, 6.16; N, 9.52. Found: C, 73.27; H, 6.24; N, 9.52.

Mass Spectrum: Ions at (m/e): 294 ($M^+$), 236, 235, 144, 143, 130, 128, 106, 92, 91, 65.

NMR (CDCl$_3$): δ 2.28 (s, 1H), 3.68 (s, 3H), 3.81 (s, 2H), 4.71 (s, 1H), 6.9–7.45 (m, 9H), 7.6–7.85 (m, 1H), 8.4–8.7 (br, 1H).

Infrared: νmax (mull) 3275, 3205, 3166, 3151, 3130, 3112, 3089, 3065, 3029, 1732, 1619, 1586, 1580, 1539, 1498, 1312, 1238, 1193, 1167, 1118, 1109, 989, 764, 753, 738, 703 cm$^{-1}$.

EXAMPLE 22

1-Phenylmethyl-1H-indole-3-acetamide-α-((3-trifluoromethyl)phenyl)methylamine

To a solution of 3-trifluoromethylbenzyl amine (4.38 g, 25 mmol) and NaCN (1.23 g, 25 mmol) in 1.00M aqueous HCl (25 mL) was added in one portion N-benzylindole-3-carboxaldehyde (5.90 g, 25 mmol) in MeOH (25 ml). The mixture was allowed to stir for 5 hours, then the reaction was cast into Et$_2$O (1.0 L), and dried (Na$_2$SO$_4$). Concentration in vacuo afforded the crude amino-nitrile as an oily red-orange solid which was purified by chromatography on a column of silica gel (230–400 mesh, 500 g, 70 mm o.d., Et$_2$O-hexanes 1:4, 300 mL fr) using the flash technique. Fractions 6–12 gave 3.76 g (36%) of 1-phenylmethyl-1H-indole-3-acetonitrile-α-((3-trifluoromethyl)phenyl)methylamine as a relatively unstable cream colored solid which was contaminated with the starting aldehyde. This compound was utilized in the next reaction without further purification.

To a solution of the above amino nitrile (3.50 g, 8.34 mmol) in CH$_2$Cl$_2$ (10 mL), cooled in an ice water bath, was added 30% H$_2$O$_2$ (3.9 mL) followed immediately by n-Bu$_4$NHSO$_4$ (0.616 g, 1.66 mmol) and 20% aqueous NaOH (3.1 mL). The two-phase mixture was allowed to stir for five hours at room temperature then was cast into CH$_2$Cl$_2$—H$_2$O (0.5 L each). The organic phase was separated, washed with brine (0.5 L), dried (Na$_2$SO$_4$), and then concentrated in vacuo to furnish the crude amide as a pale yellow viscous oil. The crude product was purified by chromatography on a column of silica gel (230–400 mesh, 500 g, 70 mm. o.d., EtOAc-hexanes 40:60, 500 mL fractions, using the flash technique. Fractions 16–24 afforded 1.49 g (41%) of the title compound as an extremely viscous, pale yellow oil which provided a white powdery solid after trituration with Et$_2$O.

Physical characteristics are as follows:

M.P.: 112°–113° C.

TLC: (Merck, EtOAc-hexanes, 1:1, UV (+); ammonium molybdate: Rf=0.19.

$^1$H-NMR (300 Hz, CDCl$_3$): δ=7.0–7.7(14); 6.82 (brs, 1), 5.89 (brs, 1), 5.26 (s, 2), 4.54 (s, 2), 3.89 (s, 2), 2.27 (brs, 1).

$^{13}$C-NMR (75.5 MHz, CDCl$_3$): δ=175.1, 140,7, 137,0, 131.6, 128.9, 128.8, 127,8, 127.1, 126.9, 126.4, 125.0, 124.0, 122.4, 119.9, 119.5, 112.6, 110.1, 59.2, 51.9, 50.1.

Infrared (neat): 3368, 2957, 2868, 1705(w), 1656, 1465, 1455, 1378, 1330, 1188, 1173, 1162, 1123, 1074, 804, 745 and 703 cm$^{-1}$.

EI/MS (70 eV): 437 ($M^+$, 0.2), 393 (base), 159 (12.9), 91 (65.6).

Analysis: Calcd. for $C_{25}H_{22}F_3N_3O$: C, 68.64; H, 5.07; N, 9.60; Found: C, 68.26; H, 4.70; N, 9.68.

EXAMPLE 23

1-Phenylmethyl-N-3-(trifluoromethyl)phenylmethyl-L-tryptophan methyl ester

To a stirring, ice-water cooled, suspension of (S)-(−)-1-benzyl-tryptophan methyl ester (2.50 g, 8.11 mmol) and 4 A molecular sieves (1.50 g) in CH$_2$Cl$_2$ (100 mL) was added 3-trifluoromethyl benzaldehyde (1.4 mL, 10.5 mmol) via syringe followed by CF$_3$COOH (two drops). The mixture was allowed to warm to 10° C. and was stirred overnight. The suspended solids were removed by filtration through a pad of celite and the filtrate was concentrated in vacuo to provide a clear, viscous, yellow oil. The crude imine was dissolved in methanol (75 mL), cooled in an ice-water bath, and NaBH$_4$ (0.34 g, 8.92 mmol) was added in portions over 20 minutes. After the addition was complete the cooling bath was removed and the mixture was stirred at room temperature for four hours. The solvent was removed in vacuo and the resulting pale yellow, viscous oil was purified by chromatography on a column of silica gel (230–400 mesh, 500 g, 70 mm o.d., packed EtOAc-hexanes 10:90; eluted EtOAc-hexanes 20:80; 400 mL fractions) using the flash technique. Fractions 10–13 afforded 3.55 g, 97% of the title compound as a viscous oil.

Physical characteristics are as follows:
TLC: (Merck; EtOAc-hexanes, 1:3.
UV (+); ammonium molybdate): Rf=0.71.
$^1$H-NMR (300 MHz, CDCl$_3$): δ=7.05–7.61 (14), 5.26 (s, 2), 3.88(d, J=13.7 Hz, 1), 3.62 (t, J=6.6 Hz, 1), 3.59 (s, 3), 3.18 (m, 2), 2.10 (brs, 1).
$^{13}$C-NMR (75.5 MHz, CDCl$_3$): δ=174.8, 140.5, 137.4, 136.5, 131.4, 128.7, 127.6, 126.9, 126.7, 124.7, 123.7, 121.9, 119.3, 119.0, 110.0, 109.7, 61.4, 51.7, 51.6, 49.9, 29.3.
Infrared (neat): 3109, 2951, 1735, 1467, 1330, 1197, 1165, 1124, and 702 cm$^{-1}$.
EI/MS (70 eV): 467 (M+, 5.5), 407 (7.6), 220 (base).
Analysis: Calcd. for C$_{27}$H$_{25}$F$_3$N$_2$O$_2$: C, 69.52, H, 5.40; N, 6.01. Found: C, 69.28; H, 5.15; N, 5.85.

EXAMPLE 24

(D,L)-1-Phenylmethyltryptophan

A three-neck, one-liter flask equipped with a magnetic stir bath and placed in a dry ice-acetone bath was cooled to −78° C. while 370 mL of ammonia was condensed into the flask containing 163 mg of ferric nitrate nonahydrate. The external cooling bath was then removed and pieces of sodium metal (2.62 g, 114.3 mmol) were added portionwise over 30 minutes. After stirring for an additional 10 minutes (d,1)-tryptophan (10.0 g, 49.0 mmol) suspended in 110 mL of ether was added to the dark solution over a ten-minute period. The reaction mixture was allowed to stir for another 30 minutes at refluxing liquid ammonia temperature, treated with benzyl chloride (8.23 g, 65.3 mmol) over a five-minute period. The dry ice-acetone condenser was removed and the contents stirred overnight while a gentle stream of nitrogen was used to slowly removed the ammonia. The remaining residue was dissolved in 50 mL of hot water, acidified to pH 5 with 5 mL of acetic acid which produced a viscous white slurry. An additional 50 mL of water and 60 mL of 95% ethanol were added and the mixture was heated to reflux. The contents which remained mostly insoluble was cooled in an ice bath, the white solids collected and successively washed with cold ethanol-water (1:1), cold 95% ethanol and finally ether to provide 14.45 g of the title compound. This mixture was used in the next reaction without purification.

EXAMPLE 25

(D,L)-1-Phenylmethyltryptophan methyl ester

Hydrogen chloride gas was bubbled through 200 mL of methanol, cooled in an ice-acetone bath, over a 30-minute period. To this solution was added the title compound obtained in Example 24 (9.58 g) and the contents heated to reflux for five hours. The reaction mixture was cooled in an ice bath, the precipitated solids collected by filtration and washed with methanol-ether (1:1) to obtain 1.76 g of esters as their HCl salts. Concentration of the filtrate afforded an additional 8.60 g of product. The combined salts were treated with 1N aqueous NaOH and the aqueous solution was thoroughly extracted with ethyl acetate. The ethyl acetate was washed with brine, dried and concentrated in vacuo. Chromatography of the crude product using 125 g of silica gel and acetone-hexane as the eluent yielded 6.10 g of the title compound as a golden colored oil.

Physical characteristics are as follows:
Analysis: Calcd. for C$_{19}$H$_{20}$N$_2$O$_2$: 308. Found: 308.

EXAMPLE 26

(D,L)-1-Phenylmethyl-N-(3-trifluoromethyl)phenyl)-methyl-tryptophan methyl ester To 3.05 g of the (D,L)-1-phenylmethyl tryptophan methyl ester obtained in Example 24 dissolved in 100 mL of methanol, 1.60 mL of acetic acid, 1.72 g of metatrifluoromethyltolualdehyde, cooled to 15° C. with a cold water bath, was added 0.657 g of sodium cyanoborohydride. The cooling bath was removed after 15 minutes, the contents stirred at ambient temperature for an additional three hours and then treated with crushed ice after cooling the reaction mixture in an ice bath. The mixture was made basic with 100 mL of saturated sodium bicarbonate solution, extracted once with ethyl acetate, the ethyl acetate dried and then concentrated in vacuo. Chromatography of this crude product using 75 g of silica gel and ethyl acetate as the eluent afforded 2.10 g of the title compound.

Physical characteristics are as follows:
Analysis: Calcd. for C$_{27}$H$_{25}$F$_3$N$_2$O$_2$: C, 69.53; H, 5.36; N, 6.01. Found: C, 69.30; H, 5.44; N, 5.87.

EXAMPLE 27

(D,L)-1-Phenylmethyl-N-(3-(trifluoromethyl)phenyl)-methyl-tryptophan methyl ester HCl Salt To a magnetically stirred solution of (D,L)-1-phenylmethyl-N-(3-trifluoromethyl)phenyl)methyl-tryptophan methyl ester obtained in Example 26 (0.465 g) in 40 mL of ether cooled in a 0°–5° C. bath was bubbled HCl gas for two to three minutes. The white mass which precipitated was diluted with 10 mL of hexane, allowed to cool to 0°–5° C. and collected to give 478 mg of the title compound. A small sample was recrystallized with ethyl acetate-methanol-ether to give the title compound, m.p. 201°–203° C.

Physical characteristics are as follows:
Analysis: Calcd. for C$_{27}$H$_{25}$N$_2$O$_2$.HCl: C, 64.54; H, 4.98; N, 5.58, Found: C, 64.24; H, 5.41; N, 5.25.

EXAMPLE 28

(D,L)-1-Phenylmethyl-N-(3-(trifluoromethyl)phenyl)-methyl-Tryptophan

The methyl ester (1.00 g) isolated in Example 26 was treated with 20 mL of methanol and 4.00 mL of 1N sodium hydroxide and stirred at room temperature for 15 hours. The reaction was worked up in the usual way and chromatographed using 40 g of silica gel and chloroform-methanol (85:15) as the eluent to afford 808 mg of the title compound, m.p. 125° C.

Physical characteristics are as follows:
Analysis: Calcd. for C$_{26}$H$_{23}$F$_3$N$_2$O$_2$.H$_2$O: C, 66.38; H, 5.32; N, 5.96. Found: C, 66.20; H, 5.05; N, 5.74.

EXAMPLE 29

(D,L)-1-Ethylthiocarboxy-N-(3-(trifluoromethyl)-phenyl)methyl-tryptophan methyl ester A magnetically stirred solution of (D,L)-N-(3-(trifluoromethyl)methyl-tryptophan methyl ester (1.15 g, 3.06 mmol) in 15 mL of dimethylformamide, cooled to 18° C. was treated with 3.21 mmol of sodium hydride. The cooling bath was removed after five minutes, the contents stirred for another 45 minutes at room temperature, then reacted with ethyl thiochloroformate (0.419 g, 3.21 mmol) for an additional 40 minutes. The reaction mixture was then poured into 50 mL of crushed ice, extracted with ethyl acetate, the combined organic extracts dried over anhydrous sodium sulfate and concentrated in vacuo. The crude product was chromatographed using 150 g of silica gel and elution with ethyl acetate-hexane afforded 457 g of the title compound.

Physical characteristics are as follows:

H NMR (CDCl$_3$) 3.84 (d, 1 HO, 7.58 (s, 1H), 7.53–7.22 (m, 7H), 3.93 (d, 1 h), 3.76–3.66 (m, 1H), 3.68 (s, 3H), 3.66–3.58 (m, 1H), 3.18–2.98 (m, 4H), 1.43 (t, 3H).

EXAMPLE 30

(D,L)-1-Ethylthiocarboxy-N-(3-(trifluoromethyl)-phenyl)methyl-tryptophan methyl ester HCl Salt Utilizing a procedure similar to that described in Example 27 0.457 g of the methyl ester yielded 0.474 g of the title compound, m.p. 180°–181° C.

Physical characteristics are as follows:

Analysis: Calcd. for $C_{23}H_{23}F_3N_2O_3S.HCl$: C, 55.20; H, 4.80; N, 5.60. Found: C, 55.05; H, 4.62; N, 5.62.

Utilizing a procedure similar to those described previously there are obtained the following compounds:

DL-Methyl-1-(phenylmethyl)-tryptophan-methyl ester monohydrochloride.

Physical characteristics are as follows:

Analysis: Calcd. for $C_{19}H_{20}N_{O2}$-308: Found: M+308.

DL-N-1-bis(phenylmethyl)-tryptophan-methyl ester.

Physical characteristics are as follows:

Analysis: Calcd. for $C_{26}H_{26}N_2O_2$-398: Found: M+398.

Physical characteristics are as follows:

DL-1-(phenylmethyl)-tryptophan-N-[[3-(trifluoromethyl)phenyl]methyl]methyl ester.

Physical characteristics are as follows:

Analysis: Calcd. for $C_{27}H_{25}F_3N_2O_2$: C, 69.53; H, 5.36; N, 6.01. Found: C, 69.30; H, 5.44; N, 5.87.

DL-N-(1-methylethyl)-tryptophan-1-(phenylmethyl)methyl ester.

Physical characteristics are as follows:

Analysis: Calcd. for $C_{22}H_{26}N_2O_2$: C, 75.43; H, 7.43; N, 8.00. Found: C, 74.62; H, 7.41; N, 7.63.

DL-N-(1-methylethyl)-1-(phenylmethyl)-tryptophan-methyl ester, monohydrochloride, m.p. 207°–208° C.

Physical characteristics are as follows:

Analysis: Calcd. for $C_2H_{26}N_2O_2.HCl$: C, 68.39; H, 6.74; N, 7.25. Found: C, 68.19; H, 7.20; N, 7.01.

DL-1-(phenylmethyl)-N-[[[3-(trifluoromethyl)phenyl]methyl]tryptophan-methyl ester, monohydrochloride, m.p. 201°–203° C. (dec.).

Physical characteristics are as follows:

Analysis: Calcd. for $C_{27}H_{25}F_3N_2O_2.HCl$: C, 64.54; H, 4.98; N, 5.58. Found: C, 64.24; H, 5.41; N, 5.25.

DL-N-1-bis(phenylmethyl)-tryptophan, m.p. 185° C.

Physical characteristics are as follows:

Analysis: Calcd. for $C_{25}H_{24}N_2O_2.H_2O$: C, 74.63; H, 6.47; N, 6.97; Found: C, 74.50; H, 5.85; N, 6.59.

DL-1-(phenylmethyl)-N-[[3-(trifluoromethyl)phenyl]methyl]-tryptophan, m.p. 125° C.

Physical characteristics are as follows:

Analysis: Calcd. for $C_{25}H_{23}F_3N_2O_2.H_2O$: C, 66.38; H, 5.32; N, 5.96. Found: C, 66.20; H, 5.05; N, 5.74.

DL-Methylester-tryptophan monohydrochloride

DL-N-[[3-(triflouromethyl)phenyl]methyl]-tryptophan methyl ester

Physical characteristics are as follows:

Analysis: Calcd. for $C_{19}H_{19}F_3N_2O_2$ - 376. Found: M+376.

DL-1-p-(4-chlorophenyl)methyl]-N-[[3-(trifluoromethyl)phenyl]-methyl-tryptophan-methyl ester Physical characteristics are as follows:

Analysis: Calcd. for $C_{26}H_{24}F_3N_2O_2Cl$ - 500. Found: M+500.

DL-1-[(4-chlorophenyl)methyl]-N-[[3-(trifluoromethyl)phenyl]-methyl-tryptophan-methyl ester, m.p. 171°–172° C.

Physical characteristics are as follows:

Analysis: Calcd. for $C_{27}H_{24}ClF_3N_2O_2.HCl$: C, 60.45; H, 4.66; N,

Found: C, 60.05; H, 4.64; N, 5.05.

DL-N-[[(3-(trifluoromethyl)phenyl]methyl]-tryptophan-methyl ester, monohydrochloride, m.p. 172°–173° C.

Physical characteristics are as follows:

Analysis: Calcd. for $C_{20}H_{19}F_3N_2O_2.HCl$: C, 58.25; H, 4.85; N, 6.80. Found: C, 58.21; H, 4.89; N, 6.82.

DL-1-[(ethylthio)carbonyl]-N-[[3(trifluoromethyl)phenyl]methyl]-tryptophan

DL-1-[(ethylthiocarbonyl]-N-[[3-(trifluoromethyl)phenyl]methyl]-tryptophan monohydrochloride, m.p. 180°–181.5° C.

Physical characteristics are as follows:

Analysis: Calcd. for $C_{23}H_{23}F_3N_2O_3S.Hcl$: C, 55.20; H, 4.80; N, 5.60. Found: C, 55.05; H, 4.62; N, 5.61.

DL-1-(ethoxycarbonyl)-N-[[3-(trifluoromethyl)phenyl]methyl]-tryptophan methyl ester.

DL-1-(ethoxycarbonyl)-N-[[3-(trifluoromethyl)phenyl]methyl]-tryptophan-methyl ester, monohydrochloride, m.p. 189°–190° C.

Physical characteristics are as follows:

Analysis: Calcd. for $C_{23}H_{23}F_3N_2O_4.HCl$: C, 57.02; H, 4.96; N, 5.79. Found: C, 56.85; H, 5.08; N, 5.92.

DL-N-[[3-(trifluoromethyl)phenyl]methyl]-tryptophan, m.p. 227° C.

Physical characteristics are as follows:

Analysis: Calcd. for $C_{19}H_{17}F_3N_2O_2.H_2O$: C, 60.00; H, 5.00; N, 7.37. Found: C, 60.43; H, 4.80; N, 7.287.

D-N-(phenylmethyl)-tryptophan.

D-N-(phenylmethyl)-tryptophan-methyl ester.

D-1-(phenylmethyl)-N-[[3-(trifluoromethyl)phenyl]-methyl]-tryptophan-methyl ester.

D-1-(phenylmethyl)-N-[[3-(trifluoromethyl)phenyl]-methyl]-tryptophan-methylester monohydrochloride, m.p. 171°–172° C.

Physical characteristics are as follows:

Analysis: Calcd. for $C_{27}H_{25}F_3N_2O_2.HCl$: C, 64.54H, 4.98; N, 5.58. Found: C, 64.28; H, 5.13; N, 5.19

D-1-(phenylmethyl)-N-[[3-(trifluoromethyl)phenyl]-methyl-tryptophan, m.p. 170°–173° C.

Physical characteristics are as follows:

Analysis: Calcd. for $C_{26}H_{23}F_3N_2O_2$: C, 69.03; H, 5.09; N, 6.19. Found: C, 68.70; H, 5.29; N, 6.37.

EXAMPLE 31

Methyl (+/−)-α-(1-phenylmethyl-3-indolylmethyl)aminophenylacetate (see Chart III for preparation of Examples 31–40)

To a suspension of methyl (+/−)-phenylglycinate hydrochloride (4.00 g, 19.8 mmol) in MeOH (50 mL), and HOAc (4 mL) was added 1-phenylmethyl-indole-3-carboxaldehyde (2.85 g, 12.1 mmol). The resulting mixture was allowed to stir at room temperature for 20 minutes; then NaBH$_3$CN (1.98 g, 31.5 mmol) was added in one portion. The suspension was allowed to stir at room temperature for 18 hours, then was concentrated in vacuo to furnish a sticky white semi-solid. The crude reaction mixture was partitioned between 20% aqueous NaOH (0.25 L) and EtOAc (0.25 L); the organic phase was separated, washed with brine (0.25 L), and dried (Na$_2$SO$_4$). Concentration in vacuo afforded the crude product as a pale green oil which was purified by chromatography on a column of silica gel (230–400 mesh, 500 g, 70 mm o.d., EtOAc-hexanes 25:75, 400 mL fractions) using the flash technique. Fractions 8–13 were combined to provide 2.0 g (43%) of the title compound as a white solid. Recrystallization from EtOAc-hexanes provided white needles, m.p. 109°–110° C.

Physical characteristics are as follows:

TLC (Merck; EtOAc-hexanes, 25:75.

UV(+); ammonium molybdate) Rf=0.48.

1H-NMR: δ=7.67 (d, J=7.23 Hz, 1), 7.05–7.45 (15), 5.28 (s,2), 4.49 (s, 1), 3.94 (s, 2), 3.67 (s, 3).

Infrared (nujol): 2925, 2855, 1733, 1453, 1442, 1333, 1208, 1176, 790, and 737 cm$^{-1}$.

EI/MS (70 eV): 384 (M+, 17.8), 325 (6.0), 235 (7.9), 220 (base), 129 (14.2), 91 (75.8).

Analysis: Calcd. for C$_{25}$H$_{24}$N$_2$O$_2$: C, 78.10; H, 6.29; N, 7.29.

Found: C, 78.07; H, 6.48, N, 7.23.

EXAMPLE 32

Methyl (R)-α-(1-phenylmethyl-3-indolylmethyl)aminophenylacetate

According to the general procedure described for the preparation of Example 31, methyl (R)-phenylglycinate-hydrochloride (4.00 g, 19.8 mmol), 1-benzyl-indole-3-carboxaldehyde (2.33 g, 9.9 mmol) and NaBH$_3$CN (0.81 g, 12.9 mmol) provided crude title compound as a pale yellow oil. The crude material was purified by chromatography on a column of silica gel (230–400 mesh, 500 g, 70 mm o.d., packed-ethyl acetate-hexanes 20:80, eluted ethyl acetate-hexanes 25:75, 400 mL fractions) using the flash technique. Fractions 8.13 provided 2.82 g (74%) of the title compound as a pale yellow oil which slowly crystallized to an ivory solid, m.p. 72°–75° C.

Physical characteristics are as follows:

TLC (Merck: EtOAc-hexanes, 35:65.

UV(+); ammonium molybdate) Rf=0.30.

1H-NMR: δ=7.67 (d, J=7.32 Hz, 1), 7.05–7.45 (15), 5.27 (s, 2), 4.48 (s, 1), 3.94 (s, 2), 3.66 (s, 3).

13C-NMR: δ=173.1, 138.1, 137.5, 136.6, 128.7, 128.6, 128.0, 127.6, 126.8, 121.9, 119.3, 113.5, 109.7, 64.6, 52.1, 49.9, 42.5.

Infrared (nujol): 2924, 2855, 1733, 1453, 1443, 1333, 1208, 1176, 790, and 737 cm$^{-1}$.

EI/MS (70 eV): 384 (M+, 11.9), 325 (6.1), 235 (8.0), 220 (base), 129 (10.9), 91 (76.5).

Analysis: Calcd. for C$_{25}$H$_{24}$N$_2$O$_2$: C, 78.10; H, 6.29; N, 7.29.

Found: C, 77.82; H, 6.15, N, 7.28.

EXAMPLE 33

Methyl (S)-α-(1-phenylmethyl-3-indolylmethyl)aminophenylacetate.

According to the general procedure described for the preparation of Example 31, methyl (S)-phenylglycinate-hydrochloride (4.00 g, 19.8 mmol), 1-benzyl-indole-3-carboxaldehyde (2.33 g, 9.9 mmol) and NaBH$_3$CN (0.81 g, 12.9 mmol) provided crude title compound as a pale yellow oil. The crude material was purified by chromatography on a column of silica gel (230–400 mesh, 500 g, 70 mm o.d., packed-ethyl acetate-hexanes 20:80, eluted ethyl acetate-hexanes 25:75, 400 mL fractions) using the flash technique. Fractions 7–12 provided 1.44 g (38%) of the title compound as a clear, pale yellow oil.

Physical characteristics are as follows:

TLC (Merck; EtOAc-hexanes, 35:65.

UV(+); ammonium molybdate) Rf=0.30.

1H-NMR: δ=7.67 (d, J=7.23 Hz, 1), 7.05–7.45 (15), 5.24 (s,2), 4.48 (s,1), 3.97 (s, 2), 3.66 (s, 3).

13C-NMR: δ=173.1, 138.1, 137.5, 136.6, 128.7, 128.6, 128.0, 127.6, 126.8, 121.9, 119.3, 113.5, 109.7, 64.6, 52.1, 49.9, 42.5.

Infrared (nujol): 2954, 2855, 1734, 1453, 1443, 1333, 1208, 1176, 790, and 737 cm$^{-1}$.

EI/MS (70 eV): 384 (M+, 12.4), 325 (6.9), 235 (8.3), 220 (base), 129 (9.5), 91 (70.4).

Analysis: Calcd. for C$_{25}$H$_{24}$N$_2$O$_2$: C, 78.10; H, 6.29; N, 7.29.

Found: C, 77.798; H, 6.47, N, 7.24.

EXAMPLE 34

Methyl (+/−)-α-(1-phenylmethyl-3-indolylmethyl)amino-(3-trifluoromethylphenyl) acetate According to the general procedure described for the preparation of Example 31, (+/−)-3-trifluoromethyl-phenylglycine methyl ester (2.74 g, 11.8 mmol), 1-benzyl-indole-3-carboxaldehyde (1.38 g, 5.88 mmol) and NaBH3CN (0.48 g, 7.64 mmol) provided crude title compound as a clear, pale yellow oil. The crude material was purified by chromatography on a column of silica gel (230–400 mesh, 500 g, 70 mm o.d., ethyl acetate-hexanes 25:75, 400 mL fractions) using the flash technique. Fractions 8–12 afforded 2.29 g (86%) of the title compound as a clear, pale yellow oil.

Physical characteristics are as follows:

TLC (Merck; EtOAc-hexanes, 50:40.

UV(+); ammonium molybdate) Rf=0.12.

1H-NMR: δ=700–7.70 (14), 5.26 (s, 2), 4.53 (s, 1), 3.97 (d, J=13.3 Hz, 1), 3.92 (d, J=13.3 Hz, 1), 3.66 (s, 3), 2.31 (br, 1).

13C-NMR: δ=173.0, 139.7, 137.4, 136.7, 131.1, 130.5, 129.1, 128.7, 127.7, 127.0, 126.9, 124.9, 124.6, 122.0, 119.4, 119.2, 112.4, 109.8, 64.0, 52.4, 50.0, 42.6.

Infrared (CHCl$_3$): 3060, 3032, 2954, 2925, 1739, 1496, 1467, 1454, 1437, 1331, 1200, 1167, 1125, 1074, 812, 790, and 742 cm$^{-1}$.

EI/MS (70 eV): 452 (M+, 20.7), 235 (10.6), 220 (base), 129 (16.8), 91 (96.6).

Analysis: Calcd. for $C_{26}H_{23}F_3N_2O_2$: C, 69.02; H, 5.12; N, 6.19. Found: C, 68.79; H, 5.19, N, 6.09.

EXAMPLE 35

Methyl (R)-α-(3-indolylmethyl)amino-phenylacetate

According to the general procedure described for the preparation of Example 31, methyl (R)-phenylglycinate-hydrochloride (2.50 g, 12.4 mmol), indole-3-carboxaldehyde (0.81 g, 6.2 mmol) and NaBH$_3$CN (0.51 g, 8.06 mmol) provided crude title compound as a cloudy, pale brown oil. The crude material was purified by chromatography on a column of silica gel (230-400 mesh, 400 g, 70 mm o.d., packed-ethyl acetate-hexanes 10:90, eluted ethyl acetate-hexanes (10:90 2 L), (20:80, 2 L), (30:70, 2 L), (40:60, 2 L), (50:50, 2 L), (60:40, 2 L), 400 mL fractions) using the flash technique. Fractions 28-29 provided 0.19 g (10%) of the title compound as a tan solid, m.p. 115°-118° C.

Physical characteristics are as follows:

TLC (Merck; EtOAc-hexanes, 35:65.

UV(+); ammoniummolybdate) Rf=0.15.

1H-NMR: δ=8.20 (brs, 1), 7.65 (d, J=7.7 Hz, 1), 7.0-45 (9), 4.49 (s, 2), 3.94 (s, 2), 3.66 (s, 3), 2.16 (br, 1).

13C-NMR: δ=173.7, 138.1, 136.5, 128.7, 128.1, 127.7, 126.9, 122.9, 122.1, 119.6, 119.0, 114.0, 111.2, 64.6, 52.2, 42.6.

Infrared (CHCl$_3$): 2955, 2925, 2871, 2857, 1733, 1717, 1456, 1452, 1435, 1347, 1283, 1242, 1171, 1108, 1017, 838, 744, and 737 cm$^{-1}$.

EI/MS (70 eV): 294 (M+, 8.1), 235 (22.2), 130 (base), 106 (62.8).

Analysis: Calcd. for $C_{18}H_{18}N_2O_2$: C, 73.45; H, 6.16; N, 9.52. Found: C, 73.46; H, 6.37, N, 9.49.

EXAMPLE 36

Methyl (S)-α-(3-indolylmethyl)amino-phenylacetate

According to the general procedure described for the preparation of Example 31, methyl (S)-phenylglycinate-hydrochloride (2.50 g, 12.4 mmol), indole-3-carboxaldehyde (0.81 g, 6.2 mmol) and NaBH$_3$CN (0.51 g, 8.06 mmol) provided crude title compound as a cloudy, pale brown oil. The crude material was purified by chromatography on a column of silica gel (230-400 mesh, 400 g, 70 mm o.d., packed-ethyl acetate-hexanes 30:70, eluted ethyl acetate-hexanes 40:60, 400 mL fractions) using the flash technique. Fractions 12-13 provided 0.13 g (7%) of the title compound as a tan solid, m.p. 120° C. (dec.).

Physical characteristics are as follows:

TLC (Merck; EtOAc-hexanes, 35:65.

UV(+); ammonium molybdate) Rf=0.15.

1H-NMR: δ=8.15 (brs, 1), 7.65 (d, J=7.7 Hz, 1), 7.0-7.45 (9), 4.49 (s, 2), 3.94 (s, 2), 3.67 (s, 3), 1.97 (br, 1).

13C-NMR: δ=173.5, 138.4, 136.5, 128.4, 127.8, 127.4, 126.7, 122.6, 121.9, 119.3, 118.8, 113.7, 110.9, 64.2, 51.8, 42.3.

Infrared (nujol): 2953, 2926, 2868, 2855, 1727, 1694, 1455, 1429, 1349, 1281, 1171, 1108, 1017, 834, and 743 cm$^{-1}$.

EI/MS (70 eV): 294 (M+, 5.7), 235 (21.8), 130 (base), 106 (77.6).

Analysis: Calcd. for $C_{18}H_{18}N_2O_2$: C, 73.45; H, 6.16; N, 9.52.

Found: C, 73.43; H, 6.31, N, 9.60.

EXAMPLE 37

Methyl (+/−)-α-(1-phenylmethyl-5-methoxy-3-indolylmethyl) amino-(3-trifluoromethylphenyl)acetate According to the general procedure described for the preparation of Example 31, (+/−)-3-trifluoromethyl-phenylglycine methyl ester (2.66 g, 11.4 mmol), 1-benzyl-5-methoxyindole-3-carboxaldehyde (1.00 g, 5.71 mmol) and NaBH$_3$CN (0.47 g, 7.42 mmol) provided crude title compound as a clear, pale yellow oil. The crude material was purified by chromatography on a column of silica gel (230-400 mesh. 500 g, 70 mm o.d., ethyl acetate-hexanes 35:65, 400 mL fractions) using the flash technique. Fractions 4-5 afforded 1.22 g (54%) of the title compound as a clear, viscous, pale yellow oil.

Physical characteristics are as follows:

TLC (Merck; EtOAc-hexanes, 35:65.

UV(+); ammonium molybdate) Rf=0.35.

1H-NMR: δ=7.69 (s, 1), 7.57 (brt, J=8 Hz, 2), 7.45 (t, J=8 Hz, 1), 7.27 (m, 3), 7.11 (m, 4), 7.00 (s, 1), 6.83 (dd, J=8.8, 2.5 Hz, 1), 5.23 (s, 2), 4.54 (s, 1), 3.91 (brs, 2), 3.84 (s, 3), 3.68 (s, 3).

13C-NMR: δ=172.7, 154.0 139.3, 137.6, 132.2, 130.9, 128.9, 128.6, 127.5, 126.7, 125.0, 124.6, 112.3, 110.5, 100.8, 63.9, 55.7, 52.3, 50.1, 42.6.

Infrared (CHCl$_3$): 2952, 2926, 2835, 1738, 1621, 1581, 1488, 1453, 1437, 1354, 1330, 1261, 1227, 1207, 1167, 1125, 1098, 1074, 1042, 796, 780, 736, and 702 cm$^{-1}$.

EI/MS (70 eV): 482 (M+, 22.9), 250 (base), 159 (16.2), 91 (86.1).

Analysis: Calcd. for $C_{27}H_{25}F_3N_2O_3$: C, 67.21; H, 5.22; N, 5.81.

Found: C, 67.27; H, 5.30, N, 5.86.

EXAMPLE 38

Methyl-(+/−)-a-(5-methoxy-3-indolylmethyl)amino-(3-trifluoromethylphenyl) acetate According to the general procedure described for the preparation of Example 31, (+/−)-3-trifluoromethyl-phenylglycine methyl ester (5.99 g, 25.7 mmol), 5-methoxyindole-3-carboxaldehyde (1.50 g, 8.56 mmol) and NaBH$_3$CH (0.70 g, 11.1 mmol) provided crude title compound as a clear, pale yellow oil. The crude material was purified by chromatography on a column of silica gel (230-400 mesh, 500 g, 70 mm o.d., packed ethyl acetate-hexanes 30:70, eluted ethyl acetate-hexanes 40:60, 400 mL fractions) using the flash technique. Fractions 5-8 afforded 2.50 g (74%) of the title compound as a clear, viscous, pale yellow oil.

Physical characteristics are as follows:

TLC (Merck; EtOAc-hexanes, 50:50.

UV(+); ammonium molybdate) Rf=0.35.

1H-NMR: δ=7.70 (s, 1), 7.57 (dd, J=10.0, 7.6 Hz, 2), 7.45 (m, 2), 7.21 (d, J=8.80 Hz, 1), 7.21 (dd, J=11.2, 2.46 Hz, 1), 6.86 (dd, J=8.80, 2.46 Hz, 1), 4.54 (s, 1), 3.91 (s, 2), 3.84 (s, 3), 3.68 (s, 3).

13C-NMR: 67=172.8, 154.0, 139.3, 131.4, 130.9, 129.0, 127.3, 124.8, 124.4, 123.6, 122.3, 113.4, 112.5, 111.8, 100.6, 63.9, 55.7, 52.3, 50.1, 42.7.

Infrared (CHCl$_3$): 3409, 2953, 2833, 1738, 16214, 1586, 1487, 1454, 1441, 1331, 1301, 1239, 1214, 1167, 11225, 1098, 1073, 1028, 922, 831, 800, and 703 cm$^{-1}$.

EI/MS (70 eV): 392 (M+, 7.2), 174 (9.3), 160 (base), 145 (12.1), 117 (10.5).

Analysis: Calcd. for $C_{27}H_{25}F_3N_2O_3$: 392.1348. Found: 392.1336

EXAMPLE 39

Methyl (R)-α-(1-phenylmethyl-5-methoxy-3-indolylmethyl) amino-phenylacetate.

According to the general procedure described for the preparation of Example 31, methyl (R)-phenylglycinate-hydrochloride (1.52 g, 7.54 mmol), 1-benzyl-5-methoxy-indole-3-carboxaldehyde (1.00 g, 3.77 mmol) and NaBH3CH (0.31 g, 4.91 mmol) provided crude title compound as a pale yellow oil. The crude material was purified by chromatography on a column of silica gel (230-400 mesh, 500 g, 70 mm o.d., ethyl acetate-hexanes 35.65, 400 mL fractions) using the flash technique. Fractions 6-10 provided 0.74 g (47%) of the title compound as a pale yellow, viscous oil.

Physical characteristics are as follows:

TLC (Merck; EtOAc-hexanes, 35.65.

UV(+); ammonium molybdate) Rf=0.27.

1H-NMR; $\delta=7.05-7.45$ (12), 7.02 (s, 1), 6.82 (dd, J=8.8, 2.5 Hz, 1), 5.22 (s, 2), 4.49 (s, 1), 3.90 (s, 2), 3.83 (s, 3), 3.67 (s, 3), 2.08(br, 1).

13C-NMR: $\delta=173.6$, 154.2, 138.3, 137.3, 132.0, 128.6, 128.5, 127.9, 127.5, 127.4, 126.7, 112.3, 112.1, 110.4, 100.9, 64.4, 55.7, 52.0, 50.1, 42.4.

Infrared (CHCl3): 3030, 2950, 2924, 1736, 1581, 1488, 1453, 1436, 1313, 1262, 1227, 1210, 1176, 1130, 1041, 1029, 796, 778, 735, and 702 cm$^{-1}$.

EI/MS (70 eV): 414 (M+, 18.0), 250 (base), 91 (63.5).

Analysis: Calcd. for $C_{26}H_{26}N_2O_3$: C, 75.34; H, 6.32; N, 6.76.

Found: C, 75.12; H, 6.48, N, 6.78.

EXAMPLE 40

Methyl-(S)-a-(1-phenylmethyl-5-methoxy-3-indolylmethyl) amino-phenylacetate

According to the general procedure described for the preparation of Example 31, methyl (S)-phenylglycinate-hydrochloride (3.04 g, 15.1 mmol), 1-benzyl-5-methoxy-indole-3-carboxaldehyde (2.00 g, 7.54 mmol) and NaBH$_3$CN (0.62 g, 9.80 mmol) provided crude title compound as a pale yellow oil. The crude material was purified by chromatography on a column of silica gel (230-400 mesh, 500 g, 70 mm o.d., packed ethyl acetate-hexanes 25:75, eluted ethyl acetate-hexanes 30:70, 400 mL fractions) using the flash technique. Fractions 8-14 provided 2.18 g (70%) of the title compound as a pale yellow, viscous oil.

Physical characteristics are as follows:

TLC (Merck; EtOAc-hexanes, 50:450.

UV(+); ammonium molybdate) Rf=0.42.

1H-NMR: $\delta=7.05-7.45$ (12), 7.02 (s, 1), 6.82 (dd, J=8.8, 2.5 Hz, 1), 5.21 (s,2), 4.49 (s, 1), 3.90 (s, 2), 3.83 (s, 3), 3.66 (s, 3), 2.23 (br, 1).

13C-NMR: $\delta=173.5$, 153.8, 138.2, 137.5, 132.0, 128.6, 128.5, 127.9, 127.6, 127.5, 126.7, 112.7, 112.1, 110.4, 100.9, 64.4, 55.7, 52.1, 50.0, 42.5.

Infrared (CHCl3): 3030, 2950, 2925, 1735, 1581, 1488, 1453, 1436, 1313, 1262, 1227, 1209, 1176, 1130, 1042, 1029, 796, 778, 735, and 700 cm$^{-1}$.

EI/MS (70 eV): 414 (M+, 15.5), 250 (base), 91 (63.5).

Analysis: Calcd. for $C_{26}H_{26}N_2O_3$: C, 75.34; H, 6.32; N, 6.76. Found: C, 75.06; H, 6.22, N, 6.80.

The compounds of this invention are useful as anti-diabetic, anti-obesity and anti-atherosclerotic agents. While all of the compounds do not have all of the activities the utility of a particular compound can be determined by one skilled in the art utilizing the various tests.

Anti-diabetic

A. Testing For Blood Glucose Lowering In the KKA$^y$ Mouse

All KKA$^y$ mice used for screening are produced and selected by methods outlined by T. Fujita et al., Diabetes, 32, pp. 804-10 (1983). The screening is done in groups of six animals per group.

Pre-treating non-fasting blood glucose (NFBG) samples are measured five days prior to the start of a screening run by previously described methodologies. These blood sugar values are used to place animals into groups with equal mean blood glucose concentrations and to eliminate any mice with a NFBG value <250 mg/dl. On day 0, compounds chosen to be run are incorporated into ground mouse chow (Purina 5015). Compounds are included at a rate of 1 mg/gram of chow. Generally, 300 g of drugs containing diet is prepared for each group. Mice receiving ground chow only are the negative control.

Each screening run also uses ciglitazone (T. Fujita et al., supra) as a positive control (0.5 to 1.0 mg/gram chow).

Initial body and food weights are taken on day one. Food is placed in a crock which contains an adequate amount to last for the length of the study. In order to acclimate the mice for pelleted mouse chow to ground mouse chow, they are fed the ground chow for nine days prior to use in the screen. On day four of treatment, a NFBG sample is again measured, as well as food and body weights. Food consumption measurements are used to determine an average mg/kg dose the mice received over the testing period, and to evaluate the compounds's effect on food consumption.

Acceptance and activity are determined by the following criteria:

A. Negative Control

This group must not show a significant change (p<0.05) from pre- to post-treatment. If there is a significant decreased in blood sugar, the run is not valid.

B. Positive Control

This group must show a significant depression in blood sugar mean levels from pre- to post-treatment. A lack of activity in this group would also invalidate the run.

C. Negative Control vs. Positive Control

This contrast must be significant. It is a further assurance that both control groups performed as expected.

D. Compound

A compound's activity is based on several criteria:

1. A significant decrease in blood sugar mean levels from pre- to post-treatment.

2. Negative control vs. compound: This contrast allows one to determine if these groups are dissimilar, which is required for the compound to be considered active.

II. Anti-obesity Activity

Upjohn Sprague-Dawley rats are housed individually and given food and water ad libitum. Food consumption is measured daily. The animals are orally dosed with 100 mg/kg or 200 mg/kg of the compound in Tween 80. controls receive an equivalent volume of Tween 80. If the daily food consumption of the treated animals is in the range of 4 grams less than that of the control animals the compound is considered to have anorexic activity.

III. Anti-atherosclerotic activity
Normocholesterolemic Quail Lipoprotein Test Male SEA Japanese quail, approximately four to six weeks of age are used from a colony of animals originally derived at The Upjohn Company. Prior to drug testing, birds are randomly distributed into 10–15 groups of 10 quail each. They are housed individually in 10-cage units and fed a commercial diet (Purina Game Bird Layena, Ralston Purina Co., St. Louis, Mo.) for seven days. Compounds (0.5 g for 50 mg/kg dose, 0.15 g for 15 mg/kg dose, 0.05 g for 5 mg/kg dose, etc.) are dissolved or dispersed in 50 mL of 95% ethanol and mixed with 1.2 kg of the diet. Control groups receive diet mixed with ethanol alone, and positive control groups receive diet mixed with 1-propyl-2(1H)-pyridinone at 50 mg/kg.

After one week on the diets, each bird is bled from the right jugular vein and serum samples are obtained after low speed centrifugation. Food intake is determined for each group by subtracting the weight of diet remaining at the end of the experiment from the weight of the starting diet.

Beta- and alpha-lipoproteins are isolated from individual serum samples using PEG-8000 and glycine buffer, pH 9. three hundred microliters of serum are mixed with 300 microliters of solution A (20 gram of PEG-8000+100 mL of glycine buffer, pH 9) using a Micromedia automatic pipette. Samples are allowed to stand at room temperature for 10 minutes and are centrifuged for 20 minutes at 2000×g at 4° C. The beta-lipoprotein pellet is dissolved in 300 microliters of solution B (10 mL Triton X-100+1000 mL Milli Q water). Cholesterol, triglycerides and total protein in alpha- and beta-lipoproteins are measured using the Demand Autoanalyzer system Model AU 500 (Cooper Biomedical Inc.) and Worthington Demand Enzymatic reagents (Pearson, G. W. et al, Biometrika 38, (1951) pp. 112–130).

All data is statistically analyzed using a one-way classification design. All values are transformed to logarithms to achieve more homogenous within-group variances. The mean response for each test compound is compared with the mean observed in the control animals by the LSD test (Snedecor, G. W. et al (1969), Statistical Methods, ISV Press, Ames, Iowa, pp. 258–296). Treated/control ratios of antilogs of the log means are presented. A P-value less than 0.004 is significantly different from control.

Compounds that reduce beta-lipoproteins and/or increase alpha-lipoproteins are considered to be indicative of anti-atherosclerotic activity.

TABLE 1

| Name | KKay Mouse Insulin Sensitizing Screen 1st Stage[a] | KKay Mouse Insulin Sensitizing Screen 2nd Stage[b] | Single Dose in KKAy Mouse[c] (50 mg/kg) | Body Weight Change in KKAy mouse[d] 1st Stage | Body Weight Change in KKAy mouse[d] 2nd Stage | Single Dose | Normal Quail[e] HDL | Normal Quail[e] LDL | Normal Rat[e] HDL | Normal Rat[e] LDL |
|---|---|---|---|---|---|---|---|---|---|---|
| 1 | + | + | | ↓ | ↑ | | | | | |
| 2 | − | | | ↓ | | | | | | |
| 3 | + | − | | | ↓ | | | | | |
| 4 | + | + | + | ↓ | ↓ | ↓ | ↑↑ | →↓ | ↑ | ↑ |
| 5 | | | + | | | ↓ | | | | |
| 6 | | | | | | | | | | |
| 7 | + | | + | ↓ | | ↓ | | | →↓ | →↑ |
| 8 | + | | + | ↓ | | ↓ | ↑ | ↑ | | |
| 9 | + | | + | ↓ | | ↓ | ↑ | → | | |
| 10 | + | | | ↓ | | | | | | |
| 11 | + | | | ↓ | | | ↑ | → | | |
| 12 | + | | | ↑ | | | | | | |
| 13 | − | | | ↓ | | | | | | |
| 14 | − | | | ↓ | | | → | → | | |
| 15 | | | − | | | ↓ | → | → | | |
| 16 | + | | + | ↓ | | ↓ | | | | |
| 17 | | | − | | | | | | | |
| 18 | | | + | | | ↓ | | | | |
| 19 | | | + | | | ↓ | | | | |
| 20 | | | ± | | | ↑ | | | | |
| 21 | | | + | | | ↓ | | | | |
| 22 | | | + | | | ↓ | | | | |
| 23 | | | − | | | ↓ | | | | |
| 24 | | | ± | | | ↓ | | | | |
| 25 | | | ± | | | ↓ | | | | |
| 26 | | | − | | | ↓ | | | | |
| 27 | | | + | | | ↓ | | | | |
| 28 | | | + | | | ↓ | | | | |
| 29 | | | + | | | ↓ | | | | |
| 30 | + | | + | ↓ | | ↓ | | | | |
| 31 | + | | + | ↓ | | ↓ | | | | |
| 32 | | | − | | | ↓ | | | | |
| 33 | | | + | | | ↓ | | | | |
| 34 | | | + | | | ↓ | | | | |
| 35 | | | + | | | ↓ | | | | |
| 36 | | | + | | | ↓ | | | | |
| 37 | | | + | | | ↓ | | | | |
| 39 | | | + | | | ↓ | | | | |
| 39 | | | + | | | ↓ | | | | |
| 40 | | | + | | | ↓ | | | | |
| 41 | | | − | | | ↓ | | | | |
| 42 | | | − | | | ↓ | | | | |

TABLE 1-continued

| Name | KKAy Mouse Insulin Sensitizing Screen | | Single Dose in KKAy Mouse[c] (50 mg/kg) | Body Weight Change in KKAy mouse[d] | | Single Dose | Normal Quail[e] | | Normal Rat[e] | |
|---|---|---|---|---|---|---|---|---|---|---|
| | 1st Stage[a] | 2nd Stage[b] | | 1st Stage | 2nd Stage | | HDL | LDL | HDL | LDL |
| 43 | | | + | ↓ | | | | | | |
| 44 | | | + | | | | | | | |
| 45 | | | − | ↓ | | | | | | |
| 46 | | | + | ↓ | | | | | | |
| 47 | | | + | | | | | | | |
| 49 | | | ± | | | | | | | |

[a]+ signifies a T/C value of 0.85 or lower.
− signified a T/C value of 0.85 or higher.
[b]+ signified a T/C stage 1 × T/C stage 2 value of 0.61 or lower.
− signifies a T/C stage 1 × T/C stage 2 value of 0.62 or higher.
[c]+ signifies a significant lowering of blood glucose compared to non-treated control animals.
± signifies a modest lowering of blood glucose compared to non-treated control animals.
− signifies no change or an increase of blood glucose compared to non-treated control animals.
[d]↑ signifies an increase in body weight from before treatment to after treatment.
↓ signifies a decrease in body weight from before treatment to after treatment.
[e]↑ signifies an increase in HDL or LDL compared to non-treated control animals.
↓ signifies a decrease in HDL or LDL compared to non-treated control animals.
→ signifies no change in HDL or LDL compared to non-treated control animals.

KEY TO NAME OF COMPOUND;

1. Methyl α-aminoindole-3-acetate
2. Methyl α-[(2-(4-aminosulfonylphenyl)-ethylamino]-indole-3-acetate hydrate (1:1)
3. Methyl α-[3(trifluoromethyl)benzylamino]-5-methoxyindole-3-acetate
4. α-[3-(Trifluoromethyl)benzylamino]-1-benzylindole-3-acetic acid
5. α-[3-(Trifluoromethyl)benzylamino]-1-benzylindole-3-acetic acid hydrochloride
6. Sodium α-[3-(trifluoromethyl)benzyl-amino]-1-benzylindole-3-acetate
7. Methyl α-[3-(trifluoromethyl)benzylamino]-1-benzylindole-3-acetate hydrochloride
8. α-[3-(Trifluoromethyl)benzylamino]-1-methylindole-3-acetic acid
9. α-Benzylamino-1-benzylindole-3-acetic acid
10. α-(4-Chlorobenzylamino)-1-benzylindole-3-acetic acid
11. α-[(3-Pyridinylmethyl)amino-1-benzylindole-3-acetic acid
12. α-(4-Methoxybenzylamino)-1-benzylindole-3-acetic acid
13. α-[(4-henylbutyl)amino]-1-benzylindole-3-acetic acid
14. α-[(S)-α-methylbenzylamino]-1-benzylindole-3-acetic acid
15. α-[3-(Trifluoromethyl)benzylamino]-1-(4-chlorobenzyl)-indole-3-acetic acid
16. α-[3-(Trifluoromethyl)benzylamino]-1-phenylindole-3-acetic acid
17. N-Benzyl-1-benzyltryptophan hydrate (1:1)
18. N-Benzyl-1-benzyltryptophan methyl ester
19. N-[3-(Trifluoromethyl)benzyl]-1-benzyltryptophan methyl ester hydrochloride
20. α-[(2-Phenylethyl)amino]-1-benzylindole-3-acetic acid hydrate (1:1)
21. α-[3-(Trifluoromethyl)benzylamino]-1-benzyl-2-phenylindole-3-acetic acid
22. α-[3-(Trifluoromethyl)benzylamino]-1-benzyl-5-methoxyindole-3-acetic acid
23. α-(N-Methylbenzylamino)-1-benzylindole-3-acetic acid hydrate (4:1)
24. α-[3-(Trifluoromethyl)benzylamino]-1-benzyl-5-chloroindole-3-acetic acid
25. Methyl α-[3-(trifluoromethyl)benzylamino]-1-methyl-2-methylindole-3-acetate hydrochloride
26. Methyl α-[3-(trifluoromethyl)benzylamino]-1-benzyl-2-methylindole-3-acetate hydrochloride
27. α-[3-(Trifluoromethyl)benzylamino]-1-allylindole-3-acetic acid
28. Ethyl-60-[3-(trifluoromethyl)benzylamino]-1-benzylindole-3-acetate hydrochloride
29. Methyl α-[N-methyl-3-(trifluoromethyl)benzylamino]-1-benzylindole-3-acetate hydrochloride
30. α-[3-(Trifluoromethyl)benzylamino]indole-3-acetic acid
31. Ethyl α-[3-(Trifluoromethyl)benzylamino]-indole-3-acetate
32. Ethyl α-[3-Trifluoromethyl)benzylamino]-indole-3-acetate hydrochloride
33. Benzyl α-[3-(Trifluoromethyl)benzylamino]-1-benzylindole-3-acetate hydrochloride
34. Ethyl α-[3-(trifluoromethyl)benzylamino]-1-ethoxycarbonylindole-3-acetate hydrochloride
35. α-[4-(Trifluoromethyl)benzylamino]-1-benzylindole-3-acetic acid
36. α-[3,5-bis(Trifluoromethyl)benzylamino]-1-benzylindole-3-acetic acid
37. α-(4-Methylbenzylamino)-1-benzylindole-3-acetic acid
38. α-[(2-Furylmethyl)amino]-1-benzylindole-3-acetic acid
39. α-[(2-Thienylmethyl)amino]-1-benzylindole-3-acetic acid
40. α-(3,4-Dichlorobenzylamino)-1-benzylindole-3-acetic acid
41. Methyl α-[3-(trifluoromethyl)benzylamino]-indole-3-acetate hydrochloride
42. 4'-Phenylphenacyl α-[3-(trifluoromethyl)benzylamino]-1-benzylindole-3-acetate
43. 3,4,5-Trimethoxybenzyl α-[3-(trifluoromethyl)benzylamino]-1-benzylindole-3-acetate hydrochloride
44. α-(3-Fluorobenzylamino)-1-benzylindole-3-acetic acid
45. α-[3-(Triufluoromethyl)benzylamino)-1-benzyl-5-methylindole-3-acetic acid
46. α-[3-(Trifluoromethyl)benzylamino)-1-benzyl-5-fluoroindole-3-acetic acid
47. Ethyl α-[3-(trifluoromethyl)benzylamino]-1-acetylindole-3-acetate 49. Ethyl α-[3-(trifluoromethyl)benzylamino]-1-benzoylindole-3-acetate

CHART I

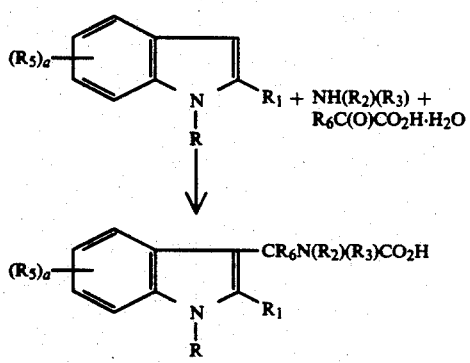

CHART II

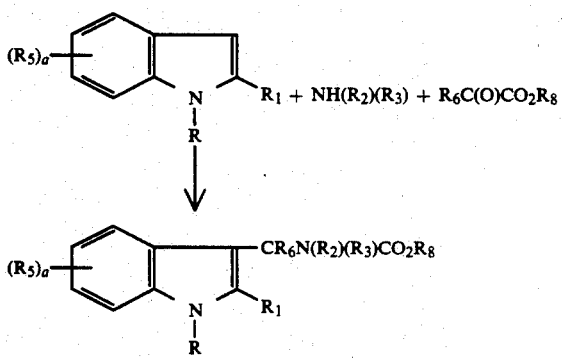

CHART III

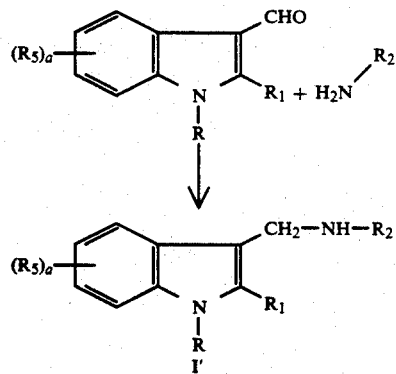

We claim:
1. A compound having the formula

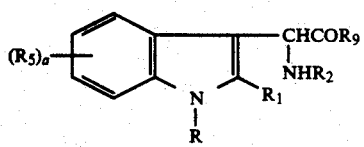

wherein R is hydrogen or benzyl, $R_1$ is hydrogen, $R_2$ is trifluoromethylbenzyl or furylmethyl and $R_9$ is selected from the group consisting of hydroxy, $OR_8$ and OM wherein $R_8$ is $C_1$–$C_{10}$ alkyl, $R_5$ is hydrogen, benzyloxy or methoxy, a is 0 or 1, and M is a pharmacologically acceptable cation; with the proviso that the compound is not Methyl α-[N-methyl-N-3-(trifluoromethyl)benzylamino]-1-benzyl-indole-3-acetate, Methyl α-[N-methyl-N-3-(trifluoromethyl)benzylamino]-1-benzyl-indole-3-acetate hydrochloride, α-[N-methyl-N-3-(trifluoromethyl)benzylamino]-1-benzylindole-3-acetic acid, Methyl α-[3-(trifluoromethyl)benzylamino]indole-3-acetate hydrochloride, Ethyl α-[3-(trifluoromethyl)benzylamino]indole-3-acetate hydrochloride, α-[3-(Trifluoromethyl)benzylamino]-1-benzylindole-3-acetic acid p-phenylphenacyl ester, α-[3-(Trifluoromethyl)benzylamino]-1-benzylindole-3-acetic acid 1-methyl-3-butenyl ester, 2-[3-(Trifluoromethyl)benzylamino]-2-(1-benzyl-3-indolyl)ethanol, Methyl α-[3-(trifluoromethyl)benzylamino]-1-acetoxymethylindole-3-acetate, Methyl α-[3-(trifluoromethyl)benzylamino]-1-acetoxymethylindole-3-acetate hydrochloride, Methyl α-(benzylamino)-indole-3-acetate, α-(Phenylpropylamino)-1-benzylindole-3-acetic acid, Methyl α-[4-(aminosulfonyl)phenylethylamino]-indole-3-acetate, α-Methylamino-1-benzylindole-3-acetic acid, α-(Phenylethylamino)-1-benzylindole-3-acetic acid, α-[4-(aminosulfonyl)phenylethylamino]-1-benzylindole-3-acetic acid, α-[(Tetrahydro-2-furanyl)methylamino]-1-benzylindole-3-acetic acid, α-[3-(Trifluoromethyl)benzylamino]-1-benzylindole-3-acetic acid N,N-dimethylamide, Ethyl α-[3-(trifluoromethyl)benzylamino]-indole-3-acetate, α-[(2-Furylmethyl)amino]-indole-3-acetic acid, α-Benzylamino-indole-3-acetic acid, α-[3-Trifluoromethyl)benzylamino]-1-benzylindole-3-acetic acid amide, α-[4-(Methoxycarbonyl)benzylamino]-1-benzylindole-3-acetic acid, Methyl α-[3-(trifluoromethyl)benzylamino]-1-acetoxymethylindole-3-acetate, methyl α-[3-(trifluoromethyl)benzylamino]-1-acetoxymethylindole-3-acetate hydrochloride.

2. A compound according to claim 1 wherein $R_2$ is trifluoromethylbenzyl.

3. A compound according to claim 2 selected from the group consisting of

Methyl α-[3-(trifluoromethyl)benzylamino]-5-methoxyindole-3-acetate,

α-[3-(Trifluoromethyl)benzylamino]-1-benzylindole-3-acetic acid,

α-[3-(Trifluoromethyl)benzylamino]-1-benzylindole-3-acetic acid hydrochloride.

Sodium α-[3-(trifluoromethyl)benzylamino]-1-benzylindole-3-acetate,

Methyl α-[3-(trifluoromethyl)benzylamino]-1-benzylindole-3-acetate hydrochloride, α-[3-(Trifluoromethyl)benzylamino]-1-phenylindole-3-acetic acid, α-[3-(Trifluoromethyl)benzylamino]-1-benzyl-5-methoxyindole-3-acetic acid, α-[3-(Trifluoromethyl)benzylamino]-1-benzyl-5-chloroindole-3-acetic acid,
Ethyl α-[3-(trifluoromethyl)benzylamino]-1-benzylindole-3-acetate,
Ethyl α-[3-(trifluoromethyl)benzylamino]-1-benzylindole-3-acetate oxalate (1:1),
Ethyl α-[3-(trifluoromethyl)benzylamino]-1-benzylindole-3-acetate hydrochloride,
α-[3-(Trifluoromethyl)benzylamino]-indole-3-acetic acid,
Ethyl α-[3-(Trifluoromethyl)-benzylamino]-indole-3-acetate,
α-[3-(Trifluoromethyl)benzylamino]-1-benzyl-5-methylindole-3-acetic acid,
α-[3-(Trifluoromethyl)benzyl-amino]-1-benzyl-5-methoxy-6-methylindole-3-acetic acid,
α-[3-(Trifluoromethyl)benzylamino]-1-benzyl-5,6-methylenedioxyindole-3-acetic acid,
α-[3-(Trifluoromethyl)benzylamino]-1-benzyl-5-methoxy-6-isopropylindole-3-acetic acid,
α-[3-(Trifluoromethyl)benzylamino]-1-benzyl-5-methoxy-4-methylindole-3-acetic acid,
α-[3-(Trifluoromethyl)benzylamino]-1-benzyl-5-methoxy-6-chloroindole-3-acetic acid,
α-[3-(Trifluoromethyl)benzylamino]-1-benzyl-6-methylindole-3-acetic acid,
α-[3-(Trifluoromethyl)benzylamino]-1-benzyl-5,6-dimethoxyindole-3-acetic acid,
α-[3-(Trifluoromethyl)benzylamino]-1-benzyl-5-methoxy-7-methylindole-3-acetic acid,
α-[3-(Trifluoromethyl)benzylamino]-1-benzyl-6-methoxyindole-3-acetic acid,
α-[3-(Trifluoromethyl)benzylamino]-1-benzyl-5-acetoxyindole-3-acetic acid,
α-[3-(Trifluoromethyl)benzylamino]-1-benzyl-5-hydroxyindole-3-acetic acid,
α-[3-(Trifluoromethyl)benzylamino]-1-benzyl-5-ethoxyindole-3-acetic acid,
α-[3-(Trifluoromethyl)benzylamino]-1-benzyl-5-benzyloxyindole-3-acetic acid,
α-[3-(Trifluoromethyl)benzylamino]-1-benzyl-5-methoxyindole-3-acetic acid,
Ethyl α-[3-(trifluoromethyl)benzylamino]-1-benzylindole-3-acetate maleic acid salt,
α-[3-(Trifluoromethyl)benzylamino]-indole-3-acetate hydrochloride,
α-[3-(Trifluoromethyl)benzylamino]-1-benzyl-5-fluoroindole-3-acetic acid,
α-[3-(Trifluoromethyl)benzylamino]-1-benzylindole-3-acetic acid 1-methyl-3-butenyl ester.

4. A compound according to claim 3, α-[3-(trifluoromethyl)benzylamino]-1-benzylindole-5-methoxyindole-3-acetic acid.

5. A compound according to claim 3, α-[3-(trifluoromethyl)benzylamino]-indole-3-acetic acid.

6. A compound according to claim 3, methyl α-[3-(trifluoromethyl)-benzylamino]-1-benzylindole-3-acetate hydrochloride.

7. A compound according to claim 1, wherein $R_2$ is furylmethyl.

8. A compound according to claim 7, α-[(2-furylmethyl)amino]-benzylindole-3-acetic acid.

9. A compound according to claim 1 selected from the group consisting of
α-Benzylamino-1-benzylindole-3-acetic acid,
α-[(3-Pyridinylmethyl)amino-1-benzylindole-3-acetic acid,
α-(4-Methoxybenzylamino)-1-benzylindole-3-acetic acid,
α-[(Phenylbutyl)amino]-1-benzylindole-3-acetic acid,
α-[(S)-α-methylbenzylamino]-1-benzylindole-3-acetic acid,
α-(N-Methylbenzylamino)-1-benzylindole-3-acetic acid hydrate (4:1),
α(3-Chlorobenzylamino)-1-benzylindole-3-acetic acid,
α-(2-Chlorobenzylamino)-1-benzylindole-3-acetic acid, α-[(2-Thienylmethyl)amino]-1-benzylindole-3-acetic acid,
α-(3-Fluorobenzylamino)-1-benzylindole-3-acetic acid,
α-(4-Fluorobenzylamino-1-benzylindole-3-acetic acid,
α-(3-Methoxybenzylamino-1-benzylindole-3-acetic acid,
α-(3-Methylbenzylamino)-1-benzylindole-3-acetic acid,
α-(3,4-Dichlorobenzylamino)-1-benzylindole-3-acetic acid
α-(Diphenylmethylamino)-indole-3-acetic acid hydrate (1:0:7).

10. A compound selected from the group consisting of
Methyl (±)-α-(1-phenylmethyl-3-indolylmethyl)amino-phenylacetate,
Methyl (R)-α-(1-phenylmethyl-3-indolylmethyl)amino-phenylacetate,
Methyl (S)-α-(1-phenylmethyl-3-indolylmethyl)amino-phenylacetate,
Methyl (±)-α-(1-phenylmethyl-3-indolylmethyl)amino-(3-trifluoromethylphenyl) acetate,
Methyl (R)-α-(3-indolylmethyl)amino-phenylacetate,
Methyl (S)-α-(3-indolylmethyl)amino-phenylacetate,
Methyl (±)-α-(1-phenylmethyl-5-methoxy-3-indolylmethyl)amino-(3-trifluoromethylphenyl) acetate,
Methyl (±)-α-(5-methoxy-3-indolylmethyl)amino-(3-trifluoromethylphenyl) acetate,
Methyl (R)-α-(1-phenylmethyl-5-methoxy-3-indolylmethyl)aminophenylacetate, and
Methyl (S)-α-(1-phenylmethyl-5-methoxy-3-indolylmethyl)aminophenylacetate.

* * * * *